(12) United States Patent
Tamburini et al.

(10) Patent No.: US 8,168,758 B2
(45) Date of Patent: May 1, 2012

(54) ANTI-MN ANTIBODIES AND METHODS OF USING SAME

(75) Inventors: Paul Tamburini, Kensington, CT (US); Gerald Ranges, Hamden, CT (US); Lila Adnane, Pine Brook, NJ (US); Timothy Mccabe, Doylestown, PA (US); Pamela Trail, Madison, CT (US); Sha Ha, Blue Bell, PA (US)

(73) Assignee: Bayer HealthCare LLC, Tarrytown, NY (US)

( * ) Notice: Subject to any disclaimer, the term of this patent is extended or adjusted under 35 U.S.C. 154(b) by 464 days.

(21) Appl. No.: 12/086,320

(22) PCT Filed: Dec. 12, 2006

(86) PCT No.: PCT/US2006/047445
§ 371 (c)(1),
(2), (4) Date: Nov. 23, 2009

(87) PCT Pub. No.: WO2007/070538
PCT Pub. Date: Jun. 21, 2007

(65) Prior Publication Data
US 2010/0129315 A1 May 27, 2010

Related U.S. Application Data

(60) Provisional application No. 60/749,716, filed on Dec. 12, 2005.

(51) Int. Cl.
*C12P 21/08* (2006.01)
(52) U.S. Cl. ............... 530/387.3; 530/387.1; 530/387.7; 530/388.26; 530/388.8; 530/391.3; 530/391.7
(58) Field of Classification Search .................. 530/350, 530/387.1, 387.3, 387.7, 388.26, 388.8, 391.3, 530/391.7
See application file for complete search history.

(56) References Cited

U.S. PATENT DOCUMENTS

| | | |
|---|---|---|
| 6,051,226 A | 4/2000 | Zavada et al. |
| 7,115,715 B2 | 10/2006 | Zavada et al. |
| 2003/0157090 A1 | 8/2003 | Benvenuto et al. |
| 2004/0126379 A1 | 7/2004 | Adolf et al. |
| 2004/0132980 A1 | 7/2004 | LaRosa et al. |
| 2005/0136057 A1 | 6/2005 | Sato et al. |
| 2005/0181448 A1 | 8/2005 | Popplewell et al. |

FOREIGN PATENT DOCUMENTS

| | | |
|---|---|---|
| EP | 1004313 | 5/2007 |
| WO | WO-02/062972 A2 | 8/2002 |
| WO | WO-03/033674 A2 | 4/2003 |
| WO | WO-03/048328 A2 | 6/2003 |
| WO | WO 03/070760 | 8/2003 |
| WO | WO-03/100029 A2 | 12/2003 |
| WO | WO-2004/017923 A2 | 3/2004 |

OTHER PUBLICATIONS

Shu-Yuan Liao, et al., "Identification of the MN/CA9 Protein As a Reliable Diagnostic Biomarker of Clear Cell Carcinoma of the Kidney"; Advances in Brief; Cancer Research 57, 1997, 2827-2831.
J. S. Lam et al.: "G250: a carbonic anhydrase IX monoclonal antibody." Current Oncology Reports, vol. 7, No. 2, Mar. 2005 pp. 109-115.
M. Zato'vicova et al.: "Monoclonal antibodies generated in carbonic anhydrase IX-deficient mice recognize different domains of tumour-associated hypoxia-induced carbonic anhydrase IX" Journal of Immunological Methods, Elsevier Science Publsihers B.V., Amsterdam, NL, vol. 282, No. 1-2, Nov. 1, 2003, pp. 117-134.
Z. Varga et al: "A Prospective Open-Label Single-Arm Phase II Study Of Chimeric Monoclonal Antibody CG250 in Advanced Renal Cell Carcinoma Patients" Folia Biologica (Praha), vol. 49, No. 2, Jan. 1, 2003, pp. 74-77.

*Primary Examiner* — Stephen Rawlings
(74) *Attorney, Agent, or Firm* — Thomas C. Blankinship

(57) ABSTRACT

The invention provides antibodies having an antigenic binding site specifically directed against an MN protein, and methods for using such antibodies in treating and diagnosing an MN-related disorder.

29 Claims, 49 Drawing Sheets

| SEQ ID NO | CDR | DNA sequence | Fab code |
|---|---|---|---|
| | VH3-CDR1 | | |
| 1 | 1 | GGATTTACCTTTTCTTCTTATGGTATGTCT | 3ee9 |
| 2 | 2 | GGATTTACCTTTTCTTCTTATGGTATGCAT | 3ef2 |
| 3 | 3 | GGATTTACCTTTTCTAATAATGCTATGAAT | 1e4 |
| 4 | 4 | GGATTTACCTTTTCTGATTATTCTATTAAT | 3a4 |
| 5 | 5 | GGATTTACCTTTTCTTCTTATGGTATTTCT | 3ab4, 3ah10 |
| 6 | 6 | GGATTTACCTTTTCTAATTATGGTATTTCT | 3bb2 |
| | VH3-CDR2 | | |
| 7 | 1 | GGTATCTCTTCTCTTGGTAGCACTACCTATTATGCGGATAGCGTGAAAGGC | 3ee9 |
| 8 | 2 | GCTATCTCTTATTCTTCTAGCTCTACCTCTTATGCGGATAGCGTGAAAGGC | 3ef2 |
| 9 | 3 | GGTATCTCTTATGATTCTAGCAAGACCTATTATGCGGATAGCGTGAAAGGC | 1e4 |
| 10 | 4 | AATATCTCTTATTCTGGTAGCTCTACCTATTATGCGGATAGCGTGAAAGGC | 3a4 |
| 11 | 5 | GGTATCTCTTATTCTGGTAGCTCTACCTATTATGCGGATAGCGTGAAAGGC | 3ab4 |
| 12 | 6 | TCTATCTCTTATTCTGGTAGCAATACCTATTATGCGGATAGCGTGAAAGGC | 3ah10 |
| 13 | 7 | GCTATCTCTTATTATGGTAGCAATACCTATTATGCGGATAGCGTGAAAGGC | 3bb2 |
| | VH3-CDR3 | | |
| 14 | 1 | ACTGGTTCTCCTGGTACTTTTATGCATGGTGATCAT | 3ee9 |
| 15 | 2 | CTTTCTTATACTGGTTTTGCTGTT | 3ef2 |
| 16 | 3 | CTTACTTATACTGGTGCTTATCGT | 1e4 |
| 17 | 4 | TTTAAGTATTCTGGTGGTTCTGATTCT | 3a4 |
| 18 | 5 | CTTAAGCCTTATCGTCATAAGAATGGTTGGTTTGATTAT | 3ab4 |
| 19 | 6 | ATGAAGCCTATGCGTGGTTATTCTGGTGCTGTT | 3ah10 |
| 20 | 7 | CTTAAGGGTGGTTCTGGTTTTGTT | 3bb2 |

Figure 1a

| SEQ ID NO | CDR | DNA sequence | Fab code |
|---|---|---|---|
| | VH1b-CDR1 | | |
| 21 | 1 | GGATATACCTTTACTACTAATTATATGCAT | 1aa1 |
| | VH1b-CDR2 | | |
| 22 | 1 | ATTATCAATCCGCATAATGGCTCTACGTCTTACGCGCAGAAGTTTCAGGGC | 1aa1 |
| | VH1b-CDR3 | | |
| 23 | 1 | GGTCGTTATTTTCTTATGGATGTT | 1aa1 |
| | VH5-CDR1 | | |
| 24 | 1 | GGATATTCCTTTTCTAAGTATTGGATTGGT | 5a6 |
| 25 | 2 | GGATATTCCTTTACTGGTTATATTTCT | 5aa3 |
| | VH5-CDR2 | | |
| 26 | 1 | ATTATCTATCCGACTGATAGCTATACCCGTTATTCTCCGAGCTTTCAGGGC | 5a6 |
| 27 | 2 | ATTATCTATCCGGGTGATAGCTATACCAATTATTCTCCGAGCTTTCAGGGC | 5aa3 |
| | VH5-CDR3 | | |
| 28 | 1 | ACTCATGGTTATTATAAGAATGGTCGTATGGATGTT | 5a6 |
| 29 | 2 | TATTCTGGTCCTAATTGGGATGTTATGGATTCT | 5aa3 |
| SEQ ID NO | CDR | DNA sequence | Fab code |
| | Vk1-CDR1 | | |
| 30 | 1 | AGAGCGAGCCAGAATATTCTTTCTTATCTGAAT | 1aa1 |
| 31 | 2 | AGAGCGAGCCAGAATATTTCTAATTATCTGAAT | 3ab4 |
| 32 | 3 | AGAGCGAGCCAGGATATTTCTAATCGTCTGGCT | 3ah10 |
| 33 | 4 | AGAGCGAGCCAGGATATTAATAATTATCTGTCT | 3ee9 |

Figure 1b

| SEQ ID NO | CDR | DNA sequence | Fab code |
|---|---|---|---|
| | VLk1-CDR2 | | |
| 34 | 1 | TATGCTGCTTCTTCTTTGCAAAGC | 1aa1 |
| 35 | 2 | CATAAGGTTTCTAATTTGCAAAGC | 3ab4 |
| 36 | 3 | TATGATGCTAATTCTTTGCAAAGC | 3ah10 |
| 37 | 4 | TATGGTGCTTCTAATTTGCAAAGC | 3ee9 |
| | VLk1-CDR3 | | |
| 38 | 1 | CAGCAGTATGGTTCTGTTCCT | 1aa1 |
| 39 | 2 | CTTCAGTATGATGATTTTCCTCGT | 3ab4 |
| 40 | 3 | TTTCAGTATTCTGGTCCT | 3ah10 |
| 41 | 4 | CAGCAGTATTATGGTCGTCCTACT | 3ee9 |
| | VLk2-CDR1 | | |
| 42 | 1 | AGAAGCAGCCAAAGCCTGGTTTATTCTAATGGCAATACTACTCTGTCT | 3bb2 |
| 43 | 2 | AGAAGCAGCCAAAGCCTGGTTCATTCTAATGGCTATAATTATCTGTCT | 5a6 |
| | VLk2-CDR2 | | |
| 44 | 1 | TATGGTGTTTCTAATCGTGCCAGT | 3bb2 |
| 45 | 2 | TATCTTGGTTCTAATCGTGCCAGT | 5a6 |
| | VLk2-CDR3 | | |
| 46 | 1 | CAGCAGTATAATTCTTTTCCTCGT | 3bb2 |
| 47 | 2 | CATCAGTATGGTGATTTTTCTGAT | 5a6 |
| | VLλ1-CDR1 | | |
| 48 | 1 | AGCGGCAGCAGCAGCAACATTGGTTCTTATTATGTGAAT | 5aa3 |
| | VLλ1-CDR2 | | |
| 49 | 1 | CTTCTGATTTATGCTGATGATAAGCGTCCCTCA | 5aa3 |

Figure 1c

| SEQ ID NO | CDR | DNA sequence | Fab code |
|---|---|---|---|
| | VLλ1-CDR3 | | |
| 50 | 1 | CAGTCTTATGATTCTACTAAGGATGATTCT | 5aa3 |
| | VLλ3-CDR1 | | |
| 51 | 1 | AGCGGCGATAATCTTGGTTCTTATTATGTTCAT | 1e4, 3ef2 |
| 52 | 2 | AGCGGCGATAATCTTCCTGATTTTTATGTTCAT | 3a4 |
| | VLλ3-CDR2 | | |
| 53 | 1 | CTTGTGATTTATGATGATAATAATCGTCCCTCA | 1e4, 3ef2 |
| 54 | 2 | CTTGTGATTTCTGAGGATAATAAGCGTCCCTCA | 3a4 |
| | VLλ3-CDR3 | | |
| 55 | 1 | CAGTCTTATGATTTTGGTAAGGTT | 1e4, 3ef2 |
| 56 | 2 | TCTACTTATGGTTATACTTATTCTTATTCT | 3a4 |

Figure 1d

| SEQ ID NO | CDR | Amino Acid sequence | Fab code |
|---|---|---|---|
|  | VH3-CDR1 |  |  |
| 57 | 1 | GFTFSSYGMS | 3ee9 |
| 58 | 2 | GFTFSSYGMH | 3ef2 |
| 59 | 3 | GFTFSNNAMN | 1e4 |
| 60 | 4 | GFTFSDYSIN | 3a4 |
| 61 | 5 | GFTFSSYGIS | 3ab4, 3ah10 |
| 62 | 6 | GFTFSNYGIS | 3bb2 |
|  | VH3-CDR2 |  |  |
| 63 | 1 | GISSLGSTTYYADSVKG | 3ee9 |
| 64 | 2 | AISYSSSSTSYADSVKG | 3ef2 |
| 65 | 3 | GISYDSSKTYYADSVKG | 1e4 |
| 66 | 4 | NISYSGSSTYYADSVKG | 3a4 |
| 67 | 5 | GISYSGSSTYYADSVKG | 3ab4 |
| 68 | 6 | SISYSGSNTYYADSVKG | 3ah10 |
| 69 | 7 | AISYYGSNTYYADSVKG | 3bb2 |
|  | VH3-CDR3 |  |  |
| 70 | 1 | TGSPGTFMHGDH | 3ee9 |
| 71 | 2 | LSYTGFAV | 3ef2 |
| 72 | 3 | LTYTGAYR | 1e4 |
| 73 | 4 | FKYSGGSDS | 3a4 |
| 74 | 5 | LKPYRHKNGWFDY | 3ab4 |
| 75 | 6 | MKPMRGYSGAV | 3ah10 |
| 76 | 7 | LKGGSGFV | 3bb2 |
|  | VH1b-CDR1 |  |  |
| 77 | 1 | GYTFTTNYMH | 1aa1 |
|  | VH1b-CDR2 |  |  |
| 78 | 1 | IINPHNGSTSYAQKFQG | 1aa1 |
|  | VH1b-CDR3 |  |  |
| 79 | 1 | GRYFLMDV | 1aa1 |
|  | VH5-CDR1 |  |  |
| 80 | 1 | GYSFSKYWIG | 5a6 |
| 81 | 2 | GYSFTGYIS | 5aa3 |

Figure 2a

| SEQ ID NO | CDR | Amino Acid sequence | Fab code |
|---|---|---|---|
|  | VH5-CDR2 |  |  |
| 82 | 1 | IIYPTDSYTRYSPSFQG | 5a6 |
| 83 | 2 | IIYPGDSYTNYSPSFQG | 5aa3 |
|  | VH5-CDR3 |  |  |
| 84 | 1 | THGYYKNGRMDV | 5a6 |
| 85 | 2 | YSGPNWDVMDS | 5aa3 |
|  | VLk1-CDR1 |  |  |
| 86 | 1 | RASQNILSYLN | 1aa1 |
| 87 | 2 | RASQNISNYLN | 3ab4 |
| 88 | 3 | RASQDISNRLA | 3ah10 |
| 89 | 4 | RASQDINNYLS | 3ee9 |
|  | VLk1-CDR2 |  |  |
| 90 | 1 | YAASSLQS | 1aa1 |
| 91 | 2 | HKVSNLQS | 3ab4 |
| 92 | 3 | YDANSLQS | 3ah10 |
| 93 | 4 | YGASNLQS | 3ee9 |
|  | VLk1-CDR3 |  |  |
| 94 | 1 | QQYGSVP | 1aa1 |
| 95 | 2 | LQYDDFPR | 3ab4 |
| 96 | 3 | FQYSGP | 3ah10 |
| 97 | 4 | QQYYGRPT | 3ee9 |
|  | VLk2-CDR1 |  |  |
| 98 | 1 | RSSQSLVYSNGNTTLS | 3bb2 |
| 99 | 2 | RSSQSLVHSNGYNYLS | 5a6 |
|  | VLk2-CDR2 |  |  |
| 100 | 1 | YGVSNRAS | 3bb2 |
| 101 | 2 | YLGSNRAS | 5a6 |
|  | VLk2-CDR3 |  |  |
| 102 | 1 | QQYNSFPR | 3bb2 |
| 103 | 2 | HQYGDFSD | 5a6 |

Figure 2b

| SEQ ID NO | CDR | Amino Acid sequence | Fab code |
|---|---|---|---|
|  | VLλ1-CDR1 |  |  |
| 104 | 1 | SGSSSNIGSYYVN | 5aa3 |
|  | VLλ1-CDR2 |  |  |
| 105 | 1 | LLIYADDKRPS | 5aa3 |
|  | VLλ1-CDR3 |  |  |
| 106 | 1 | QSYDSTKDDS | 5aa3 |
|  | VLλ3-CDR1 |  |  |
| 107 | 1 | SGDNLGSYYVH | 1e4, 3ef2 |
| 108 | 2 | SGDNLPDFYVH | 3a4 |
|  | VLλ3-CDR2 |  |  |
| 109 | 1 | LVIYDDNNRPS | 1e4, 3ef2 |
| 110 | 2 | LVISEDNKRPS | 3a4 |
|  | VLλ3-CDR3 |  |  |
| 111 | 1 | QSYDFGKV | 1e4, 3ef2 |
| 112 | 2 | STYGYTYSYS | 3a4 |

Figure 2c

| SEQ ID NO | Antibody chain | DNA sequence | Fab code |
|---|---|---|---|
| 113 | VH1b | GAATTGGTTCAGAGCGGCGCGGAAGTGAAAAAACCG GGCGCGAGCGTGAAAGTGAGCTGCAAAGCCTCCGGA TATACCTTTACTACTAATTATATGCATTGGGTCCGC CAAGCCCCTGGGCAGGGTCTCGAGTGGATGGGCATT ATCAATCCGCATAATGGCTCTACGTCTTACGCGCAG AAGTTTCAGGGCCGGGTGACCATGACCCGTGATACC AGCATTAGCACCGCGTATATGGAACTGAGCAGCCTG CGTAGCGAAGATACGGCCGTGTATTATTGCGCGCGT GGTCGTTATTTTCTTATGGATGTTTGGGGCCAAGGC ACCCTGGTGACGGTTAGCTCAGC | 1aa1 |
| 114 | Vk1 | GATATCCAGATGACCCAGAGCCCGTCTAGCCTGAGC GCGAGCGTGGGTGATCGTGTGACCATTACCTGCAGA GCGAGCCAGAATATTCTTTCTTATCTGAATTGGTAC CAGCAGAAACCAGGTAAAGCACCGAAACTATTAATT TATGCTGCTTCTTCTTTGCAAAGCGGGGTCCCGTCC CGTTTTAGCGGCTCTGGATCCGGCACTGATTTTACC CTGACCATTAGCAGCCTGCAACCTGAAGACTTTGCG GTTTATTATTGCCAGCAGTATGGTTCTGTTCCTACC TTTGGCCAGGGTACGAAAGTTGAAATTAAACGTACG | 1aa1 |
| 115 | VH3 | GAATTGGTGGAAAGCGGCGGCGGCCTGGTGCAACCG GGCGGCAGCCTGCGTCTGAGCTGCGCGGCCTCCGGA TTTACCTTTTCTAATAATGCTATGAATTGGGTGCGC CAAGCCCCTGGGAAGGGTCTCGAGTGGGTGAGCGGT ATCTCTTATGATTCTAGCAAGACCTATTATGCGGAT AGCGTGAAAGGCCGTTTTACCATTTCACGTGATAAT TCGAAAAACACCCTGTATCTGCAAATGAACAGCCTG CGTGCGGAAGATACGGCCGTGTATTATTGCGCGCGT CTTACTTATACTGGTGCTTATCGTTGGGGCCAAGGC ACCCTGGTGACGGTTAGCTCAGC | 1e4 |
| 116 | VL3 | GATATCGAACTGACCCAGCCGCCTTCAGTGAGCGTT GCACCAGGTCAGACCGCGCGTATCTCGTGTAGCGGC GATAATCTTGGTTCTTATTATGTTCATTGGTACCAG CAGAAACCCGGGCAGGCGCCAGTTCTTGTGATTTAT GATGATAATAATCGTCCCTCAGGCATCCCGGAACGC TTTAGCGGATCCAACAGCGGCAACACCGCGACCCTG ACCATTAGCGGCACTCAGGCGGAAGACGAAGCGGAT TATTATTGCCAGTCTTATGATTTTGGTAAGGTTGTG TTTGGCGGCGGCACGAAGTTAAC | 1e4 |

Figure 3a

| SEQ ID NO | Anti-body chain | DNA sequence | Fab code |
|---|---|---|---|
| 117 | VH3 | GAATTGGTGGAAAGCGGCGGCGGCCTGGTGCAACCG GGCGGCAGCCTGCGTCTGAGCTGCGCGGCCTCCGGA TTTACCTTTTCTGATTATTCTATTAATTGGGTGCGC CAAGCCCCTGGGAAGGGTCTCGAGTATGTGAGCAAT ATCTCTTATTCTGGTAGCTCTACCTATTATGCGGAT AGCGTGAAAGGCCGTTTTACCATTTCACGTGATAAT TCGAAAAACACCCTGTATCTGCAAATGAACAGCCTG CGTGCGGAAGATACGGCCGTGTATTATTGCGCGCGT TTTAAGTATTCTGGTGGTTCTGATTCTTGGGGCCAA GGCACCCTGGTGACGGTTAGCTCAGC | 3a4 |
| 118 | VL3 | GATATCGAACTGACCCAGCCGCCTTCAGTGAGCGTT GCACCAGGTCAGACCGCGCGTATCTCGTGTAGCGGC GATAATCTTCCTGATTTTTATGTTCATTGGTACCAG CAGAAACCCGGGCAGGCGCCAGTTCTTGTGATTTCT GAGGATAATAAGCGTCCCTCAGGCATCCCGGAACGC TTTAGCGGATCCAACAGCGGCAACACCGCGACCCTG ACCATTAGCGGCACTCAGGCGGAAGACGAAGCGGAT TATTATTGCTCTACTTATGGTTATACTTATTCTTAT TCTGTGTTTGGCGGCGGCACGAAGTTAAC | 3a4 |
| 119 | VH3 | GAATTGGTGGAAAGCGGCGGCGGCCTGGTGCAACCG GGCGGCAGCCTGCGTCTGAGCTGCGCGGCCTCCGGA TTTACCTTTTCTTCTTATGGTATTTCTTGGGTGCGC CAAGCCCCTGGGAAGGGTCTCGAGTGGGTGAGCGGT ATCTCTTATTCTGGTAGCTCTACCTATTATGCGGAT AGCGTGAAAGGCCGTTTTACCATTTCACGTGATAAT TCGAAAAACACCCTGTATCTGCAAATGAACAGCCTG CGTGCGGAAGATACGGCCGTGTATTATTGCGCGCGT CTTAAGCCTTATCGTCATAAGAATGGTTGGTTTGAT TATTGGGGCCAAGGCACCCTGGTGACGGTTAGCTCA GC | 3ab4 |
| 120 | Vk1 | GATATCCAGATGACCCAGAGCCCGTCTAGCCTGAGC GCGAGCGTGGGTGATCGTGTGACCATTACCTGCAGA GCGAGCCAGAATATTTCTAATTATCTGAATTGGTAC CAGCAGAAACCAGGTAAAGCACCGAAACTATTAATT CATAAGGTTTCTAATTTGCAAAGCGGGGTCCCGTCC CGTTTTAGCGGCTCTGGATCCGGCACTGATTTTACC CTGACCATTAGCAGCCTGCAACCTGAAGACTTTGCG GTTTATTATTGCCTTCAGTATGATGATTTTCCTCGT ACCTTTGGCCAGGGTACGAAAGTTGAAATTAAACGT ACG | 3ab4 |

Figure 3b

| SEQ ID NO | Antibody chain | DNA sequence | Fab code |
|---|---|---|---|
| 121 | VH3 | GAATTGGTGGAAAGCGGCGGCGGCCTGGTGCAACCG GGCGGCAGCCTGCGTCTGAGCTGCGCGGCCTCCGGA TTTACCTTTTCTTCTTATGGTATTTCTTGGGTGCGC CAAGCCCCTGGGAAGGGTCTCGAGTGGGTGAGCTCT ATCTCTTATTCTGGTAGCAATACCTATTATGCGGAT AGCGTGAAAGGCCGTTTTACCATTTCACGTGATAAT TCGAAAAACACCCTGTATCTGCAAATGAACAGCCTG CGTGCGGAAGATACGGCCGTGTATTATTGCGCGCGT ATGAAGCCTATGCGTGGTTATTCTGGTGCTGTTTGG GGCCAAGGCACCCTGGTGACGGTTAGCTCAGC | 3ah10 |
| 122 | Vk1 | GATATCCAGATGACCCAGAGCCCGTCTAGCCTGAGC GCGAGCGTGGGTGATCGTGTGACCATTACCTGCAGA GCGAGCCAGGATATTTCTAATCGTCTGGCTTGGTAC CAGCAGAAACCAGGTAAAGCACCGAAACTATTAATT TATGATGCTAATTCTTTGCAAAGCGGGGTCCCGTCC CGTTTTAGCGGCTCTGGATCCGGCACTGATTTTACC CTGACCATTAGCAGCCTGCAACCTGAAGACTTTGCG ACTTATTATTGCTTTCAGTATTCTGGTCCTACCTTT GGCCAGGGTACGAAAGTTGAAATTAAACGTACG | 3ah10 |
| 123 | VH3 | GAATTGGTGGAAAGCGGCGGCGGCCTGGTGCAACCG GGCGGCAGCCTGCGTCTGAGCTGCGCGGCCTCCGGA TTTACCTTTTCTAATTATGGTATTTCTTGGGTGCGC CAAGCCCCTGGGAAGGGTCTCGAGTGGGTGAGCGCT ATCTCTTATTATGGTAGCAATACCTATTATGCGGAT AGCGTGAAAGGCCGTTTTACCATTTCACGTGATAAT TCGAAAAACACCCTGTATCTGCAAATGAACAGCCTG CGTGCGGAAGATACGGCCGTGTATTATTGCGCGCGT CTTAAGGGTGGTTCTGGTTTTGTTTGGGGCCAAGGC ACCCTGGTGACGGTTAGCTCAGC | 3bb2 |
| 124 | Vk2 | GATATCGTGATGACCCAGAGCCCACTGAGCCTGCCA GTGACTCCGGGCGAGCCTGCGAGCATTAGCTGCAGA AGCAGCCAAAGCCTGGTTTATTCTAATGGCAATACT ACTCTGTCTTGGTACCTTCAAAAACCAGGTCAAAGC CCGCAGCTATTAATTTATGGTGTTTCTAATCGTGCC AGTGGGGTCCCGGATCGTTTTAGCGGCTCTGGATCC GGCACCGATTTTACCCTGAAAATTAGCCGTGTGGAA GCTGAAGACGTGGGCGTGTATTATTGCAGCAGTAT AATTCTTTTCCTCGTACCTTTGGCCAGGGTACGAAA GTTGAAATTAAACGTACG | 3bb2 |

Figure 3c

| SEQ ID NO | Antibody chain | DNA sequence | Fab code |
|---|---|---|---|
| 125 | VH3 | GAATTGGTGGAAAGCGGCGGCGGCCTGGTGCAACCG GGCGGCAGCCTGCGTCTGAGCTGCGCGGCCTCCGGA TTTACCTTTTCTTCTTATGGTATGTCTTGGGTGCGC CAAGCCCCTGGGAAGGGTCTCGAGTGGGTGAGCGGT ATCTCTTCTCTTGGTAGCACTACCTATTATGCGGAT AGCGTGAAAGGCCGTTTTACCATTTCACGTGATAAT TCGAAAAACACCCTGTATCTGCAAATGAACAGCCTG CGTGCGGAAGATACGGCCGTGTATTATTGCGCGCGT ACTGGTTCTCCTGGTACTTTTATGCATGGTGATCAT TGGGGCCAAGGCACCCTGGTGACGGTTAGCTCAGC | 3ee9 |
| 126 | Vk1 | GATATCCAGATGACCCAGAGCCCGTCTAGCCTGAGC GCGAGCGTGGGTGATCGTGTGACCATTACCTGCAGA GCGAGCCAGGATATTAATAATTATCTGTCTTGGTAC CAGCAGAAACCAGGTAAAGCACCGAAACTATTAATT TATGGTGCTTCTAATTTGCAAAGCGGGGTCCCGTCC CGTTTTAGCGGCTCTGGATCCGGCACTGATTTTACC CTGACCATTAGCAGCCTGCAACCTGAAGACTTTGCG GTTTATTATTGCCAGCAGTATTATGGTCGTCCTACT ACCTTTGGCCAGGGTACGAAAGTTGAAATTAAACGT ACG | 3ee9 |
| 127 | VH5 | GAATTGGTTCAGAGCGGCGCGGAAGTGAAAAAACCG GGCGAAAGCCTGAAAATTAGCTGCAAAGGTTCCGGA TATTCCTTTTCTAAGTATTGGATTGGTTGGGTGCGC CAGATGCCTGGGAAGGGTCTCGAGTGGATGGGCATT ATCTATCCGACTGATAGCTATACCCGTTATTCTCCG AGCTTTCAGGGCCAGGTGACCATTAGCGCGGATAAA AGCATTAGCACCGCGTATCTTCAATGGAGCAGCCTG AAAGCGAGCGATACGGCCATGTATTATTGCGCGCGT ACTCATGGTTATTATAAGAATGGTCGTATGGATGTT TGGGGCCAAGGCACCCTGGTGACGGTTAGCTCAGC | 5a6 |
| 128 | Vk2 | GATATCGTGATGACCCAGAGCCCACTGAGCCTGCCA GTGACTCCGGGCGAGCCTGCGAGCATTAGCTGCAGA AGCAGCCAAAGCCTGGTTCATTCTAATGGCTATAAT TATCTGTCTTGGTACCTTCAAAAACCAGGTCAAAGC CCGCAGCTATTAATTTATCTTGGTTCTAATCGTGCC AGTGGGGTCCCGGATCGTTTTAGCGGCTCTGGATCC GGCACCGATTTTACCCTGAAAATTAGCCGTGTGGAA GCTGAAGACGTGGGCGTGTATTATTGCCATCAGTAT GGTGATTTTTCTGATACCTTTGGCCAGGGTACGAAA GTTGAAATTAAACGTACG | 5a6 |

Figure 3d

| SEQ ID NO | Antibody chain | DNA sequence | Fab code |
|---|---|---|---|
| 129 | VH5 | GAATTGGTTCAGAGCGGCGCGGAAGTGAAAAAACCG GGCGAAAGCCTGAAAATTAGCTGCAAAGGTTCCGGA TATTCCTTTACTGGTTATATTTCTTGGGTGCGCCAA GCCCCTGGGAAGGGTCTCGAGTGGATGGGCATTATC TATCCGGGTGATAGCTATACCAATTATTCTCCGAGC TTTCAGGGCCAGGTGACCATTAGCGCGGATAAAAGC ATTAGCACCGCGTATCTTCAATGGAGCAGCCTGAAA GCGAGCGATACGGCCATGTATTATTGCGCGCGTTAT TCTGGTCCTAATTGGGATGTTATGGATTCTTGGGGC CAAGGCACCCTGGTGACGGTTAGCTCAGC | 5aa3 |
| 130 | VL1 | GATATCGTGCTGACCCAGCCGCCTTCAGTGAGTGGC GCACCAGGTCAGCGTGTGACCATCTCGTGTAGCGGC AGCAGCAGCAACATTGGTTCTTATTATGTGAATTGG TACCAGCAGTTGCCCGGGACGGCGCCGAAACTTCTG ATTTATGCTGATGATAAGCGTCCCTCAGGCGTGCCG GATCGTTTTAGCGGATCCAAAAGCGGCACCAGCGCG AGCCTTGCGATTACGGGCCTGCAAAGCGAAGACGAA GCGGATTATTATTGCCAGTCTTATGATTCTACTAAG GATGATTCTGTGTTTGGCGGCGGCACGAAGTTAAC | 5aa3 |
| 131 | VH3 | GAATTGGTGGAAAGCGGCGGCGGCCTGGTGCAACCG GGCGGCAGCCTGCGTCTGAGCTGCGCGGCCTCCGGA TTTACCTTTTCTTCTTATGGTATGCATTGGGTGCGC CAAGCCCCTGGGAAGGGTCTCGAGTATGTGAGCGCT ATCTCTTATTCTTCTAGCTCTACCTCTTATGCGGAT AGCGTGAAAGGCCGTTTTACCATTTCACGTGATAAT TCGAAAAACACCCTGTATCTGCAAATGAACAGCCTG CGTGCGGAAGATACGGCCGTGTATTATTGCGCGCGT CTTTCTTATACTGGTTTTGCTGTTTGGGGCCAAGGC ACCCTGGTGACGGTTAGCTCAGC | 3ef2 |
| 132 | VL3 | GATATCGAACTGACCCAGCCGCCTTCAGTGAGCGTT GCACCAGGTCAGACCGCGCGTATCTCGTGTAGCGGC GATAATCTTGGTTCTTATTATGTTCATTGGTACCAG CAGAAACCCGGGCAGGCGCCAGTTCTTGTGATTTAT GATGATAATAATCGTCCCTCAGGCATCCCGGAACGC TTTAGCGGATCCAACAGCGGCAACACCGCGACCCTG ACCATTAGCGGCACTCAGGCGGAAGACGAAGCGGAT TATTATTGCCAGTCTTATGATTTTGGTAAGGTTGTG TTTGGCGGCGGCACGAAGTTAAC | 3ef2 |

Figure 3e

| SEQ ID NO | Antibody chain | Protein sequence | Fab code |
|---|---|---|---|
| 133 | VH1b | ELVQSGAEVKKPGASVKVSCKASGYTFTTNYM HWVRQAPGQGLEWMGIINPHNGSTSYAQKFQG RVTMTRDTSISTAYMELSSLRSEDTAVYYCAR GRYFLMDVWGQGTLVTVSS | 1aa1 |
| 134 | Vk1 | DIQMTQSPSSLSASVGDRVTITCRASQNILSY LNWYQQKPGKAPKLLIYAASSLQSGVPSRFSG SGSGTDFTLTISSLQPEDFAVYYCQQYGSVPT FGQGTKVEIKRT | 1aa1 |
| 135 | VH3 | ELVESGGGLVQPGGSLRLSCAASGFTFSNNAM NWVRQAPGKGLEWVSGISYDSSKTYYADSVKG RFTISRDNSKNTLYLQMNSLRAEDTAVYYCAR LTYTGAYRWGQGTLVTVSS | 1e4 |
| 136 | VL3 | DIELTQPPSVSVAPGQTARISCSGDNLGSYYV HWYQQKPGQAPVLVIYDDNNRPSGIPERFSGS NSGNTATLTISGTQAEDEADYYCQSYDFGKVV FGGGTKLTVL | 1e4 |
| 137 | VH3 | ELVESGGGLVQPGGSLRLSCAASGFTFSDYSI NWVRQAPGKGLEYVSNISYSGSSTYYADSVKG RFTISRDNSKNTLYLQMNSLRAEDTAVYYCAR FKYSGGSDSWGQGTLVTVSS | 3a4 |
| 138 | VL3 | DIELTQPPSVSVAPGQTARISCSGDNLPDFYV HWYQQKPGQAPVLVISEDNKRPSGIPERFSGS NSGNTATLTISGTQAEDEADYYCSTYGYTYSY SVFGGGTKL | 3a4 |
| 139 | VH3 | ELVESGGGLVQPGGSLRLSCAASGFTFSSYGI SWVRQAPGKGLEWVSGISYSGSSTYYADSVKG RFTISRDNSKNTLYLQMNSLRAEDTAVYYCAR LKPYRHKNGWFDYWGQGTLVTVSS | 3ab4 |
| 140 | Vk1 | DIQMTQSPSSLSASVGDRVTITCRASQNISNY LNWYQQKPGKAPKLLIHKVSNLQSGVPSRFSG SGSGTDFTLTISSLQPEDFAVYYCLQYDDFPR TFGQGTKVEIKRT | 3ab4 |
| 141 | VH3 | ELVESGGGLVQPGGSLRLSCAASGFTFSSYGI SWVRQAPGKGLEWVSSISYSGSNTYYADSVKG RFTISRDNSKNTLYLQMNSLRAEDTAVYYCAR MKPMRGYSGAVWGQGTLVTVSS | 3ah10 |
| 142 | Vk1 | DIQMTQSPSSLSASVGDRVTITCRASQDISNR LAWYQQKPGKAPKLLIYDANSLQSGVPSRFSG SGSGTDFTLTISSLQPEDFATYYCFQYSGPTF GQGTKVEIKRT | 3ah10 |

Figure 4a

| SEQ ID NO | Antibody chain | Protein sequence | Fab code |
|---|---|---|---|
| 143 | VH3 | ELVESGGGLVQPGGSLRLSCAASGFTFSNYGISWVRQAPGKGLEWVSAISYYGSNTYYADSVKGRFTISRDNSKNTLYLQMNSLRAEDTAVYYCARLKGGSGFVWGQGTLVTVSS | 3bb2 |
| 144 | Vk2 | DIVMTQSPLSLPVTPGEPASISCRSSQSLVYSNGNTTLSWYLQKPGQSPQLLIYGVSNRASGVPDRFSGSGSGTDFTLKISRVEAEDVGVYYCQQYNSFPRTFGQGTKVEIKRT | 3bb2 |
| 145 | VH3 | ELVESGGGLVQPGGSLRLSCAASGFTFSSYGMSWVRQAPGKGLEWVSGISSLGSTTYYADSVKGRFTISRDNSKNTLYLQMNSLRAEDTAVYYCARTGSPGTFMHGDHWGQGTLVTVSS | 3ee9 |
| 146 | Vk1 | DIQMTQSPSSLSASVGDRVTITCRASQDINNYLSWYQQKPGKAPKLLIYGASNLQSGVPSRFSGSGSGTDFTLTISSLQPEDFAVYYCQQYYGRPTTFGQGTKVEIKRT | 3ee9 |
| 147 | VH5 | ELVQSGAEVKKPGESLKISCKGSGYSFSKYWIGWVRQMPGKGLEWMGIIYPTDSYTRYSPSFQGQVTISADKSISTAYLQWSSLKASDTAMYYCARTHGYYKNGRMDVWGQGTLVTVSS | 5a6 |
| 148 | Vk2 | DIVMTQSPLSLPVTPGEPASISCRSSQSLVHSNGYNYLSWYLQKPGQSPQLLIYLGSNRASGVPDRFSGSGSGTDFTLKISRVEAEDVGVYYCHQYGDFSDTFGQGTKVEIKRT | 5a6 |
| 149 | VH5 | ELVQSGAEVKKPGESLKISCKGSGYSFTGYISWVRQAPGKGLEWMGIIYPGDSYTNYSPSFQGQVTISADKSISTAYLQWSSLKASDTAMYYCARYSGPNWDVMDSWGQGTLVTVSS | 5aa3 |
| 150 | VL1 | DIVLTQPPSVSGAPGQRVTISCSGSSSNIGSYYVNWYQQLPGTAPKLLIYADDKRPSGVPDRFSGSKSGTSASLAITGLQSEDEADYYCQSYDSTKDDSVFGGGTKL | 5aa3 |
| 151 | VH3 | ELVESGGGLVQPGGSLRLSCAASGFTFSSYGMHWVRQAPGKGLEYVSAISYSSSSTSYADSVKGRFTISRDNSKNTLYLQMNSLRAEDTAVYYCARLSYTGFAVWGQGTLVTVSS | 3ef2 |

Figure 4b

| SEQ ID NO | Antibody chain | Protein sequence | Fab code |
|---|---|---|---|
| 152 | VL3 | DIELTQPPSVSVAPGQTARISC<u>SGDNLGSYYV</u><br><u>H</u>WYQQKPGQAPVL<u>VIYDDNNRPSG</u>IPERFSGS<br>NSGNTATLTISGTQAEDEADYYC<u>QSYDFGKVV</u><br>FGGGTKL | 3ef2 |

Figure 4c

| Anti-body | Form of anti-body used | ELISA Binding to purified human MN expressed in HKB-11 cells | ELISA Binding to purified human MN expressed in Sf9 cells | Binding affinity for purified human MN expressed in HKB-11 cells Kd (M) |
|---|---|---|---|---|
| 1aa1 | Pure Fab | Positive | Positive | $1.5 \times 10{-10}$ |
| 1aa1 | Pure IgG1 | Positive | ND | $4.9 \times 10{-8}$ |
| 1e4 | Pure Fab | Positive | ND | $1.4 \times 10{-9}$ |
| 1e4 | Pure IgG1 | Positive | ND | $1.0 \times 10{-9}$ |
| 3a4 |  | Positive | Positive |  |
| 3ab4 | Pure Fab | Positive | Positive | $5.0 \times 10{-8}$ |
| 3ah10 | Pure Fab | Positive | ND | $1.6 \times 10{-8}$ |
| 3bb2 | Pure Fab | Positive | ND | $2.7 \times 10{-8}$ |
| 3ee9 | Crude Fab | Positive | Positive | $1.6 \times 10{-8}$ |
| 3ee9 | Pure IgG1 | Positive | ND | $5.9 \times 10{-9}$ |
| 5a6 | Crude Fab | Positive | Positive | $3.4 \times 10{-9}$ |
| 5aa3 | Crude Fab | Positive | Positive | $2.5 \times 10{-8}$ |
| 3ef2 | Crude Fab | Positive | Positive | $4.1 \times 10{-9}$ |

ND = not determined

Figure 5

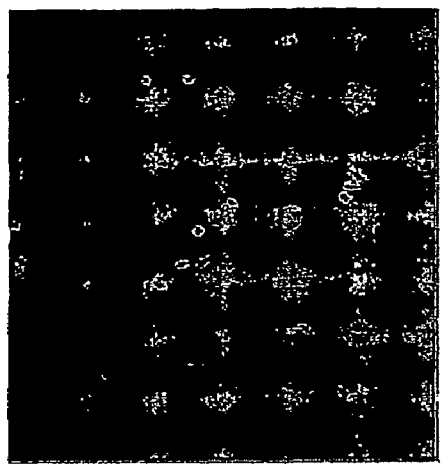 Anti-MN Mab 1e4
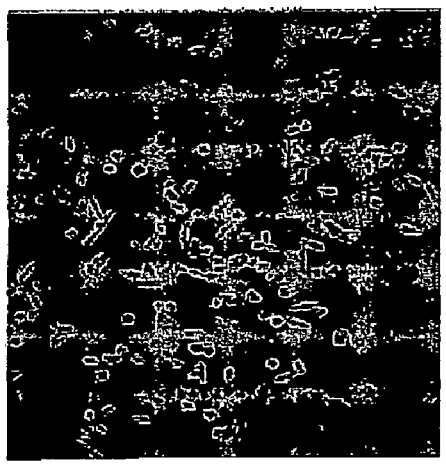 Control IgG
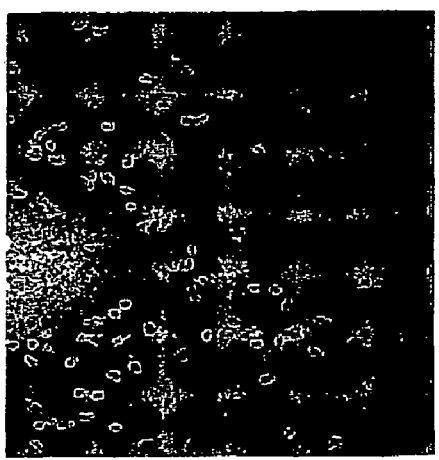 Buffer vehicle
Figure 6

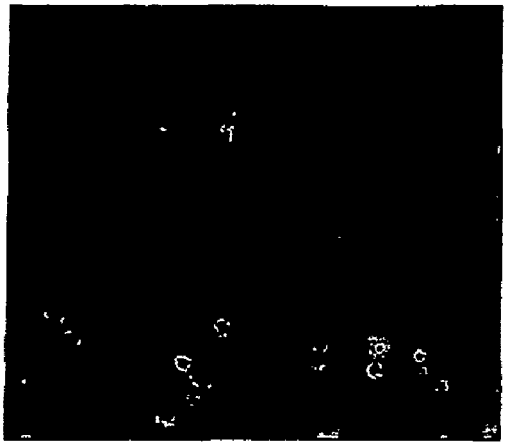 
Figure 11b

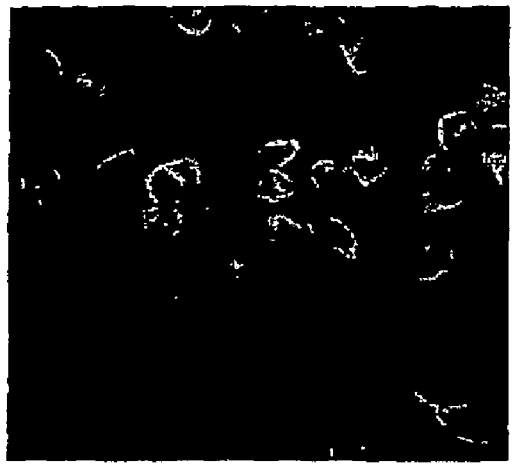
(MN+) PC3MM2 Untreated
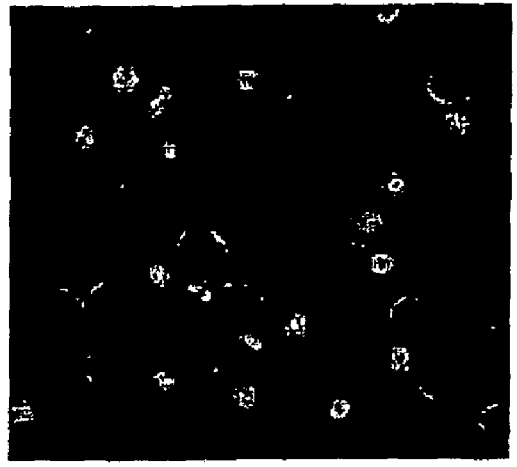
PC3MM2 with 3eep-MMAE
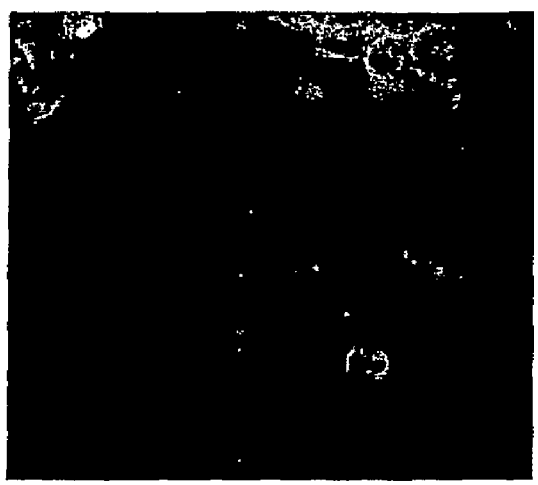
(MN-) H460 Untreated
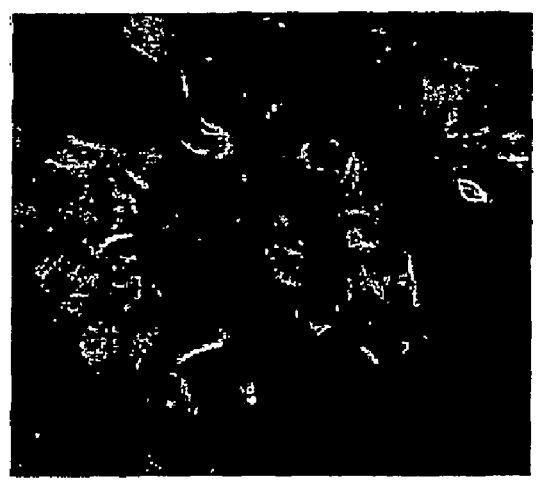
H460 with 3ee9-MMAE
Figure 14

```
AATTGGAGGCTACAGTCAGTGGAGAGGACTTTCACTGACTGACTGACTGCGTCTCAACCT
GGGGACAAGTTTGTACAAAAAAGCAGGCTCTGTCTAGAGGGCACCATGGTGTTGCAGACC
CAGGTCTTCATTTCTCTGTTGCTCTGGATCTCTGGTGCCTACGGGATATCCAGATGACC
CAGAGCCCGTCTAGCCTGAGCGCGAGCGTGGGTGATCGTGTGACCATTACCTGCAGAGCG
AGCCAGGATATTAATAATTATCTGTCTTGGTACCAGCAGAAACCAGGTAAAGCACCGAAA
CTATTAATTTATGGTGCTTCTAATTTGCAAAGCGGGGTCCCGTCCCGTTTTAGCGGCTCT
GGATCCGGCACTGATTTTACCCTGACCATTAGCAGCCTGCAACCTGAAGACTTTGCGGTT
TATTATTGCCAGCAGTATTATGGTCGTCCTACTACCTTTGGCCAGGGTACGAAAGTTGAA
ATTAAACGTACGGTGGCTGCACCATCTGTCTTCATCTTCCCGCCATCTGATGAGCAGTTG
AAATCTGGAACTGCCTCTGTTGTGTGCCTGCTGAATAACTTCTATCCCAGAGAGGCCAAA
GTACAGTGGAAGGTGGATAACGCCCTCCAATCGGGTAACTCCCAGGAGAGTGTCACAGAG
CAGGACAGCAAGGACAGCACCTACAGCCTCAGCAGCACCCTGACGCTGTCTAAAGCAGAC
TACGAGAAACACAAAGTCTACGCCTGCGAAGTCACCCATCAGGGCCTGAGCTCGCCCGTC
ACAAAGAGCTTCAACAGGGGAGAGTGTTAGGCGGCCGCGCCTCGACTGTGCCTTCTAGTT
GCCAGCCATCTGTTGTTTGCCCCTCCCCGTGCCTTCCTTGACCCTGGAAGGTGCCACTC
CCACTGTCCTTTCCTAATAAAATGAGGAAATTGCATCGCATTGTCTGAGTAGGTGTCATT
CTATTCTGGGGGGTGGGGTGGGGCAGGACAGCAAGGGGGAGGATTGGGAAGACAATAGCA
GGCATGCTGGGGATGCGGTGGGCTCTATGGGATGCTTATCGCCACGTTCGGCGCGCCGTC
GACGATGTACGGGCCAGATATACGCGTTGACATTGATTATTGACTAGTTATTAATAGTAA
TCAATTACGGGGTCATTAGTTCATAGCCCATATATGGAGTTCCGCGTTACATAACTTACG
GTAAATGGCCCGCCTGGCTGACCGCCCAACGACCCCCGCCCATTGACGTCAATAATGACG
TATGTTCCCATAGTAACGCCAATAGGGACTTTCCATTGACGTCAATGGGTGGACTATTTA
CGGTAAACTGCCCACTTGGCAGTACATCAAGTGTATCATATGCCAAGTACGCCCCCTATT
GACGTCAATGACGGTAAATGGCCCGCCTGGCATTATGCCCAGTACATGACCTTATGGGAC
TTTCCTACTTGGCAGTACATCTACGTATTAGTCATCGCTATTACCATGGTGATGCGGTTT
TGGCAGTACATCAATGGGCGTGGATAGCGGTTTGACTCACGGGGATTTCCAAGTCTCCAC
CCCATTGACGTCAATGGGAGTTTGTTTTGGCACCAAAATCAACGGGACTTTCCAAAATGT
CGTAACAACTCCGCCCCATTGACGCAAATGGGCGGTAGGCGTGTACGGTGGGAGGTCTAT
```

Figure 29a

```
ATAAGCAGAGCTCTCTGGCTAACTAGAGAACCCACTGCTTACTGGCTTATCGAAATTAAT
ACGACTCACTATAGGGAGACCCAAGCTGGCTAGCGCCACCATGAAACACCTGTGGTTCTT
CCTCCTGCTGGTGGCAGCTCCCAGATGGGTCCTGTCCCAGGTGGAATTGGTGGAAAGCGG
```

CGGCGGCCTGGTGCAACCGGGCGGCAGCCTGCGTCTGAGCTGCGCGGCCTCCGGATTTAC
CTTTTCTTCTTATGGTATGTCTTGGGTGCGCCAAGCCCCTGGGAAGGGTCTCGAGTGGGT
GAGCGGTATCTCTTCTCTTGGTAGCACTACCTATTATGCGGATAGCGTGAAAGGCCGTTT
TACCATTTCACGTGATAATTCGAAAAACACCCTGTATCTGCAAATGAACAGCCTGCGTGC
GGAAGATACGGCCGTGTATTATTGCGCGCGTACTGGTTCTCCTGGTACTTTTATGCATGG
TGATCATTGGGGCCAAGGCACCCTGGTGACGGTTAGCTCAGCCTCCACCAAGGGTCCATC
GGTCTTCCCCCTGGCACCCTCCTCCAAGAGCACCTCTGGGGGCACAGCGGCCCTGGGCTG
CCTGGTCAAGGACTACTTCCCCGAACCGGTGACGGTGTCGTGGAACTCAGGCGCCCTGAC
CAGCGGCGTGCACACCTTCCCGGCTGTCCTACAGTCCTCAGGACTCTACTCCCTCAGCAG
CGTGGTGACCGTGCCCTCCAGCAGCTTGGGCACCCAGACCTACATCTGCAACGTGAATCA
CAAGCCCAGCAACACCAAGGTGGACAAGAAAGTTGAGCCCAAATCTTGTGACAAAACTCA
CACATGCCCACCGTGCCCAGCACCTGAACTCCTGGGGGGACCGTCAGTCTTCCTCTTCCC
CCCAAAACCCAAGGACACCCTCATGATCTCCCGGACCCCTGAGGTCACATGCGTGGTGGT
GGACGTGAGCCACGAAGACCCTGAGGTCAAGTTCAACTGGTACGTGGACGGCGTGGAGGT
GCATAATGCCAAGACAAAGCCGCGGGAGGAGCAGTACAACAGCACGTACCGGGTGGTCAG
CGTCCTCACCGTCCTGCACCAGGACTGGCTGAATGGCAAGGAGTACAAGTGCAAGGTCTC
CAACAAAGCCCTCCCAGCCCCCATCGAGAAAACCATCTCCAAAGCCAAAGGGCAGCCCCG
AGAACCACAGGTGTACACCCTGCCCCCATCCCGGGATGAGCTGACCAAGAACCAGGTCAG
CCTGACCTGCCTGGTCAAAGGCTTCTATCCCAGCGACATCGCCGTGGAGTGGGAGAGCAA
TGGGCAGCCGGAGAACAACTACAAGACCACGCCTCCCGTGCTGGACTCCGACGGCTCCTT
CTTCCTCTACAGCAAGCTCACCGTGGACAAGAGCAGGTGGCAGCAGGGGAACGTCTTCTC
ATGCTCCGTGATGCATGAGGCTCTGCACAACCACTACACGCAGAAGAGCCTCTCCCTGTC
TCCGGGTAAATGAGGGCCCGTTTAAACCCGCTGATCAGCCTCGACTGTGCCTTCTAGTTG
CCAGCCATCTGTTGTTTGCCCCTCCCCCGTGCCTTCCTTGACCCTGGAAGGTGCCACTCC
CACTGTCCTTTCCTAATAAAATGAGGAAATTGCATCGCATTGTCTGAGTAGGTGTCATTC
TATTCTGGGGGGTGGGGTGGGGCAGGACAGCAAGGGGGAGGATTGGGAAGACAATA

Figure 29b

GCAGGCATGCTGGGGATGCGGTGGGCTCTATGGCTTCTGAGGCGGAAAGAACCAGCCTCA
CGTGGACCCAGCTTTCTTGTACAAAGTGGTCCCCCTACAGAGACGACTGACTGACTGACT
GGAAAGAGGAAGGGCTGGAAGAGGAAGGAGCTTGGCGTAATCATGGTCATAGCTGTTTCC
TGTGTGAAATTGTTATCCGCTCACAATTCCACACAACATACGAGCCGGAAGCATAAAGTG
TAAAGCCTGGGGTGCCTAATGAGTGAGCTAACTCACATTAATTGCGTTGCGCTCACTGCC
CGCTTTCCAGTCGGGAAACCTGTCGTGCCAGCTGCATTAATGAATCGGCCAACGCGCGGG

```
GAGAGGCGGTTTGCGTATTGGGCGCTCTTCCGCTTCCTCGCTCACTGACTCGCTGCGCTC
GGTCGTTCGGCTGCGGCGAGCGGTATCAGCTCACTCAAAGGCGGTAATACGGTTATCCAC
AGAATCAGGGGATAACGCAGGAAAGAACATGTGAGCAAAAGGCCAGCAAAAGGCCAGGAA
CCGTAAAAAGGCCGCGTTGCTGGCGTTTTTCCATAGGCTCCGCCCCCTGACGAGCATCA
CAAAAATCGACGCTCAAGTCAGAGGTGGCGAAACCCGACAGGACTATAAAGATACCAGGC
GTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTA
TCTCAGTTCGGTGTAGGTCGTTCGCTCCAAGCTGGGCTGTGTGCACGAACCCCCCGTTCA
GCCCGACCGCTGCGCCTTATCCGGTAACTATCGTCTTGAGTCCAACCCGGTAAGACACGA
CTTATCGCCACTGGCAGCAGCCACTGGTAACAGGATTAGCAGAGCGAGGTATGTAGGCGG
TGCTACAGAGTTCTTGAAGTGGTGGCCTAACTACGGCTACACTAGAAGGACAGTATTTGG
TATCTGCGCTCTGCTGAAGCCAGTTACCTTCGGAAAAGAGTTGGTAGCTCTTGATCCGG
CAAACAAACCACCGCTGGTAGCGGTGGTTTTTTTGTTTGCAAGCAGCAGATTACGCGCAG
AAAAAAAGGATCTCAAGAAGATCCTTTGATCTTTTCTACGGGGTCTGACGCTCAGTGGAA
CGAAAACTCACGTTAAGGGATTTTGGTCATGAGATTATCAAAAAGGATCTTCACCTAGAT
CCTTTTAAATTAAAAATGAAGTTTTAAATCAATCTAAAGTATATATGAGTAAACTTGGTC
TGACAGTTACCAATGCTTAATCAGTGAGGCACCTATCTCAGCGATCTGTCTATTTCGTTC
ATCCATAGTTGCCTGACTCCCCGTCGTGTAGATAACTACGATACGGGAGGGCTTACCATC
TGGCCCCAGTGCTGCAATGATACCGCGAGACCCACGCTCACCGGCTCCAGATTTATCAGC
AATAAACCAGCCAGCCGGAAGGGCCGAGCGCAGAAGTGGTCCTGCAACTTTATCCGCCTC
CATCCAGTCTATTAATTGTTGCCGGGAAGCTAGAGTAAGTAGTTCGCCAGTTAATAGTTT
GCGCAACGTTGTTGCCATTGCTACAGGCATCGTGGTGTCACGCTCGTCGTTTGGTATGGC
TTCATTCAGCTCCGGTTCCCAACGATCAAGGCGAGTTACATGATCCCCCATGTTGT
```

Figure 29c

```
GCAAAAAGCGGTTAGCTCCTTCGGTCCTCCGATCGTTGTCAGAAGTAAGTTGGCCGCAG
TGTTATCACTCATGGTTATGGCAGCACTGCATAATTCTCTTACTGTCATGCCATCCGTAA
GATGCTTTTCTGTGACTGGTGAGTACTCAACCAAGTCATTCTGAGAATAGTGTATGCGGC
GACCGAGTTGCTCTTGCCCGGCGTCAATACGGGATAATACCGCGCCACATAGCAGAACTT
TAAAAGTGCTCATCATTGGAAAACGTTCTTCGGGGCGAAAACTCTCAAGGATCTTACCGC
TGTTGAGATCCAGTTCGATGTAACCCACTCGTGCACCCAACTGATCTTCAGCATCTTTTA
CTTTCACCAGCGTTTCTGGGTGAGCAAAAACAGGAAGGCAAAATGCCGCAAAAAAGGGAA
TAAGGGCGACACGGAAATGTTGAATACTCATACTCTTCCTTTTTCAATATTATTGAAGCA
TTTATCAGGGTTATTGTCTCATGAGCGGATACATATTTGAATGTATTTAGAAAAATAAAC
```

```
AAATAGGGGTTCCGCGCACATTTCCCCGAAAAGTGCCACCTGACGTCTAAGAAACCATTA
TTATCATGACATTAACCTATAAAAATAGGCGTATCACGAGGCCCTTTCGTCTCGCGCGTT
TCGGTGATGACGGTGAAAACCTCTGACACATGCAGCTCCCGGAGACGGTCACAGCTTGTC
TGTAAGCGGATGCCGGGAGCAGACAAGCCCGTCAGGGCGCGTCAGCGGGTGTTGGCGGGT
GTCGGGGCTGGCTTAACTATGCGGCATCAGAGCAGATTGTACTGAGAGTGCACCATAAAA
TTGTAAACGTTAATATTTTGTTAAAATTCGCGTTAAATTTTTGTTAAATCAGCTCATTTT
TTAACCAATAGGCCGAAATCGGCAAAATCCCTTATAAATCAAAAGAATAGCCCGAGATAG
GGTTGAGTGTTGTTCCAGTTTGGAACAAGAGTCCACTATTAAAGAACGTGGACTCCAACG
TCAAAGGGCGAAAAACCGTCTATCAGGGCGATGGCCCACTACGTGAACCATCACCCAAAT
CAAGTTTTTTGGGGTCGAGGTGCCGTAAAGCACTAAATCGGAACCCTAAAGGGAGCCCCC
GATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACAC
CCGCCGCGCTTAATGCGCCGCTACAGGGCGCGTACTATGGTTGCTTTGACGTATGCGGTG
TGAAATACCGCACAGATGCGTAAGGAGAAAATACCGCATCAGGCGCCATTCGCCATTCAG
GCTGCGCAACTGTTGGGAAGGGCGATCGGTGCGGGCCTCTTCGCTATTACGCCAGCTGGC
GAAAGGGGGATGTGCTGCAAGGCGATTAAGTTGGGTAACGCCAGGGTTTTCCCAGTCACG
ACGTTGTAAAACGACGGCCAGTG    [SEQ ID NO: 153]
```

Figure 29d

ANTI-MN ANTIBODIES AND METHODS OF USING SAME

RELATED APPLICATIONS/PATENTS AND INCORPORATION BY REFERENCE

This application is a National Stage Application filed under 35 U.S.C. §371 based on International Application No. PCT/US2006/047445, filed Dec. 12, 2006, which claims priority to U.S. Provisional Application Ser. No. 60/749,716 filed Dec. 12, 2005, the entire contents each of which are incorporated herein by reference.

The foregoing application, and all documents cited therein and all documents cited or referenced therein, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated by reference, and may be employed in the practice of the invention.

BACKGROUND OF THE INVENTION

1. Field of the Invention

The present invention relates to antibodies and/or fragments thereof having specificity for MN protein. The invention further relates to antibody and/or immunoconjugate compositions and their use in treating, preventing, and/or diagnosing MN-related disorders, e.g. cancer.

2. Background

The occurrence of cancer is most commonly associated with aging whereby 65% of all new cases of cancer are recorded for patients aged 65 and over. Cancer is the second leading cause of death in the United States, exceeded only by heart disease. Indeed, the American Cancer Society has estimated that 1 in 4 people will die from cancer in the U.S., assuming current mortality rates remain static. In the U.S. alone, 1,399,790 new cases and 564,830 deaths from cancer are expected in 2006. The majority of these new cases are expected to be cancers of the colon (106,680), lung (172,570) and breast (214,640). Moreover, both the incidence and prevalence of cancer is predicted to increase approximately 15% over the next ten years, reflecting an average growth rate of 1.4% (American Cancer Society, 2006).

One recently identified tumor associated antigen, MN, a cell surface protein, has been found to be expressed in a number of clinical carcinomas. For example, MN has been found to be ectopically expressed in 100% of renal cell carcinomas (Liao, S Y, Cancer Res., 1997, 57:2827-2831), 100% of carcinomas of the esophagus (Turner J R, Hum. Pathol., 199, 28:740-744), greater than 90% of cervical carcinomas (Liao, S Y, Cancer Res., 1997, 57:2827-2831), 76% of malignant colon carcinomas (Saarnio, J. et al., Am. J. Path., 1997, 153:279-285), 80% of non-small cell lung carcinomas (Vermylen P. et al., Eur. Respir. J., 1999, 14:806-811), and in 48% of breast cancers (Chia S K et al., J. Clin. Oncol., 2001, 19:3660-3668). Like other tumor associated antigens, the MN protein is also present on cells of a limited number of normal tissues, including, for example, stomach, bile duct mucosa and the highly proliferate normal cells located in the small intestine (Saarnio J. et al., J. Histochem. Cytochem, 1998, 46:497-504).

Human MN cDNA has been cloned and sequenced (Pastorek, et al., Oncogene, 1994, 9:2877-2888). The predicted protein consists of a signal peptide, a proteoglycan-related sequence, a carbonic anhydrase domain (carbonic anhydrase 1x or CA IX), a transmembrane segment, and a short intracellular tail. The carbonic anhydrase IX domain catalyzes the reversible hydration of carbon dioxide to carbonic acid. This activity may have a role in regulating the local acidification of the extracellular portion of the tumor environments, which may consequently lead to the activation of proteases and finally, metastasis.

The regulation of MN expression has also been investigated. In one aspect, for example, MN expression is up-regulated by hypoxia. The transcriptional complex known as hypoxia-inducible factor-1 (HIF-1) is a regulator of MN expression. Accordingly, MN is known as a HIF-1 responsive gene which has implications in the understanding of tumor response to hypoxia (Wykoff C C et al., Cancer Res., 2000, 60:7075-7083). Furthermore, MN expression correlates with tumor hypoxia levels and is a prognostic indicator of overall survival and metastasis-free survival in cervical cancer (Loncaster, J A et al., Cancer Res., 2000, 60:7075-7083). MN expression also correlates with a high mean vessel density, advanced cancer stage, degree of necrosis in head and neck carcinoma (Beasley N J P et al., Cancer Res., 2001, 61:5262-5267), poor survival in nasopharyngeal carcinoma (Hui E P et al., Clin. Cancer Res., 2002, 8:2595-2604), tumor necrosis, higher grade, negative estrogen receptor status, higher relapse rate, and poor survival for invasive breast carcinoma (Chia S K et al., J. Clin. Oncol., 2001, 19:3660-3668). Therefore expression of MN antigen is correlates with poor survival prognosis, and cancers of higher grade.

New and improved therapies for these aggressive cancers, in particular, those that target MN expression, are highly desirable and would represent an advancement in the art. As such, the present invention discloses new antibody compositions and immunoconjugates thereof that are useful in the treatment, prevention and/or diagnosis of MN-related cancers.

SUMMARY OF THE INVENTION

The present invention relates to antibodies, e.g., monoclonal antibodies, or antibody fragments that bind to the cell-surface protein MN and which can be used in the treatment, prevention and/or diagnosis of cancer. The antibodies of the invention can further be conjugated to cytotoxic agents, e.g., monomethylauristatin-E, and/or co-administered or formulated with one or more additional anti-cancer agents. The anti-MN antibodies and immunoconjugates of the invention can be used in the methods of the invention to treat and/or diagnose and/or monitor cancers, e.g. solid tumors.

In one aspect, the present invention provides an antibody or antibody fragment, or a composition that includes the antibody or antibody fragment, wherein the antibody or fragment has an antigenic binding site that is specifically directed against an MN protein. The antigenic binding site may include at least one CDR1, CDR2, or CDR3, or a CDR1 together with a CDR2 or a CDR3, or a CDR2 together with a CDR 1 or a CDR3, or a CDR3 together with a CDR1 or CDR 2, or any combination thereof. The CDR1 can be selected from the group consisting of SEQ ID NOS: 57, 58, 59, 60, 61, 62, 77, 80, 81, 86, 87, 88, 89, 98, 99, 104, 107, and 108. The CDR2 can be selected from the group consisting of SEQ ID NOS: 63, 64, 65, 66, 67, 68, 69, 78, 82, 83, 90, 91, 92, 93, 100, 101, 105, 109, and 110. The CDR3 can selected from the group consisting of SEQ ID NOS: 70, 71, 72, 73, 74, 75, 76, 79, 84, 85, 94, 95, 96, 97, 102, 103, 106, 111, and 112. The CDR sequences of this aspect of the invention can also include amino acid sequences that have preferably greater than about 80% sequence identity, more preferably greater than about 85% sequence identity, even more preferably about 90% sequence identity, still more preferably about 95% or even about 99% sequence identity, and even up to about 100% sequence identity to any of the above sequences indicated for each of CDR1, CDR2 or CDR3.

In another aspect, the antigenic binding site can have a heavy chain variable region CDR that is selected from the group consisting of: SEQ ID NOS: 57-85 and an amino acid sequence having greater than about 80% sequence identity to any of SEQ ID NOS: 57-85.

The antigenic binding site can also have a light chain variable region CDR selected from the group consisting of: SEQ ID NOS: 86-112 and an amino acid sequence having greater than about 80% sequence identity to any of SEQ ID NOS: 86-112.

The antigenic binding site can also be selected from a set of specific CDR sequences that include the following sets of six CDRs:
  (a) [3ee9] SEQ ID NOS: 57, 63, 70, 89, 93, and 97;
  (b) [3ef2] SEQ ID NOS: 58, 64, 71, 107, 109, and 111;
  (c) [1e4] SEQ ID NOS: 59, 65, 72, 107, 109, and 111;
  (d) [3a4] SEQ ID NOS: 60, 66, 73, 108, 110, and 112;
  (e) [3ab4] SEQ ID NOS: 61, 67, 74, 87, 91, and 95;
  (f) [3ah10] SEQ ID NOS: 61, 68, 75, 88, 92, and 96;
  (g) [3bb2] SEQ ID NOS: 62, 69, 76, 98, 100, and 102;
  (h) [1aa1] SEQ ID NOS: 77, 78, 79, 86, 90, and 94;
  (i) [5a6] SEQ ID NOS: 80, 82, 84, 99, 101, and 103; and
  (j) [5aa3] SEQ ID NOS: 81, 83, 85, 104, 105, and 106.

The antigenic binding site may also include a set of heavy chain CDR sequences selected from the group consisting of:
  (a) [3ee9] SEQ ID NOS: 57, 63, and 70;
  (b) [3ef2] SEQ ID NOS: 58, 64, and 71;
  (c) [1e4] SEQ ID NOS: 59, 65, and 72;
  (d) [3a4] SEQ ID NOS: 60, 66, and 73;
  (e) [3ab4] SEQ ID NOS: 61, 67, and 74;
  (f) [3ah10] SEQ ID NOS: 61, 68, and 75;
  (g) [3bb2] SEQ ID NOS: 62, 69, and 76;
  (h) [1aa1] SEQ ID NOS: 77, 78, and 79;
  (i) [5a6] SEQ ID NOS: 80, 82, and 84; and
  (j) [5aa3] SEQ ID NOS: 81, 83, and 85.

The antigenic binding site can also include a set of light chain CDR sequences selected from the group consisting of:
  (a) [3ee9] SEQ ID NOS: 89, 93, and 97;
  (b) [3ef2] SEQ ID NOS: 107, 109, and 111;
  (c) [1e4] SEQ ID NOS: 107, 109, and 111;
  (d) [3a4] SEQ ID NOS: 108, 110, and 112;
  (e) [3ab4] SEQ ID NOS: 87, 91, and 95;
  (f) [3ah10] SEQ ID NOS: 88, 92, and 96;
  (g) [3bb2] SEQ ID NOS: 98, 100, and 102;
  (h) [1aa1] SEQ ID NOS: 86, 90, and 94;
  (i) [5a6] SEQ ID NOS: 99, 101, and 103; and
  (j) [5aa3] SEQ ID NOS: 104, 105, and 106.

In yet another aspect, the present invention provides an antibody or antibody fragment that has an antigenic binding site that contains a pair of heavy chain variable and light chain variable regions selected from the group consisting of:
  (a) the heavy chain variable region of SEQ ID NO:133 and the light chain variable region of SEQ ID NO:134;
  (b) the heavy chain variable region of SEQ ID NO:135 and the light chain variable region of SEQ ID NO:136;
  (c) the heavy chain variable region of SEQ ID NO:137 and the light chain variable region of SEQ JD NO:138;
  (d) the heavy chain variable region of SEQ ID NO:139 and the light chain variable region of SEQ ID NO:140;
  (e) the heavy chain variable region of SEQ ID NO:141 and the light chain variable region of SEQ ID NO:142;
  (f) the heavy chain variable region of SEQ ID NO:143 and the light chain variable region of SEQ ID NO:144;
  (g) the heavy chain variable region of SEQ ID NO:145 and the light chain variable region of SEQ ID NO:146;
  (h) the heavy chain variable region of SEQ ID NO:147 and the light chain variable region of SEQ ID NO:148;
  (i) the heavy chain variable region of SEQ ID NO:149 and the light chain variable region of SEQ ID NO:150; and
  (j) the heavy chain variable region of SEQ ID NO:151 and the light chain variable region of SEQ ID NO:152.

The antibodies or antibody fragments of the invention can bind to the MN protein with a dissociation constant of preferably about 0.15 nM to about 50 nM.

In another aspect, the antibodies or fragments of the invention are IgG antibodies or IgG fragments. The antibodies or fragments can also be IgG1, IgG2a, IgG2b, IgG3, IgM, IgD, IgE, IgA, or IgM antibodies, Fab fragments, F(ab')$_2$ fragments, scFv fragments, Fv fragments, a diabodies, linear antibodies, single-chain antibodies, biospecific antibodies, multispecific antibodies, or chimeric antibodies (e.g. comprising a human antibody scaffold grafted to a human or non-human antibody binding region, or a non-human antibody scaffold grafted to a human or non-human antibody binding region). The chimeric antibodies can include, for example, antibody scaffold regions from non-human sources, such as, for example, cow, mouse, llama, camel, or rabbit. Further information on the engineering of antibodies can be found in the literature, for example, Holliger and Hudson, Nature Biotechnology, (September 2005) 23:1126-1136, which is incorporated herein by reference. The aforementioned fragments can be obtained from an immunoglobulin or produced by a suitable means, e.g. recombinant expression, in a fragment form.

The antibodies or antibody fragments of the invention can also be humanized, wherein the CDR sequences or regions (e.g. CDR1, CDR2, CDR3) can be non-human, e.g. murine.

The antibodies or antibody fragments of the invention, or compositions including the antibodies or fragments, can include a cytoxic agent that is conjugated to the antibody or fragment. In one aspect, the cytotoxic agent is monomethyl-lauristatin-E (MMAE), however, other cytoxic agents are also provided, which can include, for example, functional analogs of MMAE (e.g. monomethylauristatin-F), and other cytotoxic agents, e.g., aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-1 1), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, Pseudomonas exotoxin, and Pseudomonas endotoxin, or combinations thereof. Any of the cytoxic agents can also include functional analogs thereof.

The compositions of the invention can include in addition to the antibodies and fragments (with or without the aforementioned conjugated cytoxic agents) various anti-cancer agents, which can include, for example, bleomycin, docetaxel (Taxotere), doxorubicin, edatrexate, erlotinib (Tarceva), etoposide, finasteride (Proscar), flutamide (Eulexin), gemcitabine (Gemzar), genitinib (Irresa), goserelin acetate (Zoladex), granisetron (Kytril), imatinib (Gleevec), irinotecan (Campto/Camptosar), ondansetron (Zofran), paclitaxel (Taxol), pegaspargase (Oncaspar), pilocarpine hydrochloride (Salagen), porfimer sodium (Photofrin), interleukin-2 (Proleukin), rituximab (Rituxan), topotecan (Hycamtin), trastuzumab (Herceptin), Triapine, vincristine, and vinorelbine tartrate (Navelbine), or therapeutic antibodies or fragments thereof, or antiangiogenic agent, such as, for example, angiostatin, bevacizumab (Avastin®), sorafenib (Nexavar®), baculostatin, canstatin, maspin, anti-VEGF antibodies or peptides, anti-placental growth factor antibodies or peptides, anti-Flk-1 antibodies, anti-Flt-1 antibodies or peptides, laminin peptides, fibronectin peptides, plasminogen activator inhibitors, tissue metalloproteinase inhibitors, interferons, interleukin 12, IP-10, Gro-β, thrombospondin, 2-methoxyoestradiol, proliferin-related protein, carboxiamidotriazole, CM101, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, accutin, cidofovir, vincristine, bleomycin, AGM-1470, platelet factor 4 or minocycline.

The present invention further provides in another aspect a method for treating an MN-related disorder by administering a therapeutically effective amount of the antibodies and/or fragments of the invention, or the compositions of the invention which include the antibodies and/or fragments of the invention. The MN-related disorder can include, for example, cancer, such as, a solid tumor cancer. The solid tumor can be in or originating from the breast, respiratory tract, lung, brain, reproductive organ, digestive tract, colon, urinary tract, kidney, esophagus, cervix, eye, liver, skin, head, neck, thyroid, and parathyroid.

In another aspect, the present invention provides a method of diagnosing an MN-related disorder characterized abnormal MN levels comprising comparing the level of MN in a suspected diseased tissue or cell with the level of MN in a corresponding healthy tissue or cell, wherein an abnormal MN level in the suspected diseased tissue or cell is an indication of an MN-related disorder, said step of comparing further comprising detecting by immunoassay the level of MN in the diseased tissue and the healthy tissue with the antibodies or antibody fragments of the invention.

In a particular aspect, the invention provides a method of diagnosing an MN-related disorder where the immunoassay includes the steps of: (a) detecting the level of MN protein in the healthy tissue; (b) detecting the level of MN protein in the suspected diseased tissue; and (c) comparing the levels of MN protein from (a) and (b). An elevated level of MN protein in the suspected diseased tissue as compared to the level of MN protein in the healthy tissue is indicative of the presence of an MN-related disorder.

Also provided by the present invention is a kit comprising the antibodies or antibody fragments of the invention, or alternatively, the compositions of the invention, and a set of instructions for using the kit in a method of treating an MN-related disorder or for diagnosing a an MN-related disorder.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1a-d depicts DNA sequences of the antibody complementarity determining regions (CDRs);

FIG. 2a-c depicts the protein sequences of the antibody complementarity determining regions (CDRs);

FIG. 3a-e depicts the DNA sequences of specific antibody light and heavy chain to variable regions, each of which contains both CDRs and framework regions;

FIG. 4a-c depicts protein sequences of specific antibody light (VL) and heavy (VH) chain variable regions, each of which contains both the CDRs and the framework regions;

FIG. 5 depicts the MN-binding properties for the MN antibodies of the present invention;

FIG. 6 depicts the prevention of tumor cell adhesion to MN coated plates produced by incubation with an anti-MN antibody;

FIG. 11b shows immunofluorescence images depicting internalization of the 1E4 immunoconjugate by MN+ cells and lack of internalization by MN− cells. Internalized 1E4 immunoconjugate is shown as fluorescence;

FIG. 14 shows immunofluorescence images depicting 3ee9/MMAE's prevention of normal spindle formation by tubulin inhibition;

FIG. 29a-d shows the complete nucleotide sequence of the insert region of the mammalian expression vector 3ee9$_{H+L}$pCMV$_{UCOE}$8 (see Example 21) which encodes a human IgG anti-MN antibody comprising the kappa and heavy CDR variable regions of SEQ ID NOS: 126 and 125, respectively, obtained from vector 3ee9pMORPHx9 (see Examples 1-3). SEQ ID NO: 153.

DETAILED DESCRIPTION OF THE INVENTION

Figure 7:
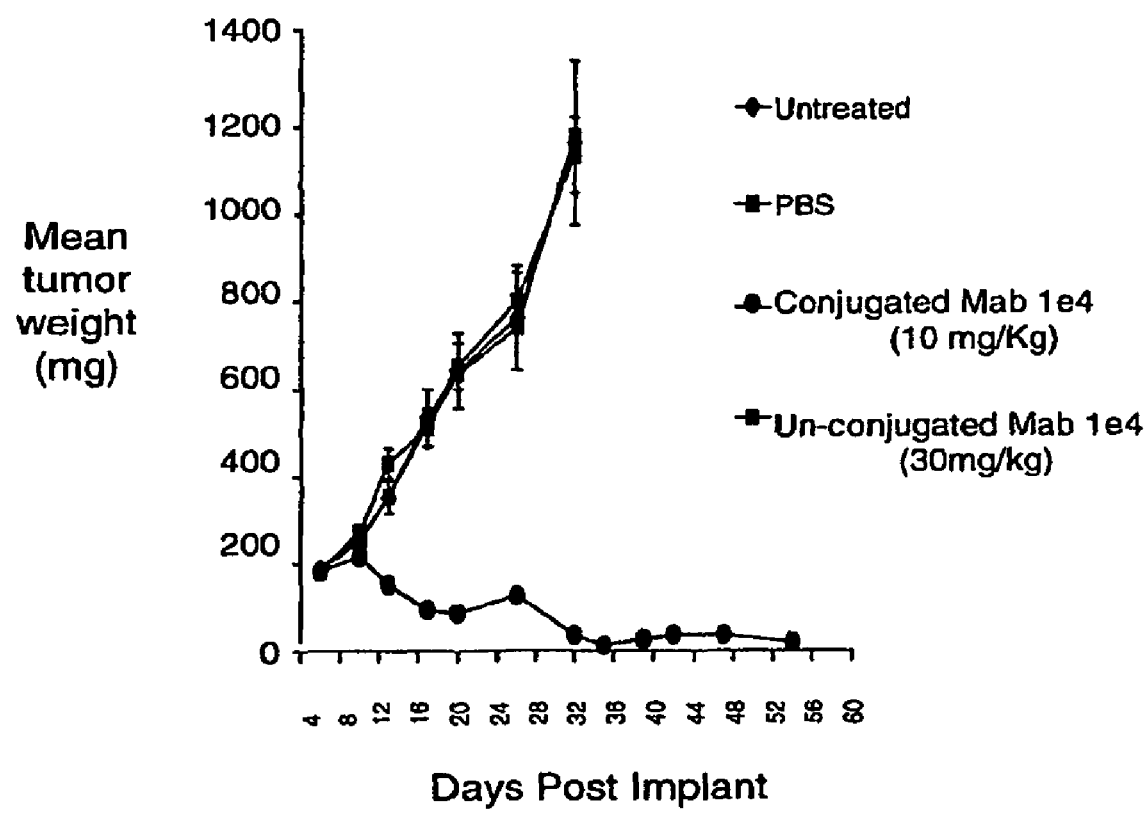
FIG. 7 depicts the in vivo anti-tumor activity in a xenograft model comprising the MaTu tumor resulting from treatment with an immunoconjugate comprising the anti-MN monoclonal antibody 1e4.

It is to be understood that present invention as described herein is not to be limited to the particular details set forth herein regarding any aspect of the present invention, including, anti-MN antibodies, immunoconjugates, methods of treatment, protocols, cell lines, animal species or genera, constructs, and reagents described and, as such, may vary. It is also to be understood that the terminology used herein is for the purpose of describing particular embodiments only, and is not intended to limit the scope of the present invention.

Definitions

Unless defined otherwise, all technical and scientific terms used herein have the meaning commonly understood by one of ordinary skill in the art to which this invention belongs. The following references, however, can provide one of skill in the art to which this invention pertains with a general definition of many of the terms used in this invention, and can be referenced and used so long as such definitions are consistent the meaning commonly understood in the art. Such references include, but are not limited to, Singleton et al., Dictionary of Microbiology and Molecular Biology (2d ed. 1994); The Cambridge Dictionary of Science and Technology (Walker ed., 1988); Hale & Marham, The Harper Collins Dictionary of Biology (1991); and Lackie et al., The Dictionary of Cell & Molecular Biology (3d ed. 1999); and Cellular and Molecular Immunology, Eds. Abbas, Lichtman and Pober, 2$^{nd}$ Edition, W.B. Saunders Company. Any additional technical resources available to the person of ordinary skill in the art providing definitions of terms used herein having the meaning commonly understood in the art can be consulted. For the purposes of the present invention, the following terms are further defined. Additional terms are defined elsewhere in the description.

As used herein and in the appended claims, the singular forms "a," "and," and "the" include plural reference unless the context clearly dictates otherwise. Thus, for example, reference to "a gene" is a reference to one or more genes and includes equivalents thereof known to those skilled in the art, and so forth.

As used herein, the term "antibody" includes immunoglobulin molecules (e.g., any type, including IgG, IgE, IgM, IgD, IgA and IgY, and/or any class, including, IgG1, IgG2, IgG3, IgG4, IgA1 and IgA2) isolated from nature or prepared by recombinant means. Antibodies also are meant to encompass antigen-binding antibody fragments, such as Fab, F(ab')$_2$, scFv (single chain Fvs), Fv, single chain antibodies, diabodies, disulfide-linked Fvs (sdFv), and fragments comprising a $V_L$ or $V_H$ domain, which are prepared from intact immunoglobulins or prepared by recombinant means.

The antibodies and/or antigen-binding antibody fragments of the present invention may be monospecific (e.g. monoclonal), bispecific, trispecific or of greater multi specificity. Multispecific antibodies may be specific for different epitopes of an antigen or may be specific for epitopes of more than one antigen. See, e.g., PCT publications WO 93/17715; WO 92/08802; WO 91/00360; WO 92/05793; Tutt, et al., 1991, J. Immunol. 147:60 69; U.S. Pat. Nos. 4,474,893; 4,714,681; 4,925,648; 5,573,920; 5,601,819; Kostelny et al., 1992, J. Immunol. 148:1547 1553, each of which are incorporated herein by reference.

Antigen-binding antibody fragments may comprise the variable region(s) alone or in combination with the entirety or a portion of the following: hinge region, CH1, CH2, CH3 and CL domains. Also included in the invention are antigen-binding antibody fragments also comprising any combination of variable region(s) with a hinge region, CH1, CH2, CH3 and CL domain.

Preferably, the antibodies or antigen-binding antibody fragments are human, humanized, murine (e.g., mouse and rat), donkey, sheep, rabbit, goat, guinea pig, camelid, horse, or chicken. As used herein, "human" antibodies include antibodies having the amino acid sequence of a human immunoglobulin and include antibodies isolated from human immunoglobulin libraries, from human B cells, or from animals transgenic for one or more human immunoglobulin, as described infra and, for example in U.S. Pat. No. 5,939,598 by Kucherlapati et al. The term antibody also extends to other protein scaffolds that are able to orient antibody CDR inserts into the same active binding conformation as that found in natural antibodies such that binding of the target antigen observed with these chimeric proteins is maintained relative to the binding activity of the natural antibody from which the CDRs were derived.

As used herein, the term "humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues (e.g. the complementarity determining regions "CDR") of the recipient are replaced by hypervariable region residues (CDRs) from a non-human species (donor antibody) such as mouse, rat, rabbit, or nonhuman primate having the desired specificity, affinity, and capacity. In some instances, framework region (FR) residues of the human immunoglobulin may be replaced by corresponding non-human residues. Furthermore, humanized antibodies may comprise residues which are not found in the recipient antibody or in the donor antibody. Such modifications are made to further refine antibody performance. In general, the humanized antibody may comprise substantially all of at least one or typically two variable domains, in which all or substantially all of the hypervariable regions correspond to those of a non-human immunoglobulin and all or substantially all of the FRs are those of a human immunoglobulin sequence. The humanized antibody optionally also may comprise at least a portion of an immunoglobulin constant region (Fc), typically that of a human immunoglobulin. For a review, see Jones, et al., (Nature 321:522-525, 1986); Reichmann, et al., (Nature 332:323-329, 1988); and Presta, (Curr. Op. Struct. Biol. 2:593-596, 1992). The preparation of humanized antibodies can be found in U.S. Pat. Nos. 7,049,135, 6,828,422, 6,753,136, 6,706,484, to 6,696,248, 6,692,935, 6,667,150, 6,653,068, 6,300,064, 6,294,353, and 5,514,548, each of which are incorporated herein in their entireties.

As used herein, the term "single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for antigen binding. For a review, see Pluckthun (*The Pharmacology of Monoclonal Antibodies*, Vol. 113, Rosenburg and Moore eds. Springer-Verlag, New York, pp. 269-315, 1994), which is incorporated herein in its entirety by reference.

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger, et al., (Proc. Natl. Acad. Sci. USA 90:6444-6448, 1993), each of which are incorporated by reference.

The expression "linear antibodies" refers to the antibodies described in the art, for example, in Zapata, et al., (Protein Eng. 8(10):1057-1062, 1995), which is incorporated by reference. Briefly, such antibodies comprise a pair of tandem Fd segments ($V_H$-$C_H$1-$V_H$-$C_H$1) which form a pair of antigen binding regions. Linear antibodies can be bispecific or monospecific.

The term "monoclonal antibody" as used herein refers to an antibody obtained from a population of substantially homogeneous antibodies, that is, individual antibodies comprising an identical population except for possible naturally occurring mutations that may be present in minor amounts. Monoclonal antibodies are highly specific, that is, directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler, et al., (Nature 256:495, 1975), or may be made by recombinant DNA methods (see, e.g., U.S. Pat. No. 4,816,567). Monoclonal antibodies may also be isolated from phage antibody libraries using the techniques described in, for example, Clackson, et al., (Nature 352:624-628, 1991) and Marks, et al., (J. Mol. Biol. 222:581-597, 1991).

The monoclonal antibodies herein also include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, ±5 so long as they exhibit the desired biological activity (see, e.g., U.S. Pat. No. 4,816,567; and Morrison, et al., Proc. Natl. Acad. Sci. USA 81:6851-6855, 1984, each of which are incorporated by reference).

As used herein, the terms "biological sample" or "patient sample" as used herein, refers to a sample obtained from an organism or from components (e.g., cells) of an organism. The sample may be of any biological tissue or fluid. The sample may be a "clinical sample" which is a sample derived from a patient. Such samples include, but are not limited to, sputum, blood, serum, plasma, blood cells (e.g., white cells), tissue samples, biopsy samples, urine, peritoneal fluid, and pleural fluid, saliva, semen, breast exudate, cerebrospinal fluid, tears, mucous, lymph, cytosols, ascites, amniotic fluid, bladder washes, and bronchioalveolar lavages or cells therefrom, among other body fluid samples. The patient samples may be fresh or frozen, and may be treated with heparin, citrate, or EDTA. Biological samples may also include sections of tissues such as frozen sections taken for histological purposes.

The term "cancer" includes, but is not limited to, solid tumors, such as cancers of the breast, respiratory tract, brain, reproductive organs, digestive tract, urinary tract, eye, liver, skin, head and neck, thyroid, parathyroid, and their distant metastases. The term also includes sarcomas, lymphomas, leukemias, and plasma cell myelomas.

Examples of breast cancer include, but are not limited to, invasive ductal carcinoma, invasive lobular carcinoma, ductal carcinoma in situ, and lobular carcinoma in situ. Examples of cancers of the respiratory tract include, but are not limited to, small-cell and non-small-cell lung carcinoma, as well as bronchial adenoma and pleuropulmonary blastoma. Examples of brain cancers include, but are not limited to, brain stem and hypophtalmic glioma, cerebellar and cerebral astrocytoma, medulloblastoma, ependymoma, as well as neuroectodermal and pineal tumor. Tumors of the male reproductive organs include, but are not limited to, prostate and testicular cancer. Tumors of the female reproductive organs include, but are not limited to, endometrial, cervical, ovarian, vaginal, and vulvar cancer, as well as sarcoma of the uterus. Tumors of the digestive tract include, but are not limited to, anal, colon, colorectal, esophageal, gallbladder, gastric, pancreatic, rectal, small-intestine, and salivary gland cancers. Tumors of the urinary tract include, but are not limited to, bladder, penile, kidney, renal pelvis, ureter, and urethral cancers. Eye cancers include, but are not limited to, intraocular melanoma and retinoblastoma. Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to, squamous cell carcinoma, Kaposi's sarcoma, malignant melanoma, Merkel cell skin cancer, and non-melanoma skin cancer. Head-and-neck cancers include, but are not limited to, laryngeal/hypopharyngeal/nasopharyngeal/oropharyngeal cancer, and lip and oral cavity cancer. Lymphomas include, but are not limited to, AIDS-related lymphoma, non-Hodgkin's lymphoma, cutaneous T-cell lymphoma, Hodgkin's disease, and lymphoma of the central nervous system. Sarcomas include, but are not limited to, sarcoma of the soft tissue, osteosarcoma, malignant fibrous histiocytoma, lymphosarcoma, and rhabdomyosarcoma. Leukemias include, but are not limited to, acute myeloid leukemia, acute lymphoblastic leukemia, chronic lymphocytic leukemia, chronic myelogenous leukemia, and hairy cell leukemia.

As used in this invention, the term "epitope" means any antigenic determinant on an antigen, e.g. MN protein, to which the antibody binds through an antigenic binding site. Determinants or antigenic determinants usually consist of chemically active surface groupings of molecules such as amino acids or sugar side chains and usually have specific three dimensional structural characteristics, as well as specific charge characteristics.

The term "specifically immunoreactive" refers to a binding reaction between an antibody and a protein, compound, or antigen, having an epitope recognized by the antigenic binding site of the antibody. This binding reaction is determinative of the presence of a protein, antigen or epitope having the recognized epitope amongst the presence of a heterogeneous population of proteins and other biologics. In the context of an immunoassay, specifically immunoreactive antibodies can bind to a protein having the recognized epitope and bind, if at all, to a detectably lesser degree to other proteins lacking the epitope which are present in the sample. In an in vivo context, "specifically immunoreactive" can refer to the conditions under which in an animal forms an immune response against a vaccine or antigen, e.g. a humoral response to the antigen (the production of antibodies, against a vaccine, protein, compound, or antigen presented thereto under immunologically reactive conditions) or a cell-mediated (also herein as "cellular immune response", i.e. a response mediated by T lymphocytes against the vaccine, protein, compound or antigen presented thereto).

As used herein, the term "immunologically reactive conditions" is used in the context of an immunoassay or an in vitro reaction wherein the physical conditions of the reaction, including, for example, the temperature, salt concentration, pH, reagents and their concentrations, and the concentrations of antigen and cognate antibody that is specifically immunoreactive to the antigen, are provided or adjusted to allow binding of the cognate antibody to the antigen. Immunologically reactive conditions are dependent upon the format of the antibody binding reaction and, typically are those utilized in immunoassay protocols. See Harlow and Lane (1988) Antibodies: A Laboratory Manual, Cold Spring Harbor Publications, New York, for a description of immunoassay formats and conditions.

The term "patient" or "subject" as used herein includes mammals (e.g., humans and animals).

Antibodies

The present invention relates to antibodies that bind to MN. These antibodies may be useful for a variety of therapeutic and diagnostic purposes.

It will be generally appreciated by those skilled in the art that the most critical determinants of antibody selectivity and binding affinity are the sequences and resulting conformations of the complementarity regions (CDRs). Most antibodies contain six CDRs, three within the heavy chain variable region (VH) and three within the light chain variable region (VL). The intervening sequences between the CDRs within VH and VL are the framework regions which orient the CDRs. The CDRs together form the antigenic binding sites within antibodies. The critical role of these CDRs in determining the functional properties of antibodies has long been exploited in the processes of antibody humanization and antibody optimization. In the former process, the CDRs from a monoclonal antibody, for example, a mouse antibody are transferred to a human antibody of similar framework design thereby resulting in an antibody with the same functional properties and reduced immunogencity in man.

The success of this process is evident from the number of humanized antibodies that have been successfully commercialized as human therapeutics and include Herceptin® (trastuzumab, Genentech, Inc., South San Francisco, Calif.), Synagis® (palivizumab, Medimmune, Inc., Gaithersburg, Md.), Campath® (alemtuzumab, Genzyme Oncology, Cambridge, Mass.), Zenapax® (daclizumab, Roche Pharmaceuticlas, Nutley, N.J.), Xolair® (omalizumab, Genentech, Inc., South San Francisco, Calif.), Raptiva® (efalizumab, Genentech, Inc., South San Francisco, Calif.), Avastin® (bevacizumab, Genentech, Inc., South San Francisco, Calif.), and Mylotarg® (gemtuzumab ozogamicin, Wyeth-Ayerst, Madison, N.J.), Other examples have been described in Singer, et al., (J. Immunol, 150:2844-2857, 1993); Luo, et al., (J. Immunol. Meth., 275:31-40, 2002); and Kostelny, et al., (Int. J. Cancer 93; 556-565, 2001).

The process of antibody optimization focuses on improvements in antibody selectivity or binding affinity through specific alteration in the sequence of the CDRs. It is well accepted within the field of antibody development that the CDRs encode binding affinity and selectivity properties required for therapeutic and diagnostic uses, and these CDR sequences may be used to confer such desirable functional properties to a wide variety of alternate antibody frameworks using standard procedures known to those skilled in the art. It is also possible to transfer antibody binding activity by grafting antibody CDRs onto other proteins that possess immunoglobulin-like folds such as other proteins within the immunoglobulin superfamily and non-immunoglobulins with similar folds to immunoglobulins (Nicaise, et al., Protein Science 13:1882-1891, 2004).

The present invention contemplates any known or suitable technology for the preparation of the antibodies and antigen binding antibody fragments of the invention.

For example, phage display technology is useful for obtaining high affinity anti-MN antibodies or antigen binding antibody fragments of the invention for the use in diagnosis and/or treatment of an MN-related disorder, such as, an MN-related cancer. The technology, referred to as affinity maturation, employs mutagenesis or CDR walking and re-selection using the MN antigen to identify antibodies that bind with higher affinity to the antigen when compared with the initial or parental antibody (see, e.g., Glaser et al., 1992, J. Immunology 149:3903). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contact with the immobilized mutants containing labeled antigen. Any screening method known in the art can be used to identify mutant antibodies with increased avidity to the antigen (e.g., ELISA) (See Wu et al., 1998, Proc Natl. Acad. Sci. USA 95:6037; Yelton et al., 1995, J. Immunology 155:1994, incorporated by reference). CDR walking may also be used to randomize the light chain (See Schier et al., 1996, J. Mol. Bio. 263:551, incorporated by reference).

In a particular example, MorphoSys AG (Germany) provides a phage-antibody technology that may be used to generate fully human antibodies. The Morphosys HuCAL GOLD library provides a number of advancements over earlier versions of the technology (Knappik, et al., J. Mol. Biol. 296: 57-86, 2000, incorporated by reference) including the HuCAL-Fab 1 library described in Rauchenberger, et al., (J. Biol. Chem. 278:38194-38205, 2003, incorporated by reference). Like earlier versions, HuCAL GOLD incorporates a human antibody design, that features human consensus framework sequences and patterns of CDR variability that mimic the natural human sequence diversity. However, diversity is extended in HuCAL GOLD to include all six antibody CDRs. Moreover, recovery of high affinity antibodies is augmented through the CysDisplay™ feature (Kretzschmar and von Ruden, Curr. Opin. Biotechnol. 13:598-602, 2002). Antibodies derived with this technology exhibit a greatly reduced probability of immunogenicity.

The phage-display technologies, such as those available from Morphosys, are known in the art and reference can further be made to Boehncke W H et al., Br J. Dermatol. (2005), November; 153(5): 1092; Simon Moroney et al., Modern Biopharmaceuticals; Edited by J. Knaeblein, Wiley-VCH Verlag (2005); Ralf Ostendorp et al., Antibodies, Volume 2: Novel technologies and therapeutic use, p. 13-52, (2004), Kluwer Academic/Plenum Publishers, New York; R. Rauchenberger et al., J Biol. Chem., (2003), October 3, 278 (40): 38194-38205; T. Kretzschmar et al., Curr Opin Biotechnol., (2002), December, 13(6):598-602; Krebs B et al, J Immunol Methods, (2001), August 1, 254(1-2); M. Marget et al., Tissue Antigens, (2000), 56: 1-9; A. Knappik et al., J. Mol. Biol., (2000), February 11, 296 (1): 57-86; and A. Plückthun et al., Immunotechnology, (1997), June; 3(2): 83-105, each of which are incorporated herein by reference in their entireties.

As an example, antibodies with MN binding and cell adhesion-neutralizing activity may be identified using the MorphoSys technology. The MN protein may be coated on microliter plate or a magnetic bead and incubated with the MorphoSys HuCAL-GOLD Fab phage library. Phage-linked Fabs that do not bind to MN may be washed from the plate, leaving only phage that bind to MN. The bound phage may be eluted by addition of a thiol reducing agent such as dithiotreitol (DTT) resulting in cleavage of the disulfide bond linking the antibody to the phage. The recovered population of phage may be enriched with phage expressing MN binding antibody fragments and may be amplified by infection of E. coli hosts. This panning process may be repeated using the enriched population of phage to further enrich for a population of phage-linked antibodies that bind to MN. The gene sequence encoding the Fabs may then be excised using standard cloning techniques and transferred to an expression vector, such as a bacterial (e.g., E. coli) expression vector, or a mammalian expression vector, which is used to transform an host cell line, such as, a CHO or E. coli expression cell line. Fabs from the enriched pool may then be expressed and purified.

Alternatively, panning may be performed using MN expressing cells as antigen. For example, cells transfected with MN antigen may be labeled with biotin. These transfected cells may then be mixed with unlabeled, non-MN transfected cells, at a labeled to unlabeled ratio of 1:10. The phage library is added to the cells, and the biotinylated, MN-bearing cells are captured with streptavidin-bound magnetic beads that are bound to a magnet. Non-specific phage are washed away, and the MN-bearing cells are specifically eluted by removing the magnetic field. These specifically bound phage may be amplified for further rounds of cell panning or may be alternated with peptide and/or protein panning.

Antibodies may be produced by a variety of other techniques as described below. For example, another approach for obtaining antibodies is to screen a DNA library from B cells as described by Dower, et al., (WO 91/17271, incorporated by reference) and McCafferty, et al., (WO 92/01047) (each of which is incorporated by reference in its entirety). In these methods, libraries of phage are produced in which members display different antibodies on their outer surfaces. Antibodies are usually displayed as Fv or Fab fragments. Phage displaying antibodies are selected by affinity enrichment for binding to a selected protein.

In a variation of the phage-display method, human antibodies having the binding specificity of a selected murine antibody may be produced (e.g., WO 92/20791, incorporated by reference). In this method, either the heavy or light chain variable region of the selected murine antibody (e.g., 5C7.29) may be used as a starting material. If, for example, a light chain variable region is selected as the starting material, a phage library may be constructed in which members displays the same light chain variable region (i.e., the murine starting material) and a different heavy chain variable region. The heavy chain variable regions may be obtained from a library of rearranged human heavy chain variable regions. A phage showing strong specific binding for a protein (e.g., at least 10 nM or at least 1 nM) is selected. The human heavy chain variable region from this phage then serves as a starting material for constructing a further phage library. In this library, each phage displays the same heavy chain variable region (i.e., the region identified from the first display library) and a different light chain variable region. The light chain variable regions may be obtained from a library of rearranged human variable light chain regions. Again, phage showing strong specific binding are selected.

As another example, antibodies may also be produced using trioma methodology. The basic approach and an exemplary cell fusion partner, SPAT-4 for use in this approach, have been described by Oestberg, et al., (Hybridoma 2:361-367, 1983; U.S. Pat. No. 4,634,664, each incorporated by reference); and Engleman, et al., (U.S. Pat. No. 4,634,666, incorporated by reference). The antibody-producing cell lines obtained by this method are called triomas, because they are descended from three cells—two human and one mouse. Initially, a mouse myeloma line is fused with a human B-lymphocyte to obtain a non-antibody-producing xenogeneic hybrid cell, such as the SPAZ-4 cell line. The xenogeneic cell is then fused with an immunized human B-lymphocyte to obtain an antibody-producing trioma cell line. Triomas have been found to produce antibodies more stably than ordinary hybridomas made from human cells.

The B-lymphocytes are obtained from the blood, spleen, lymph nodes, or bone marrow of a human donor. In vivo immunization of a living human with protein is usually undesirable because of the risk of initiating a harmful response. Thus, B-lymphocytes are usually immunized in vitro with a protein (e.g., MN) or an antigenic fragment thereof, or a cell bearing said protein (e.g., MN). Specific epitopic fragments consisting essentially of the amino acid segments that bind to one of the exemplified murine antibodies may be used for in vitro immunization. B-lymphocytes are typically exposed to antigen for a period of 7-14 days in a media such as RPMI-1640 (see, e.g., U.S. Pat. No. 4,634,666) supplemented with 10% human serum:

The immunized B-lymphocytes may be fused to a xenogeneic hybrid cell such as SPAZ-4 by methods known in the art. For example, the cells may be treated with 40-50% polyethylene glycol of MW 1,000-4,000 for about 5-10 minutes at about 37° C. Cells may be separated from the fusion mixture and propagated in media selective for the desired hybrids (e.g., HAT or AH). Clones secreting antibodies having the required binding specificity may be identified by assaying the trioma culture medium for the ability to bind to a protein (e.g., MN) using the same methods as discussed above for non-human antibodies. Triomas producing human antibodies having the desired specificity may be sub-cloned, for example, by the limiting dilution technique and grown in vitro in culture medium.

Although triomas are genetically stable, they may not produce antibodies at very high levels. Expression levels may be increased by cloning antibody genes from the trioma into one or more expression vectors, and transforming the vector into a cell line such as the cell lines for expression of recombinant or humanized immunoglobulins.

Human antibodies cross-reactive with a protein (e.g., MN) may also be produced from non-human transgenic mammals having transgenes encoding at least a segment of the human immunoglobulin locus. Usually, the endogenous immunoglobulin locus of such transgenic mammals is functionally inactivated. The segment of the human immunoglobulin locus may include unrearranged sequences of heavy and light chain components. Both inactivation of endogenous immunoglobulin genes and introduction of exogenous immunoglobulin genes may be achieved by targeted homologous recombination, or by introduction of YAC chromosomes. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail, for example, by Lonberg, et al., (WO 93/12227); and Kucherlapati, (WO 91/10741) (each of which is incorporated by reference in its entirety). Cross-reacting MN human antibodies may be obtained by immunizing a transgenic non-human mammal as described above. Monoclonal antibodies may be prepared, for example, by fusing B-cells from such mammals to suitable myeloma cell lines using conventional Kohler-Milstein technology (Kohler and Milstein, Nature 256:495-497, 1975, incorporated by reference).

Mouse or other non-human antibodies that are cross-reactive with a protein (e.g., MN) may be obtained using a variety of immunization strategies. In some strategies, non-human animals (usually non-human mammals such as mice) may be immunized with MN antigens. Immunogens may include cells stably transfected with MN and expressing MN on their cell surface, and MN protein or epitopic fragments containing the segments of these molecules that bind to the exemplified cross-reacting antibodies. Antibody-producing cells obtained from the immunized animals may be immortalized and selected for the production of an antibody which specifically binds to MN (e.g., Harlow & Lane, Antibodies, A Laboratory Manual, C.S.H.P., N.Y., 1988, incorporated by reference). Binding may be detected, for example, using an appropriate secondary antibody bearing a second label. Cross-reacting antibodies may then be further screened for their capacity to direct selective cellular cytotoxicity to cells expressing MN.

The present invention also relates to humanized antibodies having similar binding specificity and affinity to selected mouse or other non-human antibodies. Humanized antibodies may be formed by linking CDR regions (e.g., CDR1, CDR2, and CDR3) of non-human antibodies to a human framework and constant regions by recombinant DNA techniques (e.g., Queen, et al., Proc. Natl. Acad. Sci. USA 86:10029-10033, 1989; WO 90/07861; each incorporated by reference in their entirety), i.e. CDR grafting. These humanized immunoglobulins have variable region framework residues substantially from a human immunoglobulin (referred to as an acceptor immunoglobulin) and complementarity determining regions (CDRs) substantially from a mouse immunoglobulin (referred to as a donor immunoglobulin). The constant region(s), if present, may also be substantially from a human immunoglobulin.

In principal, a framework sequence from any human antibody may serve as the template for CDR grafting. However, it has been demonstrated that straight CDR replacement onto such a framework often leads to significant loss of binding affinity to the antigen (Glaser, et al., J. Immunol. 149:2606, 1992); Tempest, et al., Biotechnology 9:266, 1992; Shalaby, et al., J. Exp. Med. 17: 217, 1992). The more homologous a human antibody is to the original murine antibody, the less likely combining the murine CDRs with the human framework will be to introducing distortions into the CDRs that could reduce affinity. Therefore, homology (i.e, percent sequence identity) between the humanized antibody variable region framework and the donor antibody variable region framework of preferably at least about 65%, more preferably at least about 75%, still more preferably at least about 85%, and yet more preferably about 95% or about 99% is suggested.

The heavy and light chain variable region framework residues may be derived from the same or different human antibody sequences. However, heavy chain and light chain framework sequences chosen from the same human antibody reduce the possibility of incompatibility in assembly of the two chains. The human antibody sequences may be the sequences of naturally occurring human antibodies or may be consensus sequences of several human antibodies (e.g., WO 92/22653, incorporated by reference). Certain amino acids from the human variable region framework residues may be selected for substitution based on their possible influence on CDR conformation and/or binding to antigen. Analysis of such possible influences may be accomplished by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid may be substituted by the equivalent framework amino acid from the mouse antibody when it is reasonably expected that the amino acid:

(1) contacts antigen directly,
(2) is adjacent to a CDR region in the sequence, or
(3) otherwise interacts with a CDR region (e.g., is within about 4-6 Å of a CDR region).

Other candidates for substitution are, for example, acceptor human framework amino acids that are unusual for a human immunoglobulin at that position. These amino acids may be substituted with amino acids from the equivalent position of the donor antibody or from the equivalent positions of more typical human immunoglobulins. The variable region frameworks of humanized immunoglobulins may show, for example, at least preferably about 85% sequence identity, more preferably at least about 90% sequence identity, still more preferably at least about 95% sequence identity, and even more preferably at least about 99% sequence identity, to a human variable region framework sequence or consensus of such sequences.

The present invention also relates to bispecific or bifunctional antibodies that have one binding site that specifically binds to a protein (e.g., MN) and a second binding site that specifically binds to a second moiety. In bispecific antibodies, one-heavy and light chain pair is usually from, for example, an MN binding antibody and the other pair from an antibody raised against another epitope. This results in multi-functional valency, that is, an ability to bind at least two different epitopes simultaneously.

Binding Assays

Any useful means to describe the strength of binding (or affinity) between an antibody or antibody fragment of the invention and an antigen of the invention (MN protein) can be used. For example, the dissociation constant, $K_d$ ($K_d$=k2/k1= [antibody][antigen]/[antibody-antigen complex]) can be determined by standard kinetic analyses that are known in the art. It will be appreciated by those of ordinary skill in the art that the dissociation constant indicates the strength of binding between an antibody and an antigen in terms of how easy it is to separate the complex. If a high concentration of antibody and antigen are required to form the complex, the strength or affinity of binding is low, resulting in a higher $K_d$. It follows that the smaller the $K_d$ (as expressed in concentration units, e.g. molar or nanomolar), the stronger the binding.

Affinity can be assessed and/or measured by a variety of known techniques and immunoassays, including, for example, enzyme-linked immunospecific assay (ELISA), Bimolecular Interaction Analysis (BIA) (e.g., Sjolander and Urbaniczky, Anal. Chem. 63:2338-2345, 1991; Szabo, et al., Curr. Opin. Struct. Biol. 5:699-705, 1995, each incorporated herein by reference), and fluorescence-activated cell sorting (FACS) for quantification of antibody binding to cells that express MN. BIA is a technology for analyzing biospecific interactions in real time, without labeling any of the interactants (e.g., BIAcore™). BIAcore is based on determining changes in the optical phenomenon surface plasmon resonance (SPR) in real-time reactions between biological molecules, such as, an antibody of the invention and an MN protein antigen. References relating to BIAcore technology can be further found in U.S. Published Application Nos: 2006/0223113, 2006/0134800, 2006/0094060, 2006/0072115, 2006/0019313, 2006/0014232, and 2005/0199076, each of which are incorporated herein in their entireties by reference.

Antibodies or antigen binding antibody fragments of the invention that specifically bind to a protein (e.g., MN) provide a detection signal, for example, preferably at least about 5-fold higher, more preferably at least about 10-fold higher, and still more preferably at least about 20-fold higher than a detection signal provided for other proteins when used in an immunochemical assay. As such, these antibodies may be used to immunoprecipitate a protein (e.g., MN) from solution.

The antibodies and fragments of the invention may be assayed for immunospecific binding (or binding that is "specifically immunoreactive," which is herein defined) by any suitable method known in the art. Assays involving an antibody and an antigen are known as "immunoassays," which can be employed in the present invention to characterize both the antibodies and the antigens of the invention. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety) and can be performed without undue experimentation. Exemplary immunoassays are described briefly below (but are not intended by way of limitation).

Immunoprecipitation protocols-generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 14 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1, which is incorporated herein by reference.

Western blot analysis generally comprises preparing protein samples, electrophoresis of the protein samples in a polyacrylamide gel (e.g., 8% 20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer; blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $_{32}P$ or $_{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1, which is incorporated herein by reference.

ELISAs typically comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1, which is incorporated herein by reference.

In one aspect, the present invention embodies a number of different antibodies having MN binding characteristics identified by screening the MorphoSys HuCAL GOLD Fab library. In one aspect of the invention, the amino acid sequences of three CDRs of the VH region of a human antibody were identified (SEQ ID NOS: 57-85; FIG. 2). In another embodiment of the invention, the amino acid sequences of three CDRs of the VL region of a human MN antibody were identified (SEQ ID NOS: 86-112; FIG. 2). The present invention also relates to combinations of CDRs, frameworks, and VH/VL pairs. Examples of such combinations are shown in FIG. 3 (SEQ ID NOS: 113-132 for the encoding nucleotide sequences) and in FIG. 4) SEQ ID NOS 133-152 for the protein sequences). Antibodies that have MN binding are also shown in FIG. 4. Details of the screening process are described in the examples described herein. Other selection methods for highly active specific antibodies or antibody fragments may be envisioned by those skilled in the art and used to identify human MN antibodies.

Antibodies and/or antigen binding antibody fragments of the invention may also be purified from any cell that expresses the antibodies, including host cells that have been transfected with antibody-encoding expression constructs. The host cells may be cultured under conditions whereby the antibodies are expressed. Purified antibodies and/or antigen binding antibody fragments may be separated from other cellular components that may associate with the antibodies in the cell, such as certain proteins, carbohydrates, or lipids using methods well known in the art. Such methods include, but are not limited to, size exclusion chromatography, ammonium sulfate fractionation, ion exchange chromatography, affinity chromatography, and preparative gel electrophoresis. Purity of the preparations may be assessed by any means known in the art, such as SDS-polyacrylamide gel electrophoresis. A preparation of purified antibodies may contain more than one type of antibody (e.g., antibodies with the MN binding and neutralizing characteristics).

Alternatively, antibodies may be produced using chemical methods to synthesize its amino acid sequence or portions of the antibody sequence (e.g. CDR sequences), such as by direct peptide synthesis using solid-phase techniques (e.g., Merrifield, J. Am. Chem. Soc. 85:2149-2154, 1963; Roberge, et al., Science 269:202-204, 1995, each of which are incorporated herein by reference). Protein synthesis may be performed using manual techniques or by automation. Automated synthesis may be achieved, for example, using Applied Biosystems 431A Peptide Synthesizer (Perkin Elmer). Optionally, fragments of antibodies may be separately synthesized and combined using chemical methods to produce a full-length molecule.

Once an antibody or fragment in accordance with the invention is identified or obtained, for example, by any of the methods herein described, for example, including by traditional methods of antibody production (e.g. animal immunization methods), monoclonal production, or by recombinant DNA means, it may be preferable to carry out further steps to characterize and/or purify and/or modify the antibody. For example, it may be desirable to prepare an immunoreactive antibody fragment or to prepare a purified, high-titer composition of the identified, desirable antibody or to test the immunoreactivity of the identified antibody or fragment thereof. The present invention contemplates any known and suitable methods for characterizing, purifying, or assaying the antibodies of the present invention and it is expected the any person of ordinary skill in the art to which the invention pertains will have the requisite level of technical know-how and resources, e.g. technical manuals or treatises, to accomplish any further characterization, purification and/or assaying of the antibodies of the invention without undue experimentation.

In particular aspects, the antibodies and/or antibody fragments of the invention can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997 2001), e.g., Chapters 1, 4, 6, 8, 9, 10, each entirely incorporated herein by reference.

The term "isolating" in the context of antibodies refers to any process known in the art for purifying antibodies. Methods for purifying antibodies are well known in the art and the present invention contemplates any suitable method that would be known to the skilled person and which would not require undue experimentation. For example, chromatographic methods, such as, for example, immuno-affinity chromatography (immobilized ligand to bind and trap antibody of interest), affinity chromatography, protein precipitation, ion exchange chromatography, hydrophobic interaction chromatography, size-exclusion chromatography, as well as electrophoresis, can be found described in the technical literature, for example, in Methods in Enzymology, Volume 182, Guide to Protein Purification, Eds. J. Abelson, M. Simon, Academic Press, $1^{st}$ Edition, 1990, which is incorporated herein by reference. Thus, suitable materials for performing such purification steps, such as chromatographic steps, are known to those skilled in the art. Such methods are suitable for purification of any of the antibodies, antigens or any fragments thereof that are in accordance with the invention as described herein.

Certain embodiments may require the purification or isolation of expressed proteins or antibodies or fragments thereof from a host cell or a portion thereof. Conventional procedures for isolating recombinant proteins from transformed host cells are contemplated by the present invention. Such methods include, for example, isolation of the protein or fragments of interest by initial extraction from cell pellets or from cell culture medium, followed by salting-out, and one or more chromatography steps, including aqueous ion exchange chromatography, size exclusion chromatography steps, high performance liquid chromatography (HPLC), and affinity chromatography may be used to isolate the recombinant protein or fragment. Guidance in the procedures for protein purification can be found in the technical literature, including, for example, Methods in Enzymology, Volume 182, Guide to Protein Purification, Eds. J. Abelson, M. Simon, Academic Press, $1^{st}$ Edition, 1990, which is already incorporated by reference.

Chemically-synthesized molecules may be substantially purified by preparative high performance liquid chromatography (see, e.g., Creighton, *Proteins: Structures and Molecular Principles*, WH Freeman and Co., New York, N.Y., 1983, incorporated herein by reference). The composition of a synthetic polypeptide may be confirmed by amino acid analysis or sequencing (e.g., using Edman degradation).

Polynucleotides

In another aspect, the present invention relates to polynucleotides encoding the antibodies (e.g., antibodies against MN) or the antigen binding antibody fragments of the invention. These polynucleotides may be used, for example, to produce quantities of the antibodies for therapeutic or diagnostic use or the produce samples of antibodies or fragments for use in immunoassays of the invention.

Polynucleotides that may be used to encode, for example, each of three CDRs within antibody VH regions are described by SEQ ID NOS: 1-29. Polynucleotides that may be used to encode, for example, each of three CDRs within antibody VL regions are described by SEQ ID NOS: 30-56. Polynucleotides that encode, for example, complete heavy chain and light chain variable regions of antibodies are described by SEQ ID NOS: 113-132 (FIG. 3).

Polynucleotides of the present invention may also be isolated from host cells, free of other cellular components such as membrane components, proteins, and lipids according to any known or suitable method in the art. Polynucleotides may be isolated using standard nucleic acid purification techniques, or synthesized using an amplification technique such as the polymerase chain reaction (PCR), or by using an automatic to synthesizer. Methods for isolating polynucleotides are routine and are known in the art. Any such technique for obtaining a polynucleotide may be used to obtain isolated polynucleotides encoding antibodies of the invention. For example, restriction enzymes and probes may be used to isolate polynucleotides which encode antibodies.

Antibody-encoding cDNA molecules may be made with standard molecular biology techniques, using mRNA as a template. Thereafter, cDNA molecules may be replicated using molecular biology techniques known in the art and disclosed in manuals such as Sambrook, et al., (*Molecular Cloning: A Laboratory Manual*, (Second Edition, Cold Spring Harbor Laboratory Press; Cold Spring Harbor, N.Y.; 1989, Vol. 1-3, incorporated herein by reference). An amplification technique, such as PCR, may be used to obtain additional copies of the polynucleotides.

Alternatively, synthetic chemistry techniques may be used to synthesize polynucleotides encoding antibodies of the invention. The degeneracy of the genetic code allows alternate nucleotide sequences to be synthesized that will encode an antibody having, for example, one of the VH-CDR1, VH-CDR2, VH-CDR3, VL-CDR1, VL-CDR2, VL-CDR3, complete VH or complete VL amino acid sequences (e.g., SEQ ID NOS: 57-112 and 133-152).

To express a polynucleotide encoding an antibody, the polynucleotide may be inserted into an expression vector that contains the necessary elements for the transcription and translation of the inserted coding sequence. Methods that well known to those skilled in the art may be used to construct expression vectors containing sequences encoding antibodies and appropriate transcriptional and translational control elements. These methods include in vitro recombinant DNA techniques, synthetic techniques, and in vivo genetic recombination. Such techniques are described, for example, in Sambrook, et al. (1989) and in Ausubel, et al., (*Current Protocols in Molecular Biology*, John Wiley & Sons, New York, N.Y., 1995, incorporated herein by reference).

A variety of expression vector/host systems may be utilized to contain and express sequences encoding antibodies. These include, but are not limited to, microorganisms, such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV); or bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements may vary in strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.), pSPORT1 plasmid (Life Technologies), or the like can be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses may be used, e.g. a CMV promoter. If it is necessary to generate a cell line that contains multiple copies of a nucleotide sequence encoding an antibody, vectors based on SV40 or EBV may be used with an appropriate selectable marker.

Accordingly, the present invention also relates to recombinant vectors that include isolated nucleic acid molecules of the present invention (e.g. the heavy and light chain variable regions of SEQ ID NOS: 113-132), host cells that are genetically engineered with the recombinant vectors, and the production and/or expression of the recombinant antibodies or fragments thereof of the invention.

The expression constructs can further contain sites for transcription initiation, termination and, in the transcribed region, a ribosome binding site for translation. The coding portion of the mature transcripts expressed by the constructs can further include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors can also include at least one selectable marker. Such markers include, but are not limited to, mammalian cell markers, such as, methotrexate (MTX), dihydrofolate reductase (DHFR) (see e.g., U.S. Pat. Nos. 4,399,216; 4,634,665; 4,656,134; 4,956,288; 5,149,636; and 5,179,017, each of which are incorporated by reference), ampicillin, neomycin (G418), mycophenolic acid, or glutamine synthetase (GS) (see e.g., U.S. Pat. Nos. 5,122,464; 5,770,359; 5,827,739, each of which are incorporated by reference), and bacterial cell markers, such as, tetracycline or ampicillin resistance genes. Appropriate culture mediums and conditions for the above-described host cells are known in the art. Suitable vectors will be readily apparent to the skilled artisan.

Any suitable known method for introducing a DNA of the invention, e.g. a DNA expression vector containing one or more antibody-encoding sequences of SEQ ID NOS: 113-132, into a host cell can be utilized. Some known methods include calcium phosphate transfection, DEAE-dextran mediated transfection, cationic lipid-mediated transfection, electroporation, transduction, infection or other known methods. Such methods are described in the art, such as in Sambrook, et al., (*Molecular Cloning: A Laboratory Manual*, (Second Edition, Cold Spring Harbor Laboratory Press; Cold Spring Harbor, N.Y.; 1989) Vol. 1-3, Chapters 14, 16 and 18).

Those of ordinary skill in the art are knowledgeable in the numerous expression systems available for expression of a nucleic acid encoding the antibodies or portions thereof of the present invention.

Illustrative of cell cultures useful for the production of the antibodies or antibody fragments of the invention are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the CHO, CHO-S, COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection.

Expression vectors for these cells can include one or more of the following expression control sequences, such as, but not limited to an origin of replication; a promoter (e.g., late or early SV40 promoters, the CMV promoter (e.g., U.S. Pat. Nos. 5,168,062; 5,385,839), an HSV tk promoter, a pgk (phosphoglycerate kinase) promoter, an EF-1 alpha promoter (U.S. Pat. No. 5,266,491), an immunoglobulin promoter; an enhancer, and/or processing information sites, such as ribosome binding sites, RNA splice sites, polyadenylation sites (e.g., an SV40 large T Ag poly A addition site), and transcriptional terminator sequences. Other cells useful for production of nucleic acids or proteins of the present invention are known and/or available, for instance, from the ID American Type Culture Collection Catalogue of Cell Lines and Hybridomas or other known or commercial sources.

When eukaryotic host cells are employed, polyadenlyation or transcription terminator sequences can be incorporated into the vector. An example of a terminator sequence is the polyadenlyation sequence from the bovine growth hormone gene. Sequences for accurate splicing of transcripts can also be included. An example of a splicing sequence is the VP1 intron from SV40 (Sprague, et al., J. Virol. 45:773 781 (1983)). Additionally, gene sequences to control replication in the host cell can be incorporated into the vector, as known in the art.

General texts describing additional molecular biological techniques useful herein, including the preparation of antibodies include Berger and Kimmel (*Guide to Molecular Cloning Techniques. Methods in Enzymology*, Vol. 152, Academic Press, Inc.); Sambrook, et al., (*Molecular Cloning: A Laboratory Manual*, (Second Edition, Cold Spring Harbor Laboratory Press; Cold Spring Harbor, N.Y.; 1989) Vol. 1-3); *Current Protocols in Molecular Biology*, (F. M. Ausabel et al. [Eds.], Current Protocols, a joint venture between Green Publishing Associates, Inc. and John Wiley & Sons, Inc. (supplemented through 2000)); Harlow et al., (*Monoclonal Antibodies: A Laboratory Manual*, Cold Spring Harbor Laboratory Press (1988), Paul [Ed.]); *Fundamental Immunology*, (Lippincott Williams & Wilkins (1998)); and Harlow, et al., (*Using Antibodies: A Laboratory Manual*, Cold Spring Harbor Laboratory Press (1998)), all of which are incorporated herein by reference.

In another embodiment, the present invention also relates to the use of quantitative immunoassays to measure levels of MN protein in patient samples. Many formats may be adapted for use with the methods of the present invention. For example, the detection and quantitation of MN protein in patient samples may be performed, by enzyme-linked immunosorbent assays, radioimmunoassays, dual antibody sandwich assays, agglutination assays, fluorescent immunoassays, immunoelectron and scanning microscopy, among other assays commonly known in the art. The quantitation of MN protein in such assays may be adapted by conventional methods known in the art. In one embodiment, serial changes in circulating MN protein levels may be detected and quantified by a sandwich assay in which the capture antibody has been immobilized using conventional techniques on the surface of the support.

Suitable supports include, for example, synthetic polymer supports, such as polypropylene, polystyrene, substituted polystyrene, polyacrylamides (such as polyamides and polyvinylchloride), glass beads, agarose, and nitrocellulose.

An example of an ELISA sandwich immunoassay that may be used in the methods of the present invention, uses mouse anti-human MNN monoclonal antibody as the capture antibody and biotinylated goat anti-human MN polyclonal antibody as the detector antibody. The capture monoclonal antibody is immobilized on microtiter plate wells. Diluted human serum/plasma samples or MN standards (recombinant wild-type MN protein) are incubated in the wells to allow binding of MN antigen by the capture monoclonal antibody. After washing of wells, the immobilized MN antigen is exposed to a biotinylated detector antibody after which the wells are again washed. A streptavidin-horseradish peroxidase conjugate is then added. After a final wash, TMB Blue Substrate is added to the wells to detect bound peroxidase activity. The reaction is stopped by the addition of 2.5 N sulfuric acid, and the absorbance is measured at 450 nm. Correlating the absorbance values of samples with the MN standards allows the determination of a quantitative value of MN in pg/ml of serum or plasma.

The antibodies useful to identify MN proteins may be labeled in any conventional manner. An example of a label is horseradish peroxidase, and an example of a method of labeling antibodies is by using biotin-strepavidin complexes.

As appropriate, antibodies used in the immunoassays of this invention that are used as tracers may be labeled in any manner, directly or indirectly, that results in a signal that is visible or can be rendered visible. Detectable marker substances include radionuclides, such as $^3$H, $^{125}$I, and $^{131}$I; fluorescers, such as, fluorescein isothiocyanate and other fluorochromes, phycobiliproteins, phycoerythin, rare earth chelates, Texas red, dansyl and rhodamine; colorimetric reagents (chromogens); electron-opaque materials, such as colloidal gold; bioluminescers; chemiluminescers; dyes; enzymes, such as, horseradish peroxidase, alkaline phosphatases, glucose oxidase, glucose-6-phosphate dehydrogenase, acetylcholinesterase, alpha-, beta-galactosidase, among others; coenzymes; enzyme substrates; enzyme cofactors; enzyme inhibitors; enzyme subunits; metal ions; free radicals; or any other immunologically active or inert substance which provides a means of detecting or measuring the presence or amount of immunocomplex formed. Exemplary of enzyme substrate combinations are horseradish peroxidase and tetramethyl benzidine (TMB), and alkaline phosphatases and paranitrophenyl phosphate (pNPP).

Another detection and quantitation systems according to this invention produce luminescent signals, bioluminescent (BL) or chemiluminescent (CL). In chemiluminescent (CL)

or bioluminescent (BL) assays, the intensity or the total light emission is measured and related to the concentration of the unknown analyte. Light can be measured quantitatively using a luminometer (photomultiplier tube as the detector) or charge-coupled device, or qualitatively by means of photographic or X-ray film. The main advantages of using such assays is their simplicity and analytical sensitivity, enabling the detection and/or quantitation of very small amounts of analyte.

Exemplary luminescent labels are acridinium esters, acridinium sulfonyl carboxamides, luminol, umbelliferone, isoluminol derivatives, photoproteins, such as aequorin, and luciferases from fireflies, marine bacteria, *Vargulla* and *Renilla*. Luminol can be used optionally with an enhancer molecule such as 4-iodophenol or 4-hydroxy-cinnamic acid. Typically, a CL signal is generated by treatment with an oxidant under basic conditions.

Additional luminescent detection systems are those wherein the signal (detectable marker) is produced by an enzymatic reaction upon a substrate. CL and BL detection schemes have been developed for assaying alkaline phosphatases (AP), glucose oxidase, glucose 6-phosphate dehydrogenase, horseradish peroxidase (HRP), and xanthine-oxidase labels, among others. AP and HRP are two enzyme labels which can be quantitated by a range of CL and BL reactions. For example, AP can be used with a substrate, such as an adamantyl 1,2-dioxetane aryl phosphate substrate (e.g. AMPPD or CSPD; Kricka, L. J., "Chemiluminescence and Bioluminescence, Analysis by," *Molecular Biology and Biotechnology: A Comprehensive Desk Reference* (ed. R. A. Meyers) (VCH Publishers; N.Y., N.Y.; 1995)); for example, a disodium salt of 4-methoxy-4-(3-phosphatephenyl) spiro [1,2-dioxetane-3,2'-adamantane], with or without an enhancer molecule such as 1-(trioctylphosphonium methyl)-4-(tributylphosphonium methyl) benzene diochloride. HRP is may be used with substrates, such as, 2',3',6'-trifluorophenyl-methoxy-10-methylacridan-9-carboxylate.

CL and BL reactions may be adapted for analysis not only of enzymes, but also of other substrates, cofactors, inhibitors, metal ions, and the like. For example, luminol, firefly luciferase, and marine bacterial luciferase reactions are indicator reactions for the production or consumption of peroxide, ATP, and NADPH, respectively. They may be coupled to other reactions involving oxidases, kinases, and dehydrogenases, and may be used to measure any component of the coupled reaction (enzyme, substrate, cofactor).

The detectable marker may be directly or indirectly linked to an antibody used in an assay of this invention. Exemplary of an indirect linkage of the detectable label is the use of a binding pair between an antibody and a marker or the use of a signal amplification system.

Examples of binding pairs that may be used to link antibodies to detectable markers are biotin/avidin, streptavidin, or anti-biotin; avidin/anti-avidin; thyroxine/thyroxine-binding globulin; antigen/antibody; antibody/anti-antibody; carbohydrate/lectins; hapten/anti-hapten antibody; dyes and hydrophobic molecules/hydrophobic protein binding sites; enzyme inhibitor, coenzyme or cofactor/enzyme; polynucleic acid/homologous polynucleic acid sequence; fluorescein/anti-fluorescein; dinitrophenol/anti-dinitrophenol; vitamin B12/intrinsic factor; cortisone, cortisol/cortisol binding protein; and ligands for specific receptor protein/membrane associated specific receptor proteins.

Various means for linking labels directly or indirectly to antibodies are known in the art. For example, labels may be bound either covalently or non-covalently. Exemplary antibody conjugation methods are described in Avarmeas, et al., Scan. J. Immunol. 8(Suppl. 7): 7, 1978); Bayer, et al., Meth. Enzymol. 62:308, 1979; Chandler, et al., J. Immunol. Meth. 53:187, 1982; Ekeke and Abuknesha, J. Steroid Biochem. 11:1579, 1979; Engvall and Perlmann, J. Immunol. 109:129, 1972; Geoghegan, et al., Immunol. Comm. 7:1, 1978; and Wilson and Nakane, *Immunofluorescence and Related Techniques*, Elsevier/North Holland Biomedical Press; Amsterdam (1978), each of which are incorporate herein by reference.

Depending upon the nature of the label, various techniques may be employed for detecting and quantitating the label. For fluorescers, a large number of fluorometers are available. For chemiluminescers, luminometers or films are available. With enzymes, a fluorescent, chemiluminescent, or colored product may be determined or measured fluorometrically, luminometrically, spectrophotometrically, or visually.

Various types of chemiluminescent compounds having an acridinium, benzacridinium, or acridan type of heterocyclic ring systems are other examples of labels. Examples of acridinium esters include those compounds having heterocyclic rings or ring systems that contain the heteroatom in a positive oxidation state including such ring systems as acridinium, benz[b]acridinium, benz[b]acridinium, benz[c]acridinium, a benzimidazole cation, quinolinium, isoquinolinium, quinolizinium, a cyclic substituted quinolinium, phenanthridinium, and quinoxalinium.

The tracer may be prepared by attaching to the selected antibody either directly or indirectly a reactive functional group present on the acridinium or benzacridinium ester, as is well known to those skilled in the art (see, e.g., Weeks, et al., Clin. Chem. 29(8):1474-1479, 1983). Examples of compounds are acridinium and benzacridinium esters with an aryl ring leaving group and the reactive functional group present in either the para or the meta position of the aryl ring. (e.g., U.S. Pat. No. 4,745,181 and WO 94/21823, incorporated herein by reference).

Methods of Use

The term "treatment" includes any process, action, application, therapy, or the like, wherein a subject (or patient), including a human being, is provided medical aid with the object of improving the subject's condition, directly or indirectly, or slowing the progression of a-condition or disorder in the subject, or ameliorating at least one symptom of the disease or disorder under treatment.

The term "combination therapy" or "co-therapy" means the administration of two or more therapeutic agents to treat a disease, condition, and/or disorder. Such administration encompasses co-administration of two or more therapeutic agents in a substantially simultaneous manner, such as in a single capsule having a fixed ratio of active ingredients or in multiple, separate capsules for each inhibitor agent. In addition, such administration encompasses use of each type of therapeutic agent in a sequential manner. The order of administration of two or more sequentially co-administered therapeutic agents is not limited.

The phrase "therapeutically effective amount" means the amount of each agent administered that will achieve the goal of improvement in a disease, condition, and/or disorder severity, and/or symptom thereof, while avoiding or minimizing adverse side effects associated with the given therapeutic treatment.

The term "pharmaceutically acceptable" means that the subject item is appropriate for use in a pharmaceutical product.

The antibodies of this invention are expected to be valuable as therapeutic agents. Accordingly, an embodiment of this invention includes a method of treating the various conditions in a patient (including mammals) which comprises administering to said patient a composition containing an amount of an antibody of the invention that is effective in treating the target condition.

The antibodies of the present invention may be used in the treatment or prevention of diseases and/or behaviors that are associated with the MN protein. These diseases and/or behaviors include, for example, cancer, such as, carcinomas of the kidney, esophagus, breast, cervix, colon, and lung. The present invention also relates to methods of ameliorating symptoms of a disorder in which MN is elevated or otherwise abnormally expressed. These disorders include, without limitation, carcinomas of the kidney, esophagus, breast, cervix, colon, and lung (see, e.g., (Liao, Cancer Res. 57:2827-2831, 1997; Turner, Hum. Pathol. 28:740-744, 1997; Liao, et al., Am. J. Pathol. 145:598-609, 1994; Saarnio, et al., Am. J. Pathol. 153:279-285, 1998; Vermylen, et al., Eur. Respir. J. 14:806-811, 1999). In one embodiment of the invention, a therapeutically effective dose of an antibody of the invention is administered to a patient having a disorder in which MN is elevated.

Antibodies of the present invention may be administered alone or in combination with one or more additional therapeutic agents. Combination therapy includes administration of a single pharmaceutical dosage formulation which contains an antibody of the present invention and one or more additional therapeutic agents, as well as administration of the antibody of the present invention and each additional therapeutic agents in its own separate pharmaceutical dosage formulation. For example, an antibody of the present invention and a therapeutic agent may be administered to the patient together in a single oral dosage composition or each agent may be administered in separate oral dosage formulations.

Where separate dosage formulations are used, the antibody of the present invention and one or more additional therapeutic agents may be administered at essentially the same time (e.g., concurrently) or at separately staggered times (e.g., sequentially). The order of administration of the agents is not limited.

For example, in one aspect, co-administration of an anti-MN antibody or antibody fragment of the invention together with one or more anti-cancer agents to potentiate the effect of either the antibody/fragment or the anti-cancer agent(s) or both is contemplated for use in treating MN-related disorders, such as, cancer.

Such combination-therapies may also be used to prevent cancer, prevent the recurrence of cancer, prevent the spread or metastasis of a cancer, or reduce or ameliorate the symptoms associated with cancer.

The one or more anti-cancer agents can include any known and suitable compound in the art, such as, for example, chemoagents, other immunotherapeutics, cancer vaccines, anti-angiogenic agents, cytokines, hormone therapies, gene therapies, and radiotherapies. A chemoagent (or "anti-cancer agent" or "anti-tumor agent" or "cancer therapeutic") refers to any molecule or compound that assists in the treatment of a cancer. Examples of chemoagents contemplated by the present invention include, but are not limited to, cytosine arabinoside, taxoids (e.g., paclitaxel, docetaxel), anti-tubulin agents (e.g., paclitaxel, docetaxel, epothilone B, or its analogues), macrolides (e.g., rhizoxin) cisplatin, carboplatin, adriamycin, tenoposide, mitozantron, discodermolide, eleutherobine, 2-chlorodeoxyadenosine, alkylating agents (e.g., cyclophosphamide, mechlorethamine, thioepa, chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP) cisplatin, thio-tepa), antibiotics (e.g., dactinomycin (formerly actinomycin), bleomycin, mithramycin, anthramycin), antimetabolites (e.g., methotrexate, 6-mercaptopurine, 6-thioguanine, cytarabine, flavopiridol, 5-fluorouracil, fludarabine, gemcitabine, dacarbazine, temozolamide), asparaginase, *Bacillus* Calmette and Guerin, diphtheria toxin, hexamethylmelamine, hydroxyurea, LYSODREN®, nucleoside analogues, plant alkaloids (e.g., Taxol, paclitaxel, camptothecin, topotecan, irinotecan (CAMPTOSAR, CPT-11), vincristine, vinca alkyloids such as vinblastine), podophyllotoxin (including derivatives such as epipodophyllotoxin, VP-16 (etoposide), VM-26 (teniposide)), cytochalasin B, colchine, gramicidin D, ethidium bromide, emetine, mitomycin, procarbazine, mechlorethamine, anthracyclines (e.g., daunorubicin (formerly daunomycin), doxorubicin, doxorubicin liposomal), dihydroxyanthracindione, mitoxantrone, mithramycin, actinomycin D, procaine, tetracaine, lidocaine, propranolol, puromycin, anti-mitotic agents, abrin, ricin A, pseudomonas exotoxin, nerve growth factor, platelet derived growth factor, tissue plasminogen activator, aldesleukin, allutamine, anastrozole, bicalutamide, biaomycin, busulfan, capecitabine, carboplain, chlorabusil, cladribine, cylarabine, daclinomycin, estramusine, floxuridhe, gamcitabine, gosereine, idarubicin, itosfamide, lauprolide acetate, levamisole, lomusline, mechlorethamine, magestrol, acetate, mercaptopurino, mesna, mitolanc, pegaspergase, pentoslatin, picamycin, riuxlmab, campath-1, straplozocin, thioguanine, tretinoin, vinorelbine, or any fragments, family members, or derivatives thereof, including pharmaceutically acceptable salts thereof. Compositions comprising one or more chemoagents (e.g., FLAG, CHOP) are also contemplated by the present invention. FLAG comprises fludarabine, cytosine arabinoside (Ara-C) and G-CSF. CHOP comprises cyclophosphamide, vincristine, doxorubicin, and prednisone.

The chemoagent can be an anti-angiogenic agent, such as, for example, angiostatin, bevacizumab (Avastin®), sorafenib (Nexavar®), baculostatin, canstatin, maspin, anti-VEGF antibodies or peptides, anti-placental growth factor antibodies or peptides, anti-Flk-1 antibodies, anti-Flt-1 antibodies or peptides, laminin peptides, fibronectin peptides, plasminogen activator inhibitors, tissue metalloproteinase inhibitors, interferons, interleukin 12, IP-10, Gro-β, thrombospondin, 2-methoxyoestradiol, proliferin-related protein, carboxiamidotriazole, CM101, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, accutin, cidofovir, vincristine, bleomycin, AGM-1470, platelet factor 4 or minocycline. Without being bound by theory, the coadministration of an anti-angiogenic agent advantageously may lead to the increase in MN expression in a tumor, thereby making the tumor more susceptible to the antibodies and antibody conjugates of the invention.

In one aspect, said chemoagent is gemcitabine at a dose ranging from 100 to 1000 mg/m$^2$/cycle. In one embodiment, said chemoagent is dacarbazine at a dose ranging from 200 to 4000 mg/m$^2$ cycle. In another aspect, said dose ranges from 700 to 1000 mg/m$^2$/cycle. In yet another aspect, said chemoagent is fludarabine at a dose ranging from 25 to 50 mg/m$^2$/cycle. In another aspect, said chemoagent is cytosine arabinoside (Ara-C) at a dose ranging from 200 to 2000 mg/m$^2$/cycle. In still another aspect, said chemoagent is docetaxel at a dose ranging from 1.5 to 7.5 mg/kg/cycle. In yet another aspect, said chemoagent is paclitaxel at a dose ranging from 5 to 15 mg/kg/cycle. In a further aspect, said chemoagent is cisplatin at a dose ranging from 5 to 20 mg/kg/cycle. In a still further aspect, said chemoagent is 5-fluorouracil at a dose ranging from 5 to 20 mg/kg/cycle. In another aspect, said chemoagent is doxorubicin at a dose ranging from 2 to 8 mg/kg/cycle. In yet a further aspect, said chemoagent is epipodophyllotoxin at a dose ranging from 40 to 160 mg/kg/cycle. In yet another aspect, said chemoagent is cyclophosphamide at a dose ranging from 50 to 200 mg/kg/cycle. In a further aspect, said chemoagent is irinotecan at a dose ranging from 50 to 150 mg/m$^2$/cycle. In a still further aspect, said chemoagent is vinblastine at a dose ranging from 3.7 to 18.5 mg/m$^2$/cycle. In another aspect, said chemoagent is vincristine at a dose ranging from 0.7 to 2 mg/m$^2$/cycle. In one aspect, said chemoagent is methotrexate at a dose ranging from 3.3 to 1000 mg/m$^2$/cycle.

In another aspect, the anti-MN antibodies and/or antibody fragments of the present invention are administered in combination with one or more immunotherapeutic agents, such as antibodies or immunomodulators, which include, but are not limited to, Herceptin®, Retuxan®., OvaRex, Panorex, BEC2, IMC-C225, Vitaxin, Campath I/H, Smart MI95, LymphoCide, Smart ID10, and Oncolym, rituxan, rituximab, gemtuzumab, or trastuzumab.

The invention also contemplates administering the anti-MN antibodies and/or antibody fragments of the present invention with one or more anti-angiogenic agents, which includes, but is not limited to, angiostatin, thalidomide, kringle 5, endostatin, Serpin (Serine Protease Inhibitor) antithrombin, 29 kDa N-terminal and a 40 kDa C-terminal proteolytic fragments of fibronectin, 16 kDa proteolytic fragment of prolactin, 7.8 kDa proteolytic fragment of platelet factor-4, a β-amino acid peptide corresponding to a fragment of platelet factor-4 (Maione et al., 1990, Cancer Res. 51:2077), a 14-amino acid peptide corresponding to a fragment of collagen I (Tolma et al., 1993, J. Cell Biol. 122:497), a 19 amino acid peptide corresponding to a fragment of Thrombospondin I (Tolsma et al., 1993, J. Cell Biol. 122: 497), a 20-amino acid peptide corresponding to a fragment of SPARC (Sage et al., 1995, J. Cell. Biochem. 57:1329-), or any fragments, family members, or derivatives thereof, including pharmaceutically acceptable salts thereof.

Other peptides that inhibit angiogenesis and correspond to fragments of laminin, fibronectin, procollagen, and EGF have also been described (See the review by Cao, 1998, Prog. Mol. Subcell. Biol. 20:161). Monoclonal antibodies and cyclic pentapeptides, which block certain integrins that bind RGD proteins (i.e., possess the peptide motif Arg-Gly-Asp), have been demonstrated to have anti-vascularization activities (Brooks et al., 1994, Science 264:569; Hanunes et al., 1996, Nature Medicine 2:529). Moreover, inhibition of the urokinase plasminogen activator receptor by antagonists inhibits angiogenesis, tumor growth and metastasis (Min et al., 1996, Cancer Res. 56:2428-33; Crowley et al., 1993, Proc Natl Acad. Sci. USA 90:5021). Use of such anti-angiogenic agents is also contemplated by the present invention.

In another-aspect, the anti-MN antibodies and/or antibody fragments of the present invention are administered in combination with a regimen of radiation.

The anti-MN antibodies and/or antibody fragments of the present invention can also be administered in combination with one or more cytokines, which includes, but is not limited to, lymphokines, tumor necrosis factors, tumor necrosis factor-like cytokines, lymphotoxin-α, lymphotoxin-β, interferon-β, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD137 ligands, Fas-Pas ligand, 4-1BBL, endothelial monocyte activating protein or any fragments, family members, or derivatives thereof, including pharmaceutically acceptable salts thereof.

The anti-MN antibodies and/or antibody fragments of the present invention can also be administered in combination with a cancer vaccine, examples of which include, but are not limited to, autologous cells or tissues, non-autologous cells or tissues, carcinoembryonic antigen, alpha-fetoprotein, human chorionic gonadotropin, BCG live vaccine, melanocyte lineage proteins (e.g., gp100, MART-1/MelanA, TRP-1 (gp75), tyrosinase, widely shared tumor-associated, including tumor-specific, antigens (e.g., BAGE, GAGE-1, GAGE-2, MAGE-1, MAGE-3, N-acetylglucosaminyltransferase-V, p15), mutated antigens that are tumor-associated (β-catenin, MUM-1, CDK4), nonmelanoma antigens (e.g., HER-2/neu (breast and ovarian carcinoma), human papillomavirus-E6, E7 (cervical carcinoma), MUC-1 (breast, ovarian and pancreatic carcinoma). For human tumor antigens recognized by T-cells, see generally Robbins and Kawakami, 1996, Curr. Opin. Immunol. 8:628. Cancer vaccines may or may not be purified preparations.

In yet another embodiment, the anti-MN antibodies and/or antibody fragments of the present invention are used in association with a hormonal treatment. Hormonal therapeutic treatments comprise hormonal agonists, hormonal antagonists (e.g., flutamide, tamoxifen, leuprolide acetate (LUPRON), LH-RH antagonists), inhibitors of hormone biosynthesis and processing, and steroids (e.g., dexamethasone, retinoids, betamethasone, cortisol, cortisone, prednisone, dehydrotestosterone, glucocorticoids, mineralocorticoids, estrogen, testosterone, progestins), antigestagens (e.g., mifepristone, onapristone), and antiandrogens (e.g., cyproterone acetate).

The anti-MN antibodies and/or fragments of the invention can be used in combination with, e.g. co-administered with, an anti-MDR (multidrug resistance) phenotype agent.

Many human cancers intrinsically express or spontaneously develop resistance to several classes of anticancer drugs at the same time, notwithstanding that each of the drug classes have different structures and mechanisms of action. This phenomenon, which can be mimicked in cultured mammalian cells, is generally referred to as multidrug resistance ("MDR") or the multidrug resistance phenotype. The MDR phenotype presents significant obstacles to the successful chemotherapeutic treatments for cancers in human patients. Resistance of malignant tumors to multiple chemotherapeutic agents is a major cause of treatment failure (Wines et al., Cancer Treat. Rep. 70:105 (1986); Bradley, G. et al., Biochim. Biophys. Acta 948:87 (1988); Griswald, D. P. et al., Cancer Treat. Rep. 65(S2):51 (1981); Osteen, R. T. (ed.), Cancer Manual, (1990)). Tumors initially sensitive to cytotoxic agents often recur or become refractory to multiple chemotherapeutic drugs (Riordan et al., Pharmacol. Ther. 28:51 (1985); Gottesman et al., Trends Pharmacol. Sci. 9:54 (1988); Moscow et al., J. Natl. Cancer Inst. 80:14 (1988); Croop, J. M. et al., J. Clin. Invest. 81:1303 (1988)). Cells or tissues obtained from tumors and grown in the presence of a selecting cytotoxic drug can result in cross-resistance to other drugs in that class as well as other classes of drugs including, but not limited to, anthracyclines, Vinca alkaloids, and epipodophyllotoxins (Riordan et al., Pharmacol. Ther. 28:51 (1985); Gottesman et al., J. Biol. Chem. 263:12163 (1988)). Thus, acquired resistance to a single drug results in simultaneous resistance to a diverse group of drugs that are structurally and functionally unrelated. Such resistance can be a problem for both solid-form and liquid-form tumors (e.g. blood or lymph-based cancers).

One major mechanism of multidrug resistance in mammalian cells involves the increased expression of the 170 kDa plasma membrane glycoprotein pump system (Juranka et al., FASEB J 3:2583 (1989); Bradley, G. et al., Biochem. Biophys. Acta 948:87 (1988)). The gene encoding this pump system, sometimes referred to as a multidrug transporter, has been cloned from cultured human cells and is generally referred to as mdr1. This gene is expressed in several classes of normal tissues, but physiological substrates transported for the mdr1 gene product in these tissues have not been identified. The MDR1 product is a member of the ABC Transporter Protein superfamily, a group of proteins having energy-dependent export function.

The protein product of the mdr1 gene, generally known as P-glycoprotein ("P-170", "P-gp"), is a 170 kDa trans-plasma membrane protein that constitutes the aforementioned energy-dependent efflux pump. Expression of P-gp on the cell surface is sufficient to render cells resistant to multiple cytotoxic drugs, including many anti-cancer agents. P-gp-mediated MDR appears to be an important clinical component of tumor resistance in tumors of different types, and mdr1 gene expression correlates with resistance to chemotherapy in different types of cancer.

The nucleotide sequence of the mdr1 gene (Gros, P. et al., Cell 47:371 (1986); Chen, C. et al., Cell 47:381 (1986)) indicates that it encodes a polypeptide similar or identical to P-glycoprotein and that these are members of the highly conserved class of membrane proteins similar to bacterial transporters and involved in normal physiological transport processes. Sequence analysis of the mdr1 gene indicates that Pgp consists of 1280 amino acids distributed between two homologous (43% identity) halves. Each half of the molecule has six hydrophobic transmembrane domains and each has an ATP binding site within the large cytoplasmic loops. Only about 8% of the molecule is extracellular, and the carbohydrate moiety (approximately 30 kDa) is bound to sites in this region.

Thus, it will be appreciated that mammalian cells having a "multidrug-resistance" or "multidrug-resistant" phenotype are characterized by the ability to sequester, export or expel a plurality of cytotoxic substances (e.g., chemotherapeutic drugs) from the intracellular milieu. Cells may acquire this phenotype as a result of selection pressure imposed by exposure to a single chemotherapeutic drug (the selection toxin). Alternatively, cells may exhibit the phenotype prior to toxin exposure, since the export of cytotoxic substances may involve a mechanism in common with normal export of cellular secretion products, metabolites, and the like. Multidrug resistance differs from simple acquired resistance to the selection toxin in that the cell acquires competence to export additional cytotoxins (other chemotherapeutic drugs) to which the cell was not previously exposed. For example, Mirski et al. (1987), 47 Cancer Res. 2594-2598, describe the isolation of a multidrug-resistant cell population by culturing the H69 cell line, derived from a human small cell lung carcinoma, in the presence of adriamycin (doxorubicin) as a selection toxin. Surviving cells were found to resist the cytotoxic effects of anthracycline analogs (e.g., daunomycin, epirubicin, menogaril and mitoxantrone), acivicin, etoposide, gramicidin D, colchicine and Vinca-derived alkaloids (vincristine and vinblastine) as well as of adriamycin. Similar selection culturing techniques can be applied to generate additional multidrug-resistant cell populations.

Accordingly, the pharmaceutical compositions of the invention can additionally include compounds which act to inhibit the MDR phenotype and/or conditions associated with MDR phenotype. Such compounds can include any known MDR inhibitor compounds in the art, such as, antibodies specific for MDR components (e.g. anti-MDR transporter antibodies) or small molecule inhibitors of MDR transporters, including specifically, tamoxifen, verapamil and cyclosporin A, which are agents known to reverse or inhibit multidrug resistance. (Lavie et al. J. Biol. Chem. 271: 19530-10536, 1996, incorporated herein by reference). Such compounds can be found in U.S. Pat. Nos. 5,773,280, 6,225,325, and 5,403,574, each of which are incorporated herein by reference. Such MDR inhibitor compounds can be co-administered with the anti-MN antibodies and/or fragments of the invention for various purposes, including, reversing the MDR phenotype following the detection of the MDR phenotype to assist or enhance a chemotherapeutic treatment. The MDR inhibitor, such as, for example, tamoxifen, verapamil or cyclosporin A, may be used in conjunction with the compounds of the invention to assist in the detection of the MDR phenotype. In accordance with this aspect, an MDR inhibitor can enhance the uptake and accumulation of a compound of the invention in an MDR cancer cell since the capacity of the MDR transport system in transporting or "pumping out" the imaging compound vis-a-vis the substrate domain would be diminished in the presence of an MDR inhibitor.

In yet another embodiment, the anti-MN antibodies and/or antibody fragments of the present invention are used in association with a gene therapy program in the treatment of cancer. Gene therapy with recombinant cells secreting interleukin-2 can be administered in combination with the inventive antibodies to prevent or treat cancer, particularly breast cancer (See, e.g., Deshmukh et al., 2001, J. Neurosurg. 94:287).

To assess the ability of a particular antibody to be therapeutically useful to treat cancer, as an example, the antibody may be tested in vivo in a mouse xenograft tumor model. If desired, MN antibodies may be converted into $IgG_1$ antibodies before therapeutic assessment. This conversion is described in Example 5, and an example of a therapeutic model is detailed in Example 9. Antibody activity may also be tested using an antibody dependent cell-mediated cytotoxicity assay as described in Example 12.

The present invention also provides diagnostic methods with which MN may be detected in a patient sample or biological sample. Such diagnostic methods may be used, for example, to diagnose disorders in which MN is elevated. Such disorders include, but are not limited to, carcinomas of the kidney, esophagus, breast, cervix, colon, and lung. When used for diagnosis, detection of an amount of the antibody-MN complex in a sample from a patient which is greater than an amount of the complex in a normal sample identifies the patient as likely to have the disorder. An immunohistochemical method for the detection of MN in cancer tissues is described in Example 11.

In another aspect of the invention, a method is provided for detecting and/or visualizing an MN-related cancer having an abnormally amount of expressed MN protein. Such methods can comprise contacting the MN-related cancer cell with an anti-MN antibody or fragment of the invention, and making an image using a medical imaging modality, wherein the anti-MN antibody or fragment comprises a label domain capable of being detected by the medical imaging modality.

The detection methods of the invention can be performed in vitro. The cancer cell or tissue can be from any suitable source, such as for example, a biopsy or a cell or tissue culture. Methods for obtaining biopsies and maintaining and/or propagating the removed tissues and/or cells will be well known to the skilled artisan. In vitro detection of multidrug resistance can have various applications, such as, for example, determining whether a particular subject's cancer, either before, during or after treatment, has developed a multidrug phenotype.

The type of imaging modality used to detect the compounds of the invention will depend on the particular label domain used in the inventive compounds. For example, if the label domain comprises a gadolinium chelate, then typically MRI could be used to detect the imaging agent of the invention. If a radionuclide chelate is used as the label domain, a nuclear imaging method could be used (e.g. PET). If a fluorescence-based label domain is used, an optical imaging system could be used, such as, for example a FACS system or fluorescence microscopy or a fluorescence automated plate reader. Choosing an appropriate imaging modality for use in the in vitro detection methods of the invention are completely within the knowledge of the skilled artisan.

In addition, the amount of imaging agent used in the in vitro detection methods of the invention will be determined by one of ordinary skill in the art and can depend on the degree to which the MDR phenotype is present, e.g. the level of expression of the MDR transport system (e.g. the P-glycoprotein). The skilled artisan can determine what amount of the novel imaging compounds that is sufficient for detecting a MDR phenotype without undue experimentation, i.e. a detectably sufficient amount.

The type of imaging modality used is not limited to any particular type, and can include, for example MRI, nuclear imaging (e.g. PET or SPECT), optical imaging, sonoluminence imaging or photoacoustic imaging (ultrasound). The skilled artisan will appreciate that the particular label domain of the imaging compounds of the invention should be compatible with the particular imaging modality being used.

In a preferred embodiment, the methods of detection utilize anti-MN antibodies or fragments thereof and appropriate labels that are capable of being detected by MRI. For example, the antibodies or fragments of the invention can comprise a label domain that is a MR contrast agent, such as, for example a paramagnetic metal chelate or chelates or any of those described herein: The imaging agent can also comprise a radionuclide label domain for imaging or detecting by a nuclear imaging modality, such as, positron emission tomography (PET) or single photon emission computer tomography (SPECT), e.g. a radionuclide such as, for example, $^{199}$Au, $^{72}$As, $^{141}$Ce, $^{67}$Cu, $^{60}$Cu, $^{52}$Fe, $^{67}$Ga, $^{68}$Ga, $^{51}$Gr, $^{111}$In, $^{177}$Lu, $^{51}$Mn, $^{203}$Pb, $^{188}$Re, $^{97}$Ru, $^{47}$Sc, $^{177m}$Sn, $^{94m}$Tc, $^{167}$Tm, and $^{90}$Y. The radionuclide can be chelated by a suitable chelator, or by multiple chelators, such as, for example HYNIC, DRPA, EDTA, DOTA, TETA, DTPA and BAT. Conditions under which a chelator will coordinate a metal are described, for example, by Gansow et al., U.S. Pat. Nos. 4,831,175, 4,454,106 and 4,472,509, each of which are incorporated herein by reference. $^{99m}$Tc (Technetium-99m) is a particularly attractive radioisotope for therapeutic and diagnostic applications, as it is generally available to nuclear medicine departments, is inexpensive, gives minimal patient radiation doses, and has ideal nuclear imaging properties.

The patient sample may be contacted with an antibody of the invention, and the patient sample may then be assayed for the presence of an antibody-MN complex. As described above, the antibody may comprise a detectable label, such as a fluorescent, radioisotopic, chemiluminescent, or enzymatic label, such as horseradish peroxidase, alkaline phosphatase, or luciferase.

Optionally, the antibody may be bound to a solid support, which may accommodate automation of the assay. Suitable solid supports include, but are not limited to, glass or plastic slides, tissue culture plates, microliter wells, tubes, silicon chips, or particles such as beads (including, but not limited to, latex, polystyrene, or glass beads). Any method known in the art may be used to attach the antibody to the solid support, including use of covalent and non-covalent linkages, passive absorption, or pairs of binding moieties attached to the antibody and the solid support. Binding of MN and the antibody may be accomplished in any vessel suitable for containing the reactants. Examples of such vessels include microliter plates, test tubes, and microcentrifuge tubes.

Pharmaceutical Compositions and Dosages

The antibodies described herein may be provided in a pharmaceutical composition comprising a pharmaceutically acceptable carrier. The pharmaceutically acceptable carrier may be non-pyrogenic. The compositions may be administered alone or in combination with at least one other agent, such as stabilizing compound, which may be administered in any sterile, biocompatible pharmaceutical carrier including, but not limited to, saline, buffered saline, dextrose, and water. A variety of aqueous carriers may be employed including, but not limited to saline, glycine, or the like. These solutions are sterile and generally free of particulate matter. These solutions may be sterilized by conventional, well-known sterilization techniques (e.g., filtration).

Generally, the phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water, isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the antibody compositions of the invention.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The compositions may contain pharmaceutically acceptable auxiliary substances as required to approximate physiological conditions such as pH adjusting and buffering agents, and the like. The concentration of the antibody of the invention in such pharmaceutical formulation may vary widely, and may be selected primarily based on fluid volumes, viscosities, etc., according to the particular mode of administration selected. If desired, more than one type of antibody may be included in a pharmaceutical composition (e.g., an antibody with different $K_d$ for MN binding).

The compositions may be administered to a patient alone, or in combination with other agents, drugs or hormones. In addition to the active ingredients, these pharmaceutical compositions may contain suitable pharmaceutically acceptable carriers comprising excipients and auxiliaries that facilitate processing of the active compounds into preparations which may be used pharmaceutically. Pharmaceutical compositions of the invention may be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means.

The compositions of the invention additionally contemplate suitable immunocarriers, such as, proteins, polypeptides or peptides such as albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein-derived or non-protein derived substances are known to those skilled in the art.

In aspects involving vaccines, e.g. cancer vaccines together with the antibodies of the invention, the compositions of the invention can be administered with or without an adjuvant. Administration can be carried out in the absence of an adjuvant in order to avoid any adjuvant-induced toxicity. The person of ordinary skill in the art to which this invention pertains, e.g. a medical doctor specializing in cancer, will appreciate and understand how to ascertain whether an adjuvant should or should not be used and can dependent upon the medical history of a subject, family data, toxicity data, allergy-related test results, etc. In embodiments where an adjuvant is used, it is advantageous that the adjuvant promotes the formation of protective antibodies, such as protective IgG antibodies. Any suitable adjuvant known to one of ordinary skill in the art is contemplated by the present invention and are readily adapted to this invention. Suitable adjuvants for use in vaccinating animals can include, but are not limited to, aluminum hydroxide, aluminum hydroxide, saponin and its purified component Quit A, complete Freund's adjuvant (CFA) and incomplete Freund's adjuvant (IFA). Dextran sulfate has been shown to be a potent stimulator of $IgG_2$ antibody against staphylococcal cell surface antigens, and also is suitable as an adjuvant. It will be appreciated by the skilled person that some adjuvants can be more preferable for veterinary application, whereas other adjuvants will be preferable for use in humans, and that adjuvant toxicities are a consideration that should be made by the skilled person prior to administration of the compound to a human.

Formulations suitable for parenteral, subcutaneous, intravenous, intramuscular, and the like; suitable pharmaceutical carriers; and techniques for formulation and administration may be prepared by any of the methods well known in the art (see, e.g., Remington's Pharmaceutical Sciences, Mack Publishing Co., Easton, Pa., $20^{th}$ edition, 2000). Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The determination of a therapeutically effective dose is well within the capability of those skilled in the art. A therapeutically effective dose refers to the amount of an antibody that may be used to effectively treat a disease (e.g., cancer) compared with the efficacy that is evident in the absence of the therapeutically effective dose.

The therapeutically effective dose may be estimated initially in animal models (e.g., rats, mice, rabbits, dogs, or pigs). The animal model may also be used to determine the appropriate concentration range and route of administration. Such information may then be used to determine useful doses and routes for administration in humans.

Therapeutic efficacy and toxicity (e.g., $ED_{50}$—the dose therapeutically effective in 50% of the population and $LD_{50}$—the dose lethal to 50% of the population) of an antibody may be determined by standard pharmaceutical procedures in cell cultures or experimental animals. The dose ratio of toxic to therapeutic effects is the therapeutic index, and it may be expressed as the ratio, $LD_{50}/ED_{50}$. The data obtained from animal studies may used in formulating a range of dosage for human use. The dosage contained in such compositions may be within a range of circulating concentrations that include the $ED_{50}$ with little or no toxicity. The dosage varies within this range depending upon the dosage form employed, sensitivity of the patient, and the route of administration.

The exact dosage may be determined by the practitioner, in light of factors related to the patient who requires treatment. Dosage and administration may be adjusted to provide sufficient levels of the antibody or to maintain the desired effect. Factors that may be taken into account include the severity of the disease state, general health of the subject, age, weight, and gender of the subject, diet, time and frequency of administration, drug combination(s), reaction sensitivities, and tolerance/response to therapy.

Polynucleotides encoding antibodies of the invention may be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 μg to about 500 μg/kg of patient body weight. For administration of polynucleotides encoding the antibodies, effective in vivo dosages are in the range of about 100 ng to about 500 μg of DNA.

The mode of administration of antibody-containing pharmaceutical compositions of the present invention may be any suitable route which delivers the antibody to the host. As an example, pharmaceutical compositions of the invention may be useful for parenteral administration (e.g., subcutaneous, intramuscular, intravenous, or intranasal administration).

All patents and patent applications cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLES

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention

Example 1

Construct of Human Combinatorial Fab Library (HuCAL Gold)

HuCAL® GOLD is an antibody library based on HuCAL® technology (Human Combinatorial Antibody Library; MorphoSys AG, Martinsried/Planegg, Germany). The library combines a synthetic, fully human antibody library in the Fab format featuring six diversified CDR regions with an display technology for the selection of high affinity antibodies, Cys-Display™ (MorphoSys AG, Martinsried/Planegg, Germany). CysDisplay™ is a monovalent phage display technology based on a phenotype-genotype linkage via disulfide bonds, which allows the recovery of specific antibodies with high affinities.

The phage display vector pMORPH®23 is a phagemid vector allowing monovalent CysDisplay™ of Fab fragments. It encodes the full length gIIIp, the Fd chain ($V_H$-$C_H$1), and the light chain ($V_L$-$C_L$), all of which are equipped with different secretory signal sequences which directs the corresponding protein chain to the periplasm of E. coli. Both ompA and phoA signal sequences are utilized to transport the heavy and light chains to the periplasm, where the chains assemble via non-covalent interactions occurs. This display vector carries an inducible lac promotor/operator region. The laqI$^q$ gene product for repression of expression is supplied by the E. coli host strain TG1. Induction of Cys-gIIIp and Fab expression is achieved by the addition of IPTG (isopropyl-β-D-thio-galacto-pyranoside). The enriched Fab pools were sub-cloned from pMORPH®23 to the Fab expression vector pMORPH®x9 using the restriction enzymes XbaI and EcoRI. By this step, the cysteine and the linker-His6 part at the C-terminus of the Fd chain were removed and the gIIIp is excised. The expression vector pMORPH®x9_Fab_FH provides two C-terminal tags a FLAG and 6×His thus facilitating detection and purification of the Fab proteins.

Phagemid Rescue and Phage Amplification

The HuCAL GOLD Fabs phagemid in TG1 cells were amplified in 2×TY media supplemented with 34 μg/ml chloramphenicol and 1% glucose. After helper phage infection (VCSM13 ~2-6×10$^{11}$ pfu/ml) at 37° C. for 30 minutes, TG1 cells were concentrated by centrifugation. The phage were amplified by incubation of the infected TG1 cells at 22° C. overnight in 2×TY media containing 34 μg/ml chloramphenicol, 50 μg/ml kanamycin, and 0.25 mM IPTG. The phage containing supernatant was used for the phase panning.

Example 2

Solid Phase Panning

Solid phase panning was carried out by coating MaxiSorp™ plates (Nalgene Nunc International, Rochester, N.Y.) or Dynabeads™ (Invitrogen, Carlsbad, Calif.) with human MN protein in PBS (1 μg/well or 1 μg/1 mg of beads). The MN protein represents the entire extra-cellular domain of the protein with a C-terminal histag for purification. The MN protein was expressed in a mammalian cell line HKB-11 and purified by Ni-NTA chromatography using standard methods that are well known to those skilled in the art. Wells containing bound MN protein were blocked with 5% milk in PBS, washed in PBS followed by a 2 hour incubation at room temperature with an aliquot of pre-blocked HuCAL GOLD phage library containing 1×10$^{12}$ HuCAL GOLD Fab phage. Bound phage were washed and then eluted with 20 mM DTT in 10 mM Tris buffer at pH 8.0. Three rounds of panning were performed with phage amplification conducted between each round as described above. Wash stringency was increased between each round of panning to decrease nonspecific binding.

Example 3

Subcloning of Selected Fab Fragments for Expression in E. coli

The selected Fabs were cloned from the pMORPH®23 display vector to the pMORPH®x9_Fab_FH expression vector to facilitate rapid expression of soluble Fab for ELISA screening. The DNA preparation of the pMORPH®23 vector was digested with EcoRI and XbaI, thus cutting out the entire Fab-encoding fragment (ompA-VL-VL and phoA-Fd). After subsequent purification, the fragment was ligated to the prepared pMORPHx9_Fab_FH vector (also digested with EcoRI/XbaI and purified). The vector containing the Fab insert was transfected into competent E. coli TG1 F-cells by electroporation. The transformed E. coli cell were grown on LB plates containing 34 μg/ml chloramphenicol and 1% glucose o/n at 37° C. Colonies were picked and placed in culture media containing 34 μg/ml chloramphenicol and 1% glucose. Glycerol was added to 20% and these stock starter cultures were stored at −80° C. until needed for ELISA. To obtain purified Fabs, E. coli transformants carrying this vector were grown typically in multiples of 1 L shake flask cultures, harvested, and purified using Ni-NTA affinity chromatography using methods well known to those skilled in the art.

Example 4

Identification of MN-Binding Fab Fragments by ELISA

Maxisorp 96-well ELISA plates were coated with 100 μl/well of a solution of purified human MN protein at a concentration of 5 μg/ml in PBS. Fabs were expressed using E. coli transformants grown in 2×TY media containing 34 μg/ml chloramphenicol from started stock cultures. Twelve (12) hours prior to harvest Fab expression was induced by addition of IPTG (0.5 mM final concentration). Cells were lysed and 100 μl lysate was incubated within the well of an MN-precoated and milk-blocked Maxisorp plate for 2 hours at room temperature. Plates were then washed in TBS and Tween containing-TBS to remove nonspecific binding. Bound Fabs were detected with goat anti-human (Fab')$_2$ antibody conjugated to alkaline phosphatase (Pierce Chemical, Rockford, Ill.). The substrate AttoPhos (Roche Diagnostics, Alameda, Calif.) was used as directed in the manufacturers instructions, excitation was at 430 nm and emission was read at 535 nm.

A large number of *E. coli* transformants expressed Fabs that exhibited a signal to noise ration in the ELISA of >10. DNA sequencing of the VH and VL regions identified over 50 unique MN-binding Fabs. The DNA and protein sequences of the entire VH and VL of ten antibodies based upon their functional properties is shown in FIGS. 3 and 4, respectively. Each of these ten disclosed antibodies bound by ELISA to the purified MN protein isolated from a mammalian expression cell line, HKB-11 (FIG. 5). The antibodies examined also reacted with purified MN isolated from sf9 insect cells that had been infected with a baculovirus encoding the extracellular domain of MN, (FIG. 5) demonstrating that the ELISA interactions were specific for the MN protein and not any trace contaminants in the protein preparations. In a BIAcore™ assay, antibodies of the present invention specifically bind to human MN with a $K_d$ in the range from 1 nM ($1 \times 10^{-9}$ M) to about 50 nM ($5.0 \times 10^{-8}$ nM) (FIG. 5).

Example 5

Identification of MN-binding Fabs and IgGs

The binding interactions between MN protein and the antibodies of this invention were analyzed using surface plasmon resonance technology on a BIAcore 3000 instrument (BIAcore, Uppsala, Sweden). For the binding of full-length IgGs (1e4, 1aa1, and 3ee9), goat anti-human IgG Fc was covalently coupled to the CM5 biosensor chip at high density using a standard amine coupling kit (BIAcore, Uppsala, Sweden). A capture assay was then used to bind these IgG to the anti-human IgG Fc-immobilized surface, aiming for a 300 response unit BIAcore signal. The BIAcore was operated at 25° C. and a flow rate of 10 μl/min running buffer containing PBS/0.05% Tween 20, or containing 10 mM Na-HEPES, pH 7.5/150 mM NaCl/3 mM. EDTA/0.005% Tween 20. After ligand binding, the flow rate was then increased to 25 μl/min and various concentrations of MN analyte (e.g., range of 50 nM to 1 nM) were flowed over the surface for 10 minutes such that the association phase could be monitored. Dissociation then proceeded for 35 minutes, followed by regeneration of the anti-human IgG Fc-immobilized surface at 100 n with 100 μl of 10 mM phosphoric acid. Sensorgrams were fitted using a 1:1 Langmuir binding model to calculate rate constants. The binding of Fabs to MN was similarly determined except that an anti-human-Fab IgG was immobilized onto the chip and used to capture the Fabs prior to the assessment of MN binding. FIG. 5 shows the resulting binding constants for the binding of the disclosed antibodies to purified MN protein. Each of the antibodies bound MN exhibiting Kd values that ranged between 0.15 and 50 nM.

Example 6

Construction of HuCAL Immunoglobulin Expression Vectors for Transient Expression Antibody Expression in 293 F Cells Heavy chain expression vector. The multiple cloning site of pcDNA3.1+ (Invitrogen, Carlsbad, Calif.) was removed (NheI/ApaI), and a site compatible with the restriction sites used for HuCAL was inserted for the ligation of the leader sequences (NheI/EcoRI), VH-domains (EcoRI/B1pI), and the immunoglobulin constant regions (B1pI/ApaI). The leader sequence (EMBL M83133) was equipped with a Kozak sequence (Kozak, Nucleic Acid Res. 15:8125-8148, 1987). The constant regions of human IgG1 (PIR J00228), IgG4 (EMBL K01316), and serum IgA1 (EMBL J00220) were dissected into overlapping oligonucleotides with lengths of about 70 bases. Silent mutations were introduced to remove restriction sites non-compatible with the HuCAL design. The oligonucleotides were spliced by overlap extension-PCR.

Light chain expression vectors. The multiple cloning site of pcDNA3.1/Zeo+ (Invitrogen, Carlsbad, Calif.) was replaced by two different sites. The κ-site provided restriction sites for insertion of a κ-leader (NheI/EcoRV), HuCAL-scFv Vk-domains (EcoRV/BsiWI,) and the κ-chain constant region (BsiWI/ApaI). The corresponding restriction sites in the λ-site were NheI/EcoRV (l-leader), EcoRV/HpaI (Vl-domains), and HpaI/ApaI (λ-chain constant region). The κ-leader (EMBL Z00022) as well as the λ-leader (EMBL L27692) were both equipped with Kozak sequences. The constant regions of the human κ-chain (EMBL J00241) and λ-chain (EMBL M18645) were assembled by overlap extension-PCR as described above.

Generation of full-length IgG from Fabs. Fab heavy chain sequence contained within the *E. coli* expression vector pMORPHx9_Fab_FH was excised by cutting with MfeI/B1pI and ligated into the heavy chain expression vector described above that had been cut with EcoRI/B1pI. Fab kappa light chain sequence contained within pMORPHx9_Fab_FH was excised with EcoRV/BsiWI and ligated into the Kappa light chain expression vector described above that had also been cut with EcoRV/BsiWI. Fab lambda light chain sequence contained within pMORPHx9_Fab_FH was excised with EcoRV/HpaI and ligated into the lambda expression vector described above.

Large scale transient expression of full-length IgGs. Cell-bag 20 L/0 (Wave Biotech LLC, Somerset, N.J.) were seeded with $0.25 \times 10^6$ 293F cells/ml (Invitrogen) in 9.3 L Freestyle 293 expression medium (Invitrogen). Cells were grown to a density of $1 \times 10^6$/ml and transfected by the addition of 5 mg each of the light chain expression vector and heavy chain expression vector encoding the full length antibody in 350 ml Optimem (Invitrogen) containing 293fectin reagent (Invitrogen). Following fermentation for 96 hours at 37° C., cell culture supernatant was harvested by centrifugation, sterile filtered, concentrated by tangential flow filtration adjusted to pH 7.6 and then subjected to standard protein A column chromatography (Amersham Pharmacia Biotech, Piscataway, N.J.).

Example 7

Cell Adhesion Assay

Fifty (50) μL of a 1 μg/mL solution of purified MN in PBS was adsorbed onto a non-treated 96-well plate overnight at 4° C. The solution was removed, and the wells rinsed 3× with PBS. The wells were blocked for 1 hour with 200 μL 50% FBS in RPMI1640 media. The wells were then treated with 100 μg 1e4 anti-MN antibody in 1% BSA in PBS, control IgG in 1% BSA in PBS or 1% BSA in PBS. After washing with PBS, 5000 MaTu cells (MN+ cells) were added to the wells and the plate incubated overnight at 37° C. at 5% $CO_2$. The ability of anti-MN antibodies to block adhesion of MaTu cells to MN-coated wells was assessed after washing with PBS. An example of this experiment is shown in FIG. 6 where 100 µg of anti-MN antibody 1e4 inhibits cell adhesion, whereas control IgG or the buffer vehicle does not.

Example 8

Subcutaneous Xenograft Cancer Model with Immunoconjugate

Anti-MN antibodies were conjugated to cytotoxic small molecules using protocols that are known in the art (e.g., Liu, et al., Proc. Natl. Acad. Sci. 93:8618-'8623, 1996.). Human mammary xenograft, MaTu cells were maintained as adherent cultures in RPMI supplemented with 10% FBS. Ncr nude mice (8-12 weeks of age) were inoculated subcutaneously in the right flank with $5 \times 10^6$ cells in 0.1 mL of 80% matrigel/20% HBSS. When tumors reached an average size of ~180 mg (6 days), treatment was initiated. Monoclonal antibodies conjugated to cytotoxic small molecules were administered i.v. once every four days (Q4Dx3) at a dose of 10 mg/kg. Control mice were treated with PBS or an unconjugated monoclonal antibody. Daily examinations into the health status of each animal were conducted. Each experimental group consisted of 10 mice and the dosing volume was 0.1 mL/10 g body weight. The length and width of each tumor was measured by using an electronic caliper 2-3 times per week and tumor weights (mg) were calculated based on the formula of [length (mm)×width $(mm)^2$]/2. All data, including daily observations, obtained throughout the course of the study were documented. Tumor growth inhibition (TGI) was calculated as 1-T/C×100, where T=final tumor weights from a treated group, and C=final tumor weights from the control group. FIG. 7 shows that the monoclonal IgG1 1e4 when conjugated to a cytotoxic drug produced a significant anti-tumor effect at 30 mg/kg immunoconjugate, whereas the unconjugated antibody had no effect. These data demonstrate that the therapeutic utility of antibodies directed against MN protein as vehicles for cytotoxic drug delivery to tumors.

Example 9

Fluorescence-activated Cell Sorting Assay (FACS Assay)

Figure 8:
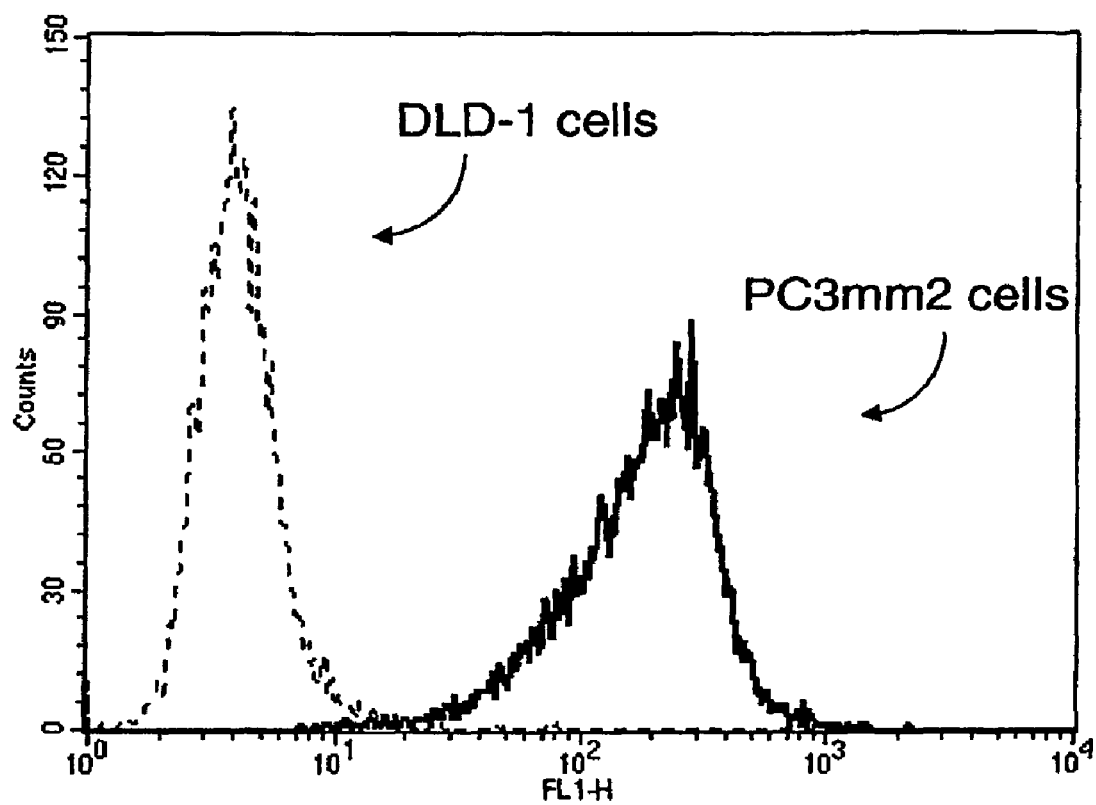
FIG. 8 depicts the FACS measurement of binding of an anti-MN antibody to the PC3mm2 cell line which expresses the MN protein on its surface.

Cells may be assayed for MN expression as a diagnostic tool. Adherent MN-expressing PC-3 mm2 cells and non-MN expressing DLD1 cells were detached from their flasks with 1:10 trypsin/Versene in PBS solution for 5 to 10 minutes. Cells were spun down (1000 rpm, 5 minutes), washed once with ice cold RPMI 10% FBS, and resuspended in ice-cold staining buffer ($Ca^+Mg^+$-free PBS, 2% BSA, and 0.05% sodium azide) at $6 \times 10^6$ cells/ml. Primary antibody, human anti-MN IgG1, or control human IgG1 antibody at 25 µg/mL were incubated with $6 \times 10^5$ cells on ice for 1 hour. The unbound antibody was washed from the cells with the ice-cold staining buffer. The cells were fixed with 2% formaldehyde in PBS for 10 minutes, then washed twice with staining buffer. The cell pellet was resuspended in 100 µl ice cold staining buffer containing anti-human Alexa fluor 488 secondary antibody (final conc. 1:200, Molecular Probes/Invitrogen, Carlsbad, Calif.), and incubated on ice for 1 hour. The unbound antibody was washed from the cells two times with flow buffer (PBS containing 2% BSA), and the cells were resuspended in 1 mL flow buffer. FACS analysis of the resuspended cells was performed on a Beckman FACS Caliber instrument. FIG. 8 shows that PC-3 mm2 human prostate cancer cells expressed MN as assayed by FACS, whereas DLD-1 cells did not.

Example 10

Antibody-dependent Cell Mediated Cytotoxicity Assays (ADCC Assays)

Anti-tumor activity of anti-MN IgGs may be mediated by ADCC activity. MN-expressing PC-3 mm2 cells and non-MN expressing HCT-116 cells are incubated with 250 ng/mL, 1000 ng/mL, or 2000 ng/mL human anti-MN IgG1, or control human IgG1 anti-digoxin antibody. Human PBMCs are added to these cells at effector: target ratios of 50:1, 25:1, and 5:1 ratios. A chromium-51 release assay is performed to determine the level of target cell lysis. A small amount of lysis is observed upon incubation of control antibody or no antibody in the presence of DLD and PC-3 mm2 cells. This spontaneous level of lysis is 10-15%, 5-10%, or 2-3% for 50:1, 25:1, and 5:1 target effector ratios, respectively. Similarly, lysis of non-MN expressing DLD cells was in the 0-10% range when incubated with the anti-MN antibodies. However, lysis of PC-3 mm2 cells when incubated with the human anti-MN IgGs was significantly higher than the controls. Lysis of 40, 50, and 60% was observed when using 250 ng/mL, 1000 ng/mL, and 2000 ng/mL at 50:1 target:effector ratios. Similarly, 30, 33, and 38% lysis was observed at 25:1 ratios, and finally, 8, 10, and 15% lysis was observed at 5:1 target:effector ratios. These experiments show that human anti-MN antibodies mediate anti-tumor ADCC activity and may be used for the therapeutic treatment of cancer.

Example 11

Immunoconjugate

Preparation

Figure 9:
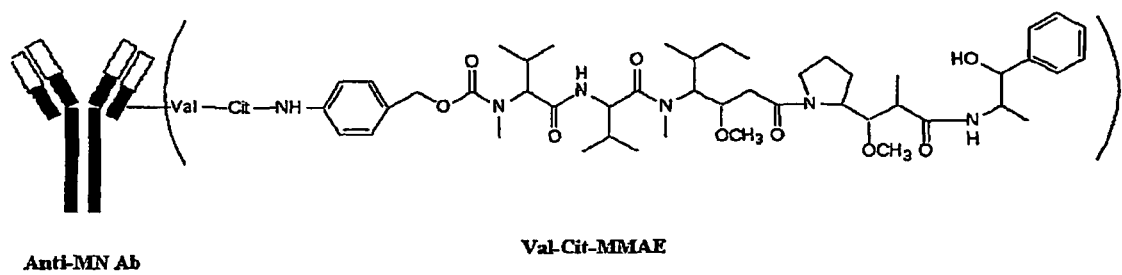
FIG. 9 schematically depicts the antibody conjugate (anti-MN antibody conjugated to MMAE)

A human antibody directed at the MN cell surface antigen was generated using a phage display library that encodes a diversity of human Fabs (Morphosys). This antibody was conjugated to Monomethylauristatin E (MMAE) (Fransisco et al., Blood, 2003, 102:1458-1465) (FIG. 9).

In Vitro Activity and Selectivity

The antibody portion of 3ee9/MMAE (3ee9) was identified by in vitro "panning" of a purified extracellular domain of human MN against the MorphoSys phage library composed of $10^{10}$ human Fab fragments (Fabs are the antigen binding portions of antibodies). The active Fabs were further examined for their capacity to selectively bind and undergo internalization upon addition to MN positive cells. The resulting active Fabs were then converted to full length human IgG1 antibodies, expressed in CHO cells, purified and then conjugated to the toxophore, MMAE (Liu et al, Proc Natl Acad Sci, 1996, 93:8618-8623). The conjugated antibodies were then tested for their ability to kill MN expressing cells. From a panel of seven full-length antibodies tested, 3ee9/MMAE was selected based on its binding properties, selectivity and potency in both in vitro and in vivo assays.

Surface Plasmon Resonance (Biacore) Materials and Methods

Binding interactions between HKB11-expressed human MN protein and human full-length anti-MN MAbs were analyzed using surface plasmon resonance technology on a BIAcore 3000 instrument (BIAcore, Uppsala, Sweden). For chip preparation, goat anti-human IgG Fc was covalently coupled to the CM5 biosensor chip using the standard amine coupling kit (BIAcore, Uppsala, Sweden). A capture assay was then used to bind the antibodies of interest to the anti-human IgG Fc-immobilized surface, aiming for a 300 response unit BIAcore signal. The BIAcore was operated at 25 C with a flow rate of 10 ul/min and running buffer containing 10 mM Na-HEPES, pH 7.5/150 mM NaCl/3 mM EDTA/0.005% Tween 20. After ligand binding, flow rate was increased to 25 ul/min and MN analyte (50 nM to 1 nM) was flowed over the surface for 10 min such that the association phase could be monitored. Dissociation then proceeded for 35 min, followed by regeneration of the anti-human IgG Fc-immobilized surface at 100 ul/min with 10 mM phosphoric acid. Sensorgrams were fitted using a 1:1 Langmuir binding model to calculate rate constants (Table 1, below).

TABLE 1

Affinity of panning-derived antibodies to the soluble MN determined by surface plasmon resonance (Biacore)

|  | 1E4 | 3EE9 | 1AA1 | 3A4 | 5AA3 | 3EF2 |
|---|---|---|---|---|---|---|
| Affinity (Kd, nM) | 5 | 4 | 27 | 1 | 1 | 6 |

Antibody Binding

3ee9/MMAE was shown to have a kD of 3.6 nM for purified MN protein using Biacore technology, which was the same as the affinity of the unconjugated antibody 3ee9. The binding to MN (CA IX) appeared specific, as there was no detectable binding to 13 other carbonic anhydrases. Binding to mitochondria-associated CA5 was observed, but this isozyme would be inaccessible to the antibody in vivo.

Figure 10A:
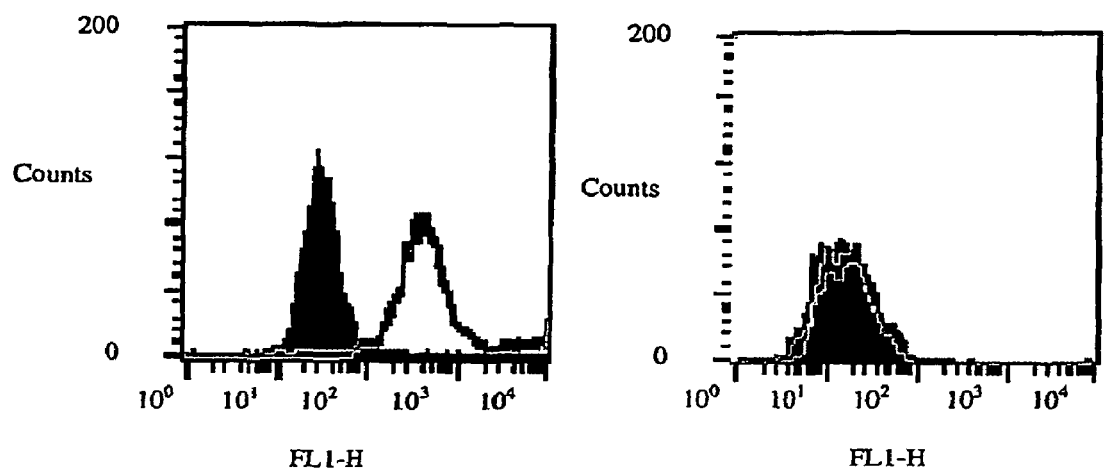
FIG. 10a shows FACS plots depicting 3ee9/MMAE binding to MN+ (MaTu) cells, but not to MN− (DLD) cells.

By FACS analysis, 3ee9/MMAE was shown to bind to MN-expressing MaTu cells, but not MN-negative DLD cells (FIG. 10a). The MN antibody G250, a humanized IgG1 antibody, (Wilex) was used as a reference throughout the in vitro studies. It bound MN with a Kd of 5.3 nM and exhibited a similar binding profile to MN+ and MN− cell lines as 3ee9/MMAE.

Figure 10B:
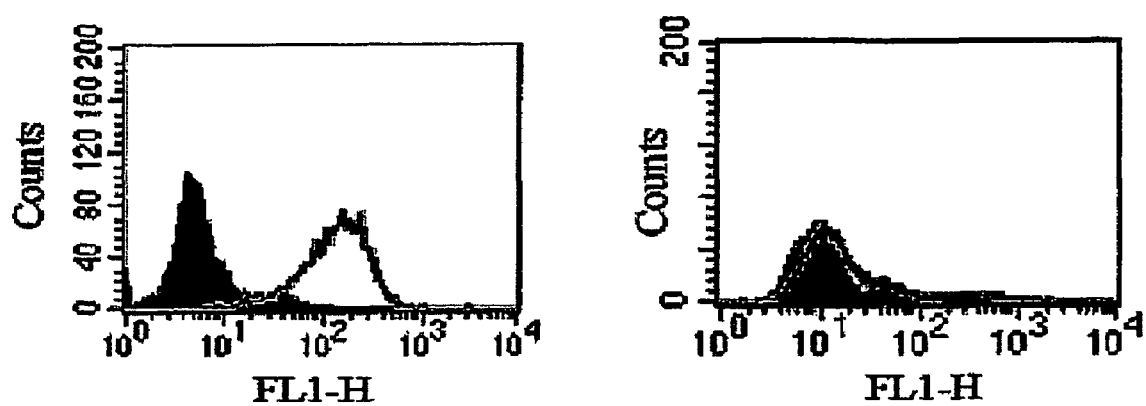
FIG. 10b shows FACS plots depicting 1E4 immunoconjugate binding to MN+ (PC3mm2) cells, but not to MN− (DLD) cells.
Figure 10C:
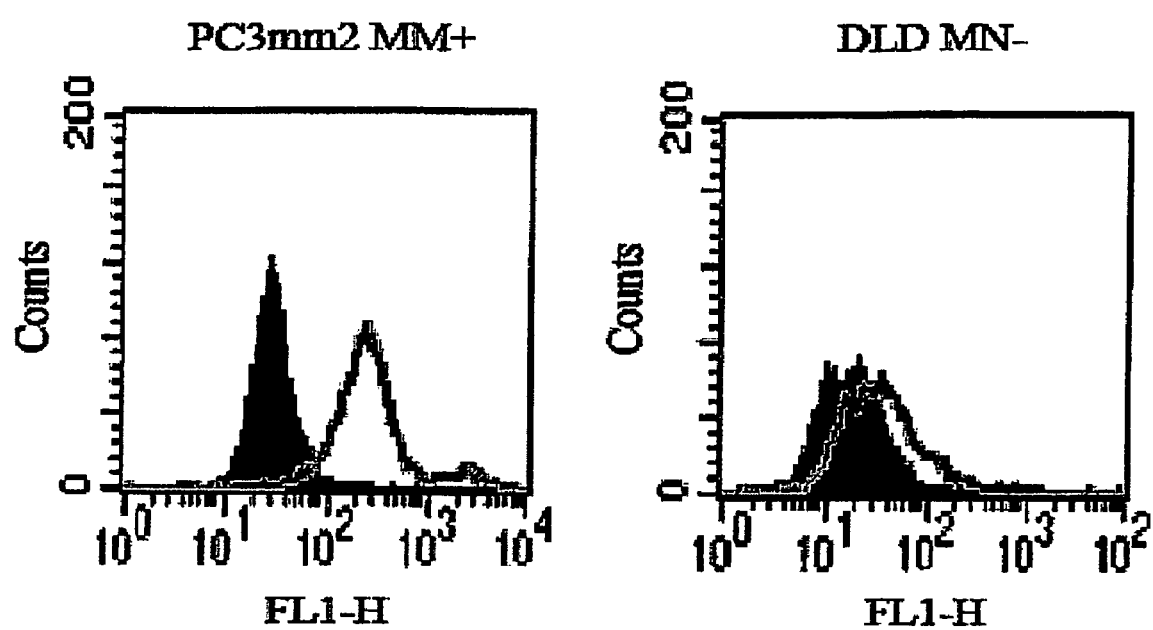
FIG. 10c shows FACS plots depicting 1aa1 immunoconjugate binding to MN+ (PC3mm2) cells, but not to MN− (DLD) cells.

Similar results were obtained for the antibody 1E4 and 1aa1 immunoconjugates (FIGS. 10b and 10c, respectively), which exhibited binding to MN+ cells, but not to MN− cells.

Antibody Internalization

Figure 11A:
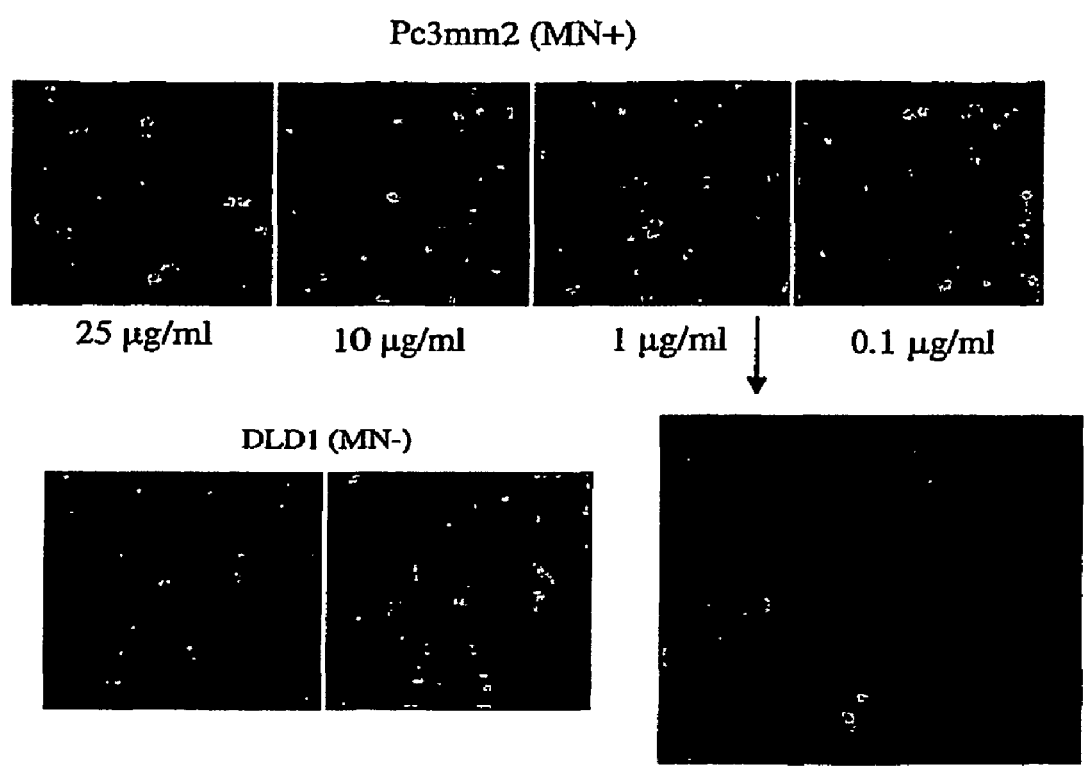
FIG. 11a shows immunofluorescence images depicting internalization of 3ee9/MMAE by MN+ cells and lack of internalization by MN− cells. Internalized 3ee9/MMAE is shown as fluorescence.

3ee9/MMAE was selectively internalized by MN-expressing cells (PC3mm2), but not by MN-negative cells (DLD1), as measured by Cellomics (FIG. 11a). Similarly, the 1E4 immunoconjugate was found to be internalized by MN+ cells (PC3mm2), but not by MN− (DLD1) cells (FIG. 11b).

Immunoprecipitation

Figure 12:
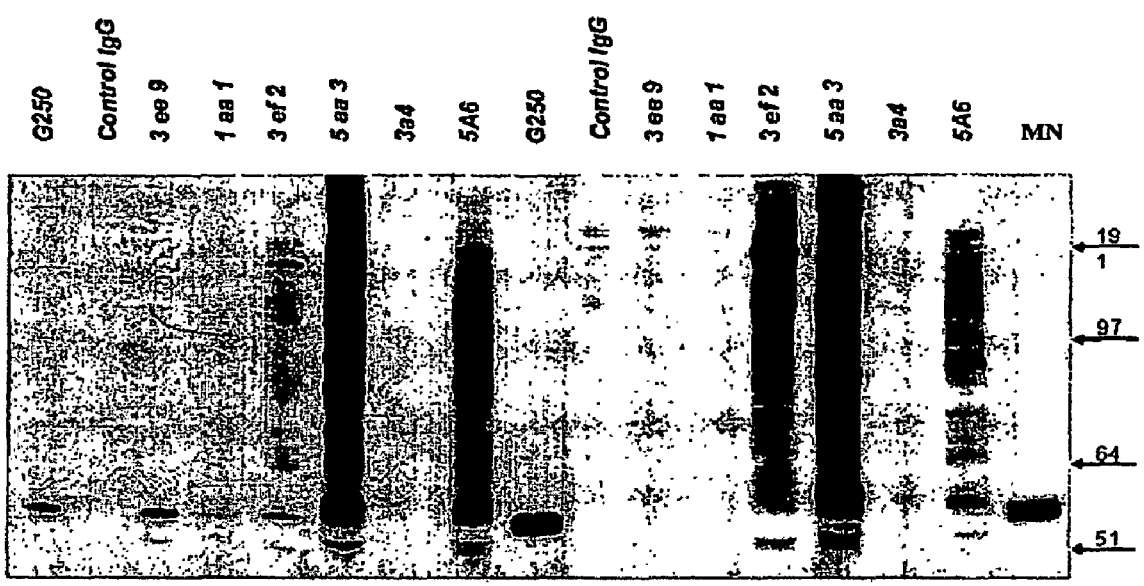
FIG. 12 shows an immunoblot depicting specific immunoprecipitation of biotinylated cell surface proteins by MN antibodies.

To further explore specificity, various candidate antibodies including the antibody portion of 3ee9/MMAE (3ee9) and the reference antibody G250 were incubated with cell lysates of MN+ (Pc3 mm2) and MN− (DLD-1) cell lines that had been selectively labeled with biotin. Complexes between the antibodies and cellular proteins were immunoprecipitated and the co-precipitated antigens visualized using immunoblots developed with enzyme-linked streptavidin. Both G250 and the 3ee9 antibody of 3ee9/MMAE selectively bound and co-immunoprecipitated with a single band of the same size as MN from MN+ cells (FIG. 12). Less specific antibodies such as 3ef2, 5aa3 and 5A6 co-immunoprecipitated several other proteins in addition to MN.

Cytotoxicity

Figure 13A:
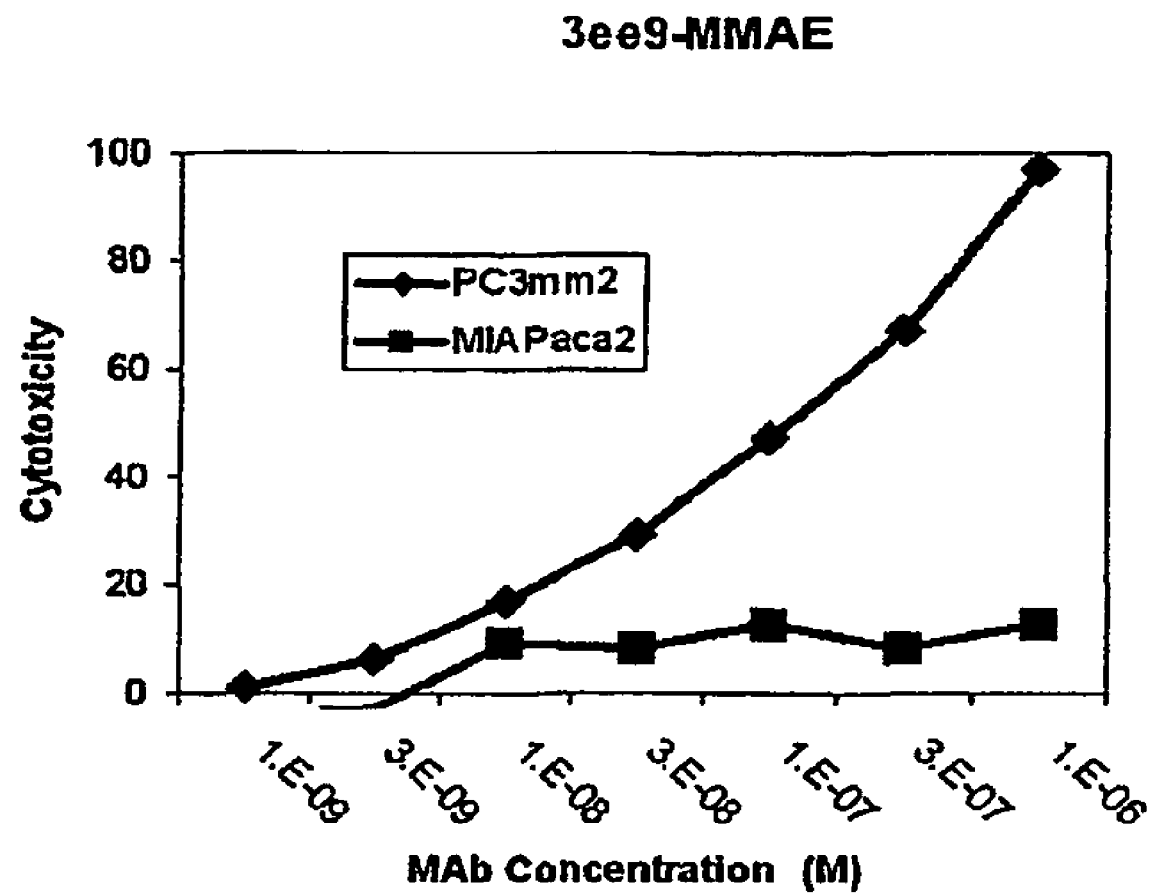
FIG. 13a graphically depicts the cytotoxicity of 3ee9/MMAE against MN+, but against MN−, cells.
Figure 13B:
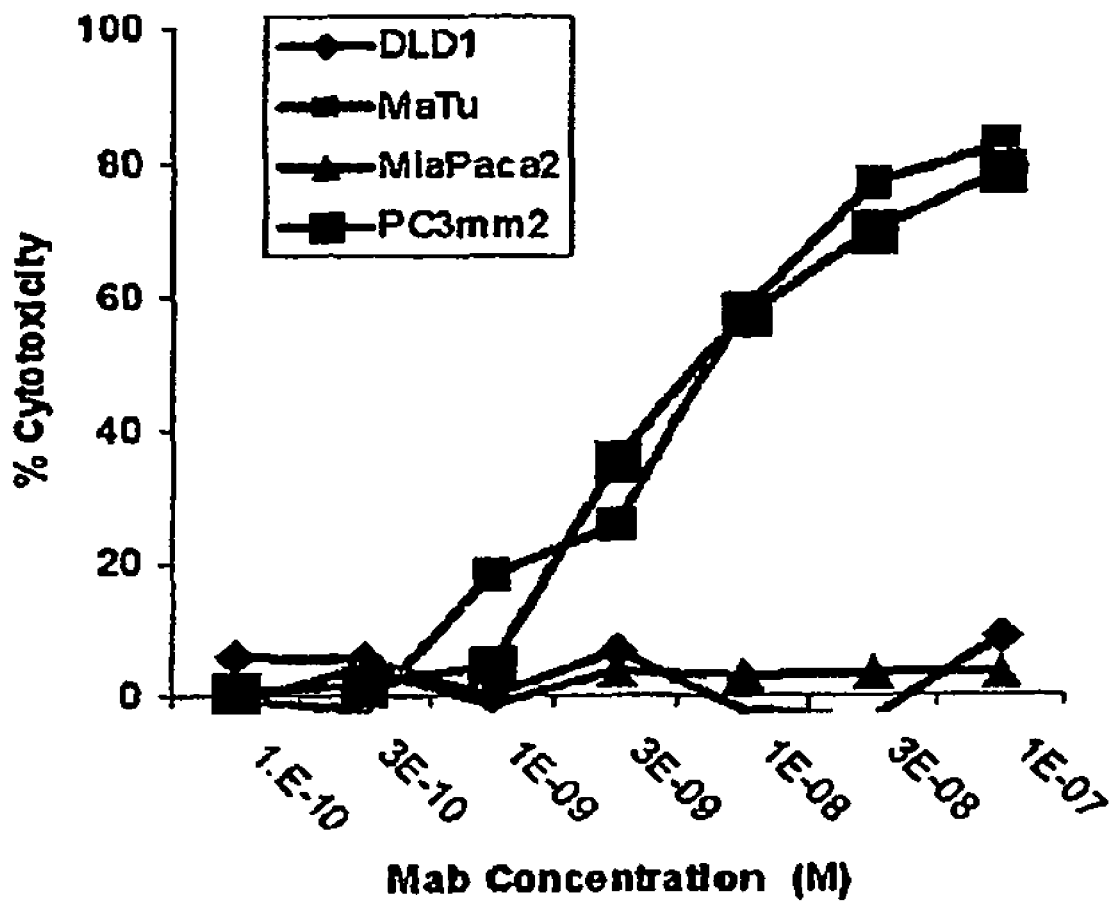
FIG. 13b graphically depicts the cytotoxicity of the 1E4 immunoconjugate against MN+, but against MN−, cells.
Figure 13C:
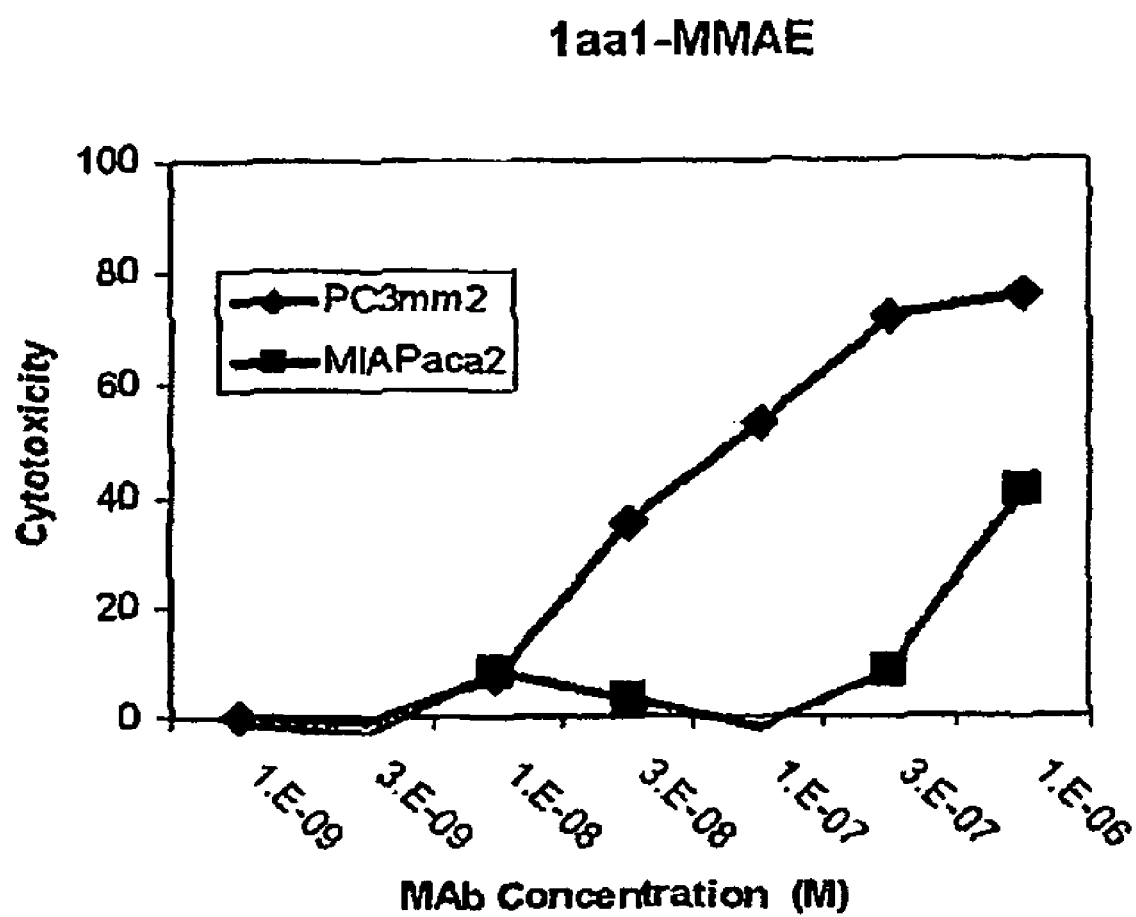
FIG. 13c graphically depicts the cytotoxicity of the 1aa1 immunoconjugate against MN+, but against MN−, cells.

In vitro cytotoxicity assays were carried out. 3ee9/MMAE was found to be highly cytotoxic to MN-expressing PC3mm2 cells (EC50=50 nM), but not to MN-negative MIAPaca2 cells (FIG. 13a). Less than 10% killing of MN-negative cells was seen even at doses as high as 1 uM. The 1A4 immunoconjugate was also found to be selectively cytotoxic for MN+ cells (PC3mm2 and MaTu), but not for MN− cells (MIAPaca2 and DLD1) in the in vitro cytotoxicity assays (FIG. 13b). Additionally, the 1aa1 immunoconjugate was found to be selectively cytotoxic for MN+ cells (PC3mm2), but not for MN− cells (MIAPaca2) in the in vitro cytotoxicity assays (FIG. 13c).

The cytotoxic drug MMAE delivered by 3ee9/MMAE is a tubulin inhibitor that prevents spindle formation during cell mitosis resulting in G2/M arrest. The effect of treatment of MN-expressing cells (Pc3 mm2) and MN non-expressing cells (H460) with 3ee9/MMAE is shown in FIG. 14. The tubulin is stained with florescence labeled antibody. Untreated cells showed normal spindle formation, while the treated MN expressing cells showed fragmented fibers resulting from tubulin binding with MMAE and prevention of normal spindle formation. No activity was seen in MN non-expressing cells. These studies confirmed that the antibody drug conjugate 3ee9/MMAE kills cell through targeted tubulin disruption.

Example 12

In Vivo Activity of Immunoconjugate

In vivo Pharmacology of 3ee9/MMAE Against Subcutaneously Implanted Human Xenograft Cancer Models 3ee9/MMAE exhibits significant and consistent anti-tumor effects on the growth of multiple human xenograft tumor models in athymic mice when administered via the intravenous route in an intermittent schedule. The in vivo anti-tumor effect of 3ee9/MMAE was examined in 6 different human xenograft tumor models. These models were established through subcutaneous implantation of human tumor cells into female athymic NCr (nu/nu) mice (Taconic, N.Y.). The human tumor xenograft models evaluated included the MaTu human mammary carcinoma model, the HT-29 and Colo-205 human colo-rectal carcinoma (CRC) models, PC3MM2 prostate carcinoma model, the HCT-15 multi-drug resistant (P-gp) CRC model, and the MiaPaCa2 human pancreatic model. PBS was used as a vehicle, and dosing solutions were prepared fresh daily. The dosing volume was 0.1 mL/10 g (10 mL/kg).

The length and width of each tumor were measured using an electronic caliper 2-3 times per week, and tumor weights (mg) were calculated based on the formula of [length (mm)× width (mm)$^2$]/2. All data, including daily observations, obtained throughout the course of the study were documented in Anti-tumor Data Acquisition System (ADAS). The maximum tolerated dose (MTD) is defined as the highest dose that does not produce greater than 20% lethality and/or 20% net body weight loss. Tumor growth inhibition (TGI) was calculated as (1-T/C)×100, where T=final tumor weights from a treated group after the last dose, and C=final tumor weights from the control group after the last dose. In addition, anti-tumor efficacy was measured as the incidence of responses (or responders or regressions) defined as tumors with ≦50% of their initial size. A minimum duration of 7 days is required for a response to be considered durable.

Efficacy of 3ee9/MMAE in MaTu Xenograft Model

Human mammary xenograft, MaTu cells were maintained as adherent cultures in RPMI supplemented with 10% FBS. NCr nude mice (8-12 weeks of age) were inoculated subcutaneously in the right flank with 5×10$^6$ cells in 0.1 mL of 80% matrigel/20% HBSS. When tumors reached an average size of ±180 mg (7 days), treatment was initiated. BAY 79-4620 (3ee9-IC) was administered i.v. once every four days (Q4Dx3) at a dose of 1, 3 and 10 mg/kg. Control mice were treated with PBS or an un-conjugated monoclonal antibody at a dose of 10 mg/kg.

Daily examinations into the health status of each animal were conducted. Each experimental group consisted of 10 mice, and the dosing volume was 0.1 mL/10 g body weight. The length and width of each tumor was measured by using an electronic caliper 2-3 times per week, and tumor weights (mg) were calculated based on the formula of [length (mm)× width (mm)$^2$]/2. All data, including daily observations, obtained throughout the course of the study were documented. Tumor growth inhibition (TGI) was calculated as 1-T/C×100, where T=final tumor weights from a treated group, and C=final tumor weights from the control group.

Figure 15:
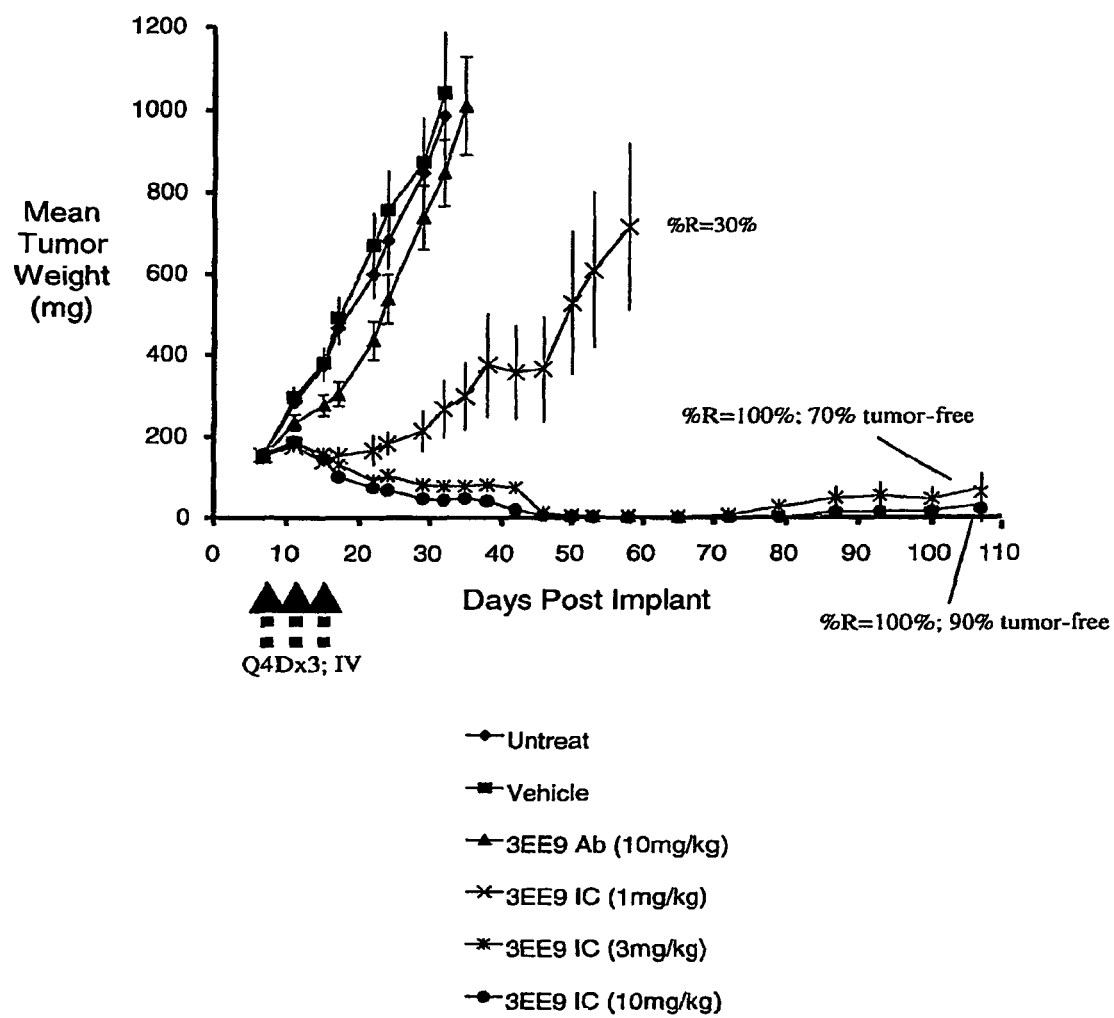
FIG. 15 graphically depicts the anti-tumor efficacy of 3ee9/MMAE against MaTu xenografts.

3ee9/MMAE was well-tolerated at all doses examined with all the treated animals exhibiting no significant weight loss. Representative efficacy of 3ee9/MMAE in the MaTu tumor model is illustrated in FIG. 15. Tumors from both the untreated and vehicle-treated control groups grew progressively in all animals. The mean doubling time for animals in control and vehicle groups were 11.2 days. At the end of dosing, 3ee9/MMAE showed robust anti-tumor efficacy at all doses examined. More specifically, BAY 79-4620 (3ee9-IC) yielded 67, 72 and 78% TGI at 1, 3 and 10 mg/kg, respectively. In comparison, the unconjugated 3ee9 mAb had no significant effect in inhibiting the growth of this mammary xenograft-tumor.

Following the completion of the pre-determined dosing regimen (Q4Dx3), the effect of 3ee9/MMAE on tumor growth delay and regression was determined. As shown in FIG. 15, treatment of 3ee9/MMAE resulted in significant tumor growth delay and regression. At the lowest dose examined (1 mg/kg), following cessation of treatment, tumors remained stable for ~2 weeks and began to grow back thereafter. Overall, 30% of the tumors were responsive to this treatment of 1 mg/kg. In comparison, 100% of the animals responded when challenged with 3 and 10 mg/kg. Of note, even after ~3 months following the cessation of treatment, only 3 and 1 tumors showed signs of re-growth in the 3 and 10 mg/kg groups, respectively, showing that 70 and 90% of the animals remained tumor-free even after ~90 days after the cessation of treatment.

Figure 16:
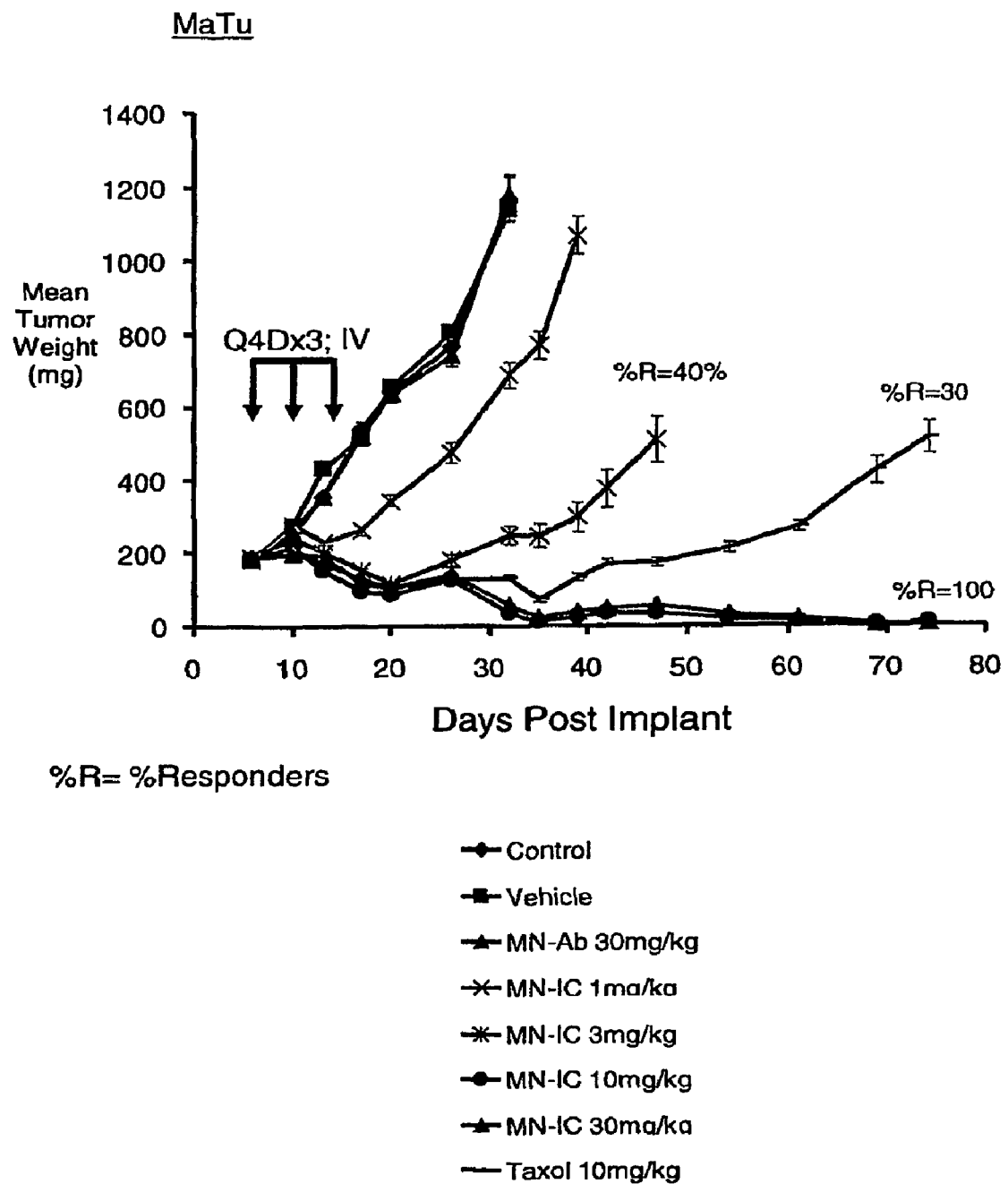
FIG. 16 graphically depicts the anti-tumor efficacy of the 1E4 immunoconjugate against established MaTu breast tumors.
Figure 17:
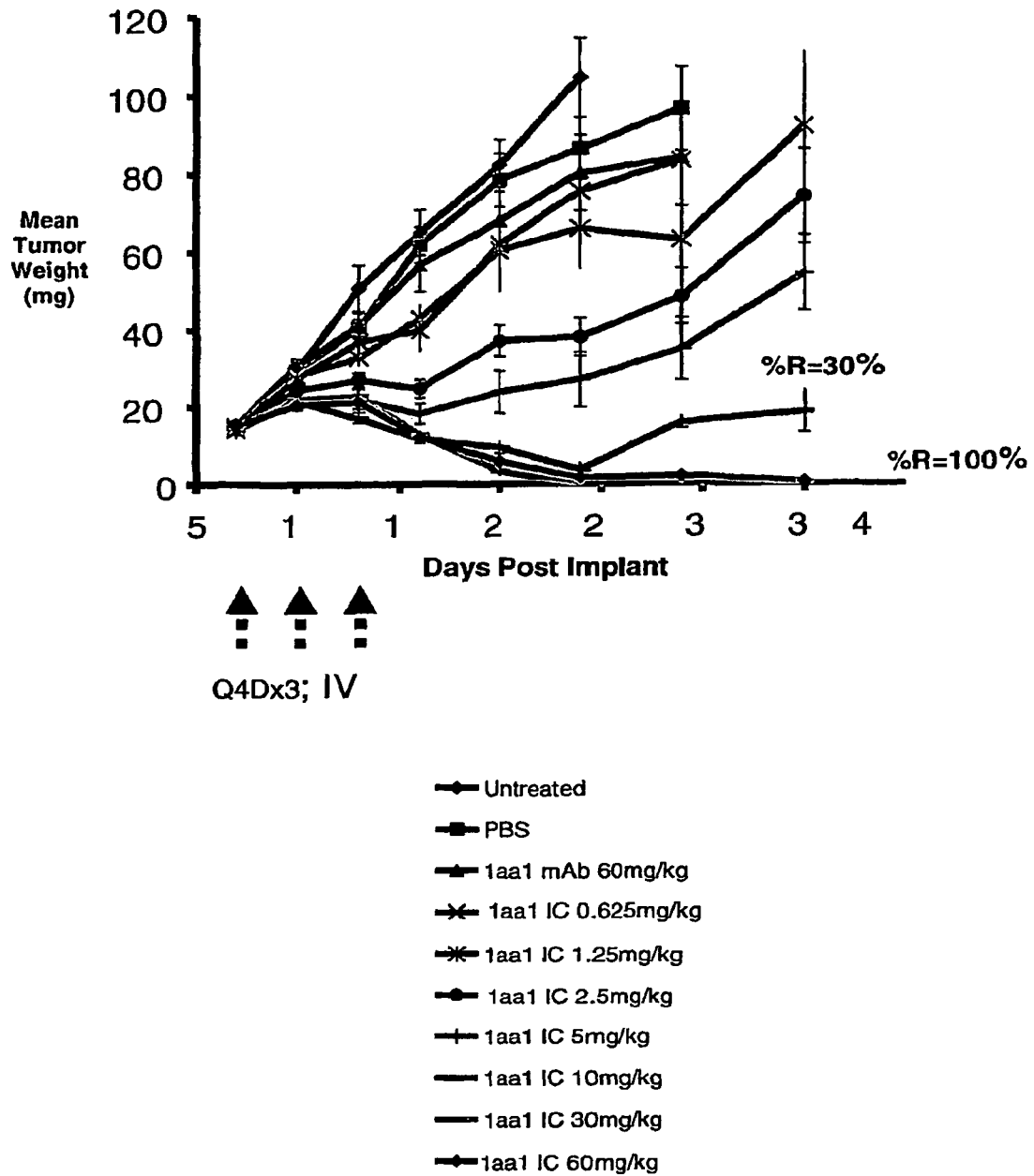
FIG. 17 graphically depicts the anti-tumor efficacy of the 1aa1 immunoconjugate against MaTu xenografts.

The monoclonal IgG1 1E4, when conjugated to a cytotoxic drug, produced a significant anti-tumor effect against the human mammary xenograft, MaTu, when dosed at 30 mg/kg immunoconjugate, whereas the unconjugated antibody had no effect (FIG. 16). Further experiments using the same protocol, but substituting conjugated forms of antibody 1aa1 (FIG. 17), 3ee9 and 5aa3, gave similar results. Additionally, when using the conjugated form of 3ee9, anti-tumor effects were seen in other human xenograft models derived from various histological type including, HT-29 and Colo-205 human colo-rectal cancer xenograft models, and PC3-mm2, a human prostate xenograft model. These data indicate that the therapeutic utility of antibodies directed against MN protein as vehicles for cytotoxic drug delivery to tumors.

Example 13

Therapeutic Index Determination of 3ee9/MMAE in MaTu Xenograft Model

The maximum tolerated dose (MTD), minimum efficacious dose (MED), and therapeutic index (TI) of 3ee9/MMAE was determined using MaTu xenograft tumor-bearing mice. The TI is defined as the ratio of the MTD divided by MED. 3ee9/MMAE was administered intravenously once every 4$^{th}$ day for a total of 3 injections (Q4Dx3). 3ee9/MMAE was administered at dose levels of 0.625, 1.25, 2.5, 5.0, 10, 30 and 60 mg/kg. Control mice were treated with PBS or an unconjugated monoclonal antibody at a dose of 60 mg/kg. 3ee9/MMAE dosed at 60 mg/kg appeared to be the MTD, as there was 10% lethality and ~20% body weight loss in response to this treatment. All other treatment groups were well tolerated.

Figure 18:
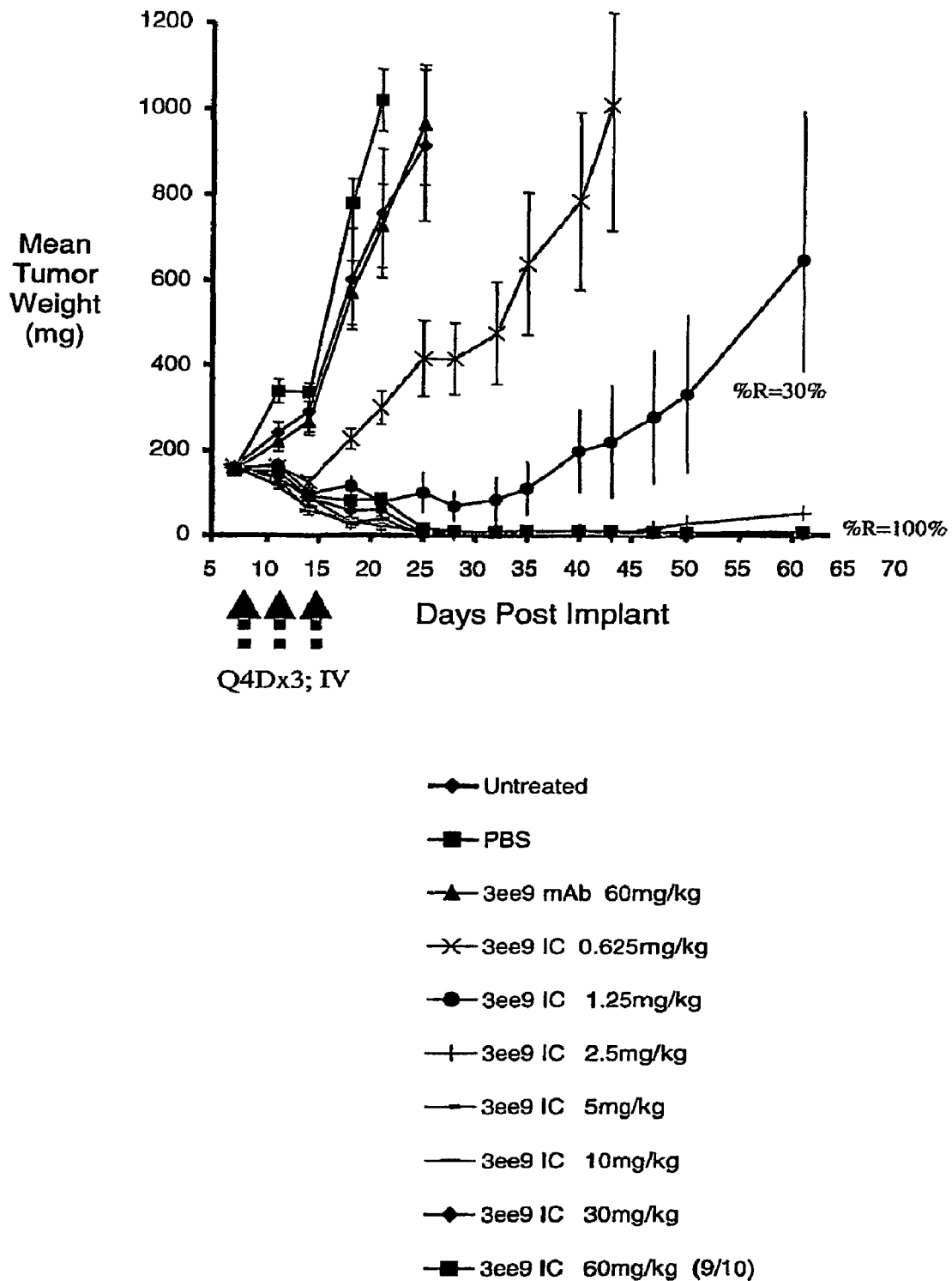
FIG. 18 graphically depicts the therapeutic index (TI) of 3ee9/MMAE against MaTu xenografts.

The anti-tumor activity of 3ee9/MMAE is presented in FIG. 18. At the end of dosing, 3ee9/MMAE at a dose of 0.625 and 1.25 mg/kg resulted in 62 and 81% inhibition, respectively. Doses of 2.5, 5, 10, 30 and 60 mg/kg resulted in a greater inhibition of tumor growth (~90%) with majority of tumors starting to show regressions. Based on data observed, the MED of 3ee9/MMAE was 0.625 mg/kg. Following the completion of the pre-determined dosing regimen (Q4Dx3), the effect of 3ee9/MMAE on tumor growth delay and regression was determined. No tumor regression was seen for the 0.625 mg/kg dose. In contrast, 80% of the animals exhibited tumor regressions in response to 1.25 mg/kg. Moreover, at doses of 2.5 mg/kg and higher, 100% of the animals responded to treatment. The therapeutic index of 3ee9/MMAE was determined to be ~96.

Example 14

Efficacy of 3ee9/MMAE in HT-29 Xenograft Model

Human CRC xenograft, HT-29 cells were inoculated subcutaneously in the right flank with 5×10$^6$ cells in 0.1 mL of HBSS. When tumors reached an average size of ~120 mg (5 days), treatment was initiated. 3ee9/MMAE was administered i.v. once every four days (Q4Dx3) at a dose of 0.625, 1.25, 2.5, 5.0, 10 mg/kg. Control mice were treated with PBS or an un-conjugated monoclonal antibody at a dose of 10 mg/kg. In addition, MMAE was assessed as a free drug at a dose of 0.1, 0.2 and 1 mg/kg. The 0.1 and 0.2 mg/Kg doses of MMAE represent equivalent amounts of this drug to those present on 5 and 10 mg/Kg 3ee9/MMAE respectively.

3ee9/MMAE was well tolerated at all doses examined with all treated animals exhibiting no significant weight loss. Similarly, lower doses of MMAE, i.e., 0.1 and 0.2 mg/kg, were also well tolerated with non-significant, minimal weight loss. However, at the top dose of 1 mg/kg, 50% lethality was observed with the remaining animals exhibiting severe weight loss and thus was considered toxic.

Figure 19:
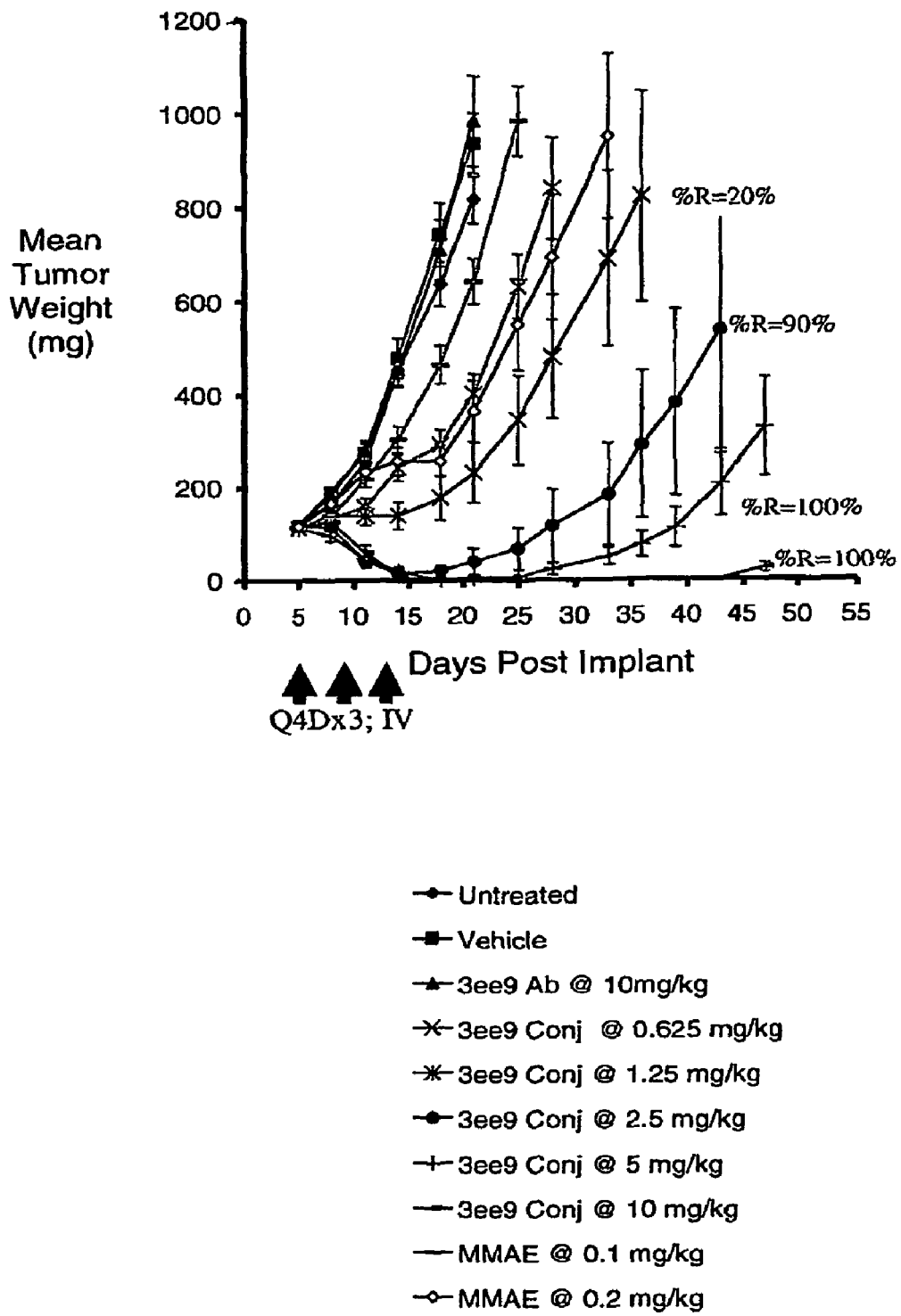
FIG. 19 graphically depicts the anti-tumor efficacy of 3ee9/MMAE and free MMAE against HT-29 xenografts.

Representative efficacy of 3ee9/MMAE and free MMAE in the HT-29 tumor model is illustrated in FIG. 19. Tumors from both the untreated and vehicle-treated control groups grew progressively in all animals. The mean doubling time for animals in control and vehicle groups were 6.4 days. At the end of dosing, 3ee9/MMAE showed robust anti-tumor efficacy at all doses examined. More specifically, 3ee9/MMAE at doses of 0.625, 1.25, 2.5, 5 and 10 mg/kg yielded 54, 72, 97, 100 and 100% TGI, respectively. In comparison, free MMAE of 0.2 mg/kg resulted in significant TGI of 60%, whereas 0.1 mg/kg had no significant effect in inhibiting the growth of this xenograft model. In terms of tumor responses, 3ee9/MMAE dosed at 1.25 mg/kg resulted in 20% of the animals showing regressions. At higher doses, the tumor responses were much greater, with 2.5 mg/kg showing 90% regressions and 5 and 10 mg/kg inducing 100% responses. In contrast, free MMAE did not induce any tumor responses as defined above.

Figure 20:
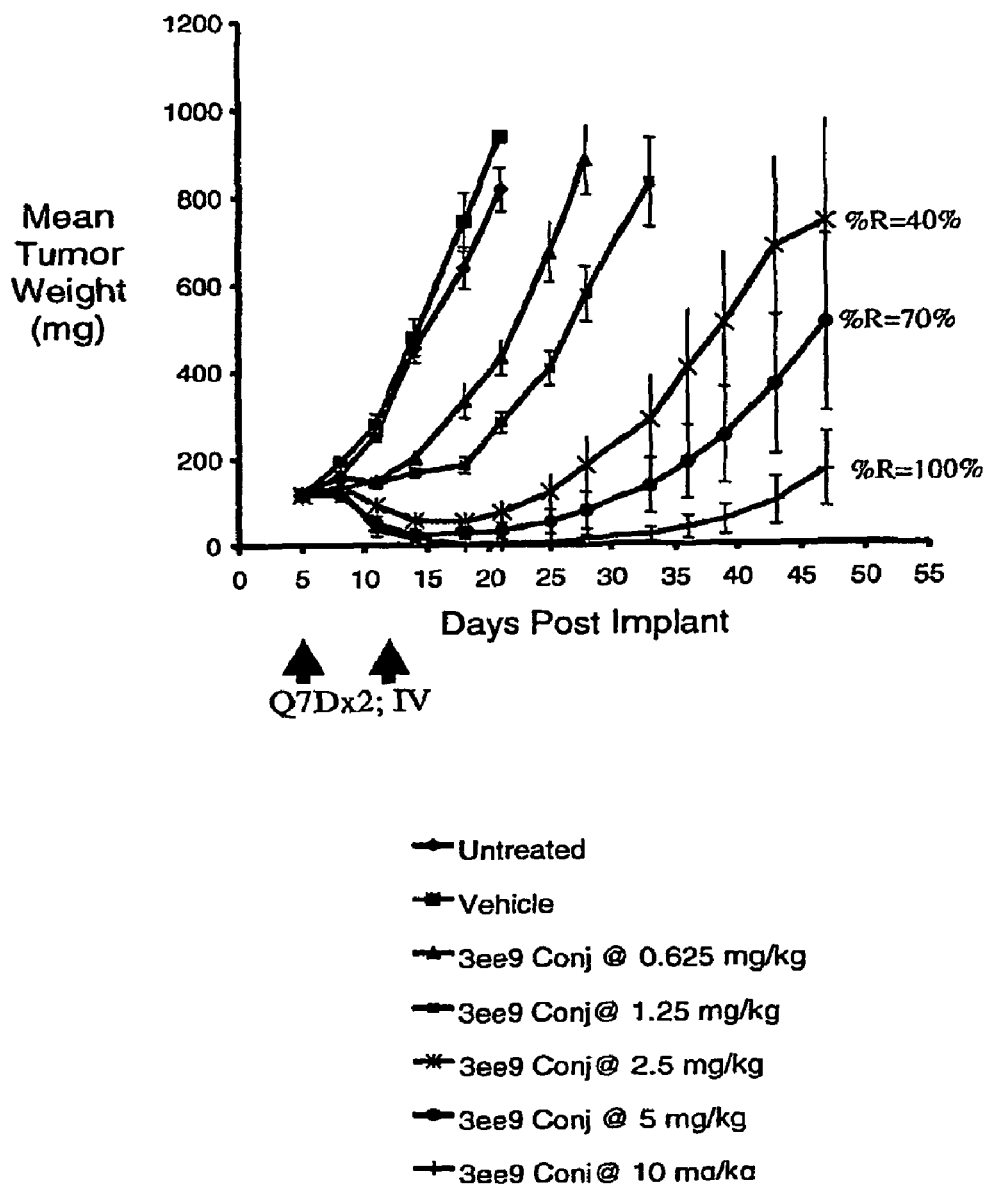
FIG. 20 graphically depicts the anti-tumor efficacy of 3ee9/MMAE against HT-29 xenografts, following the Q7Dx2 schedule.
Figure 21:
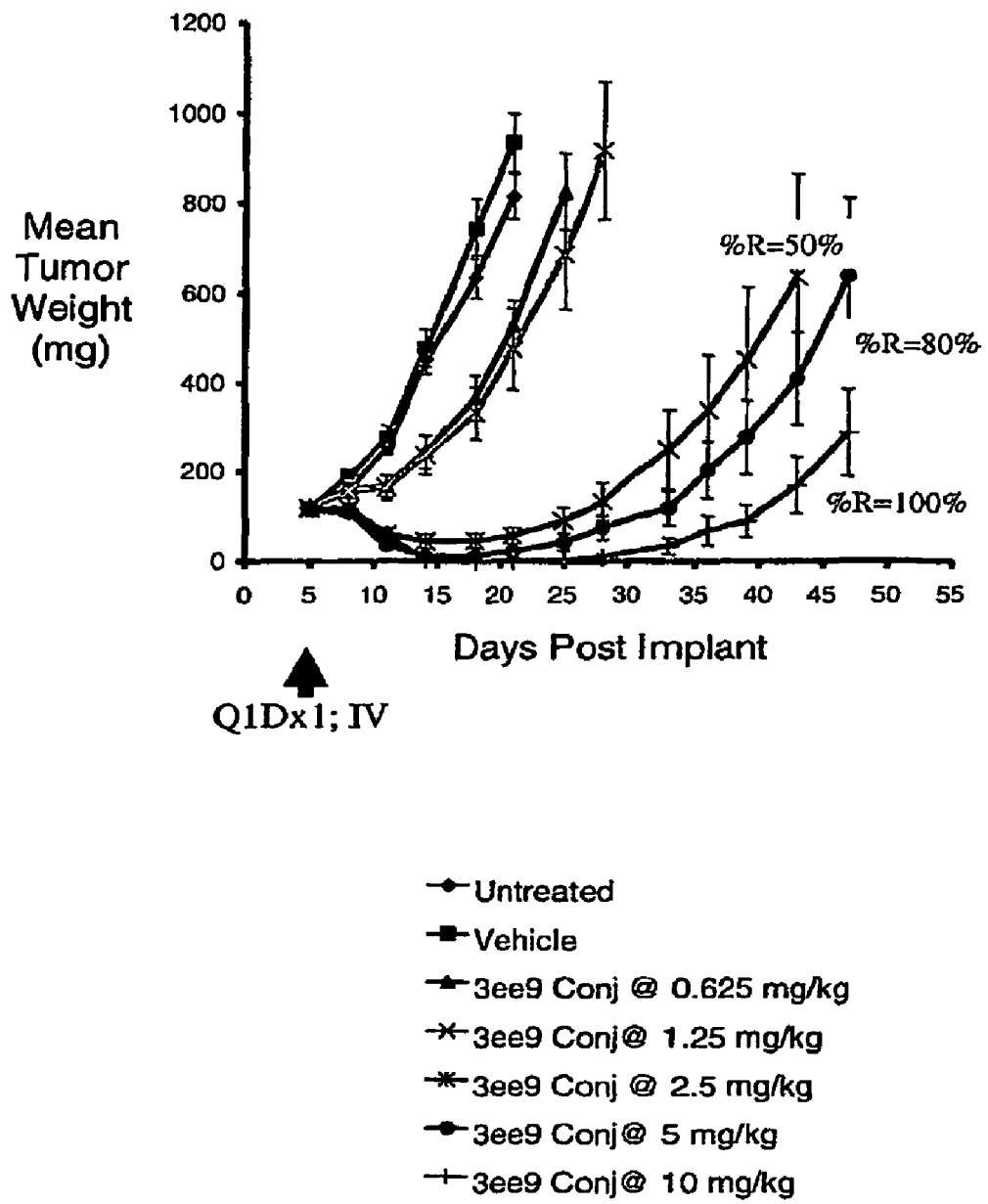
FIG. 21 graphically depicts the anti-tumor efficacy of 3ee9/MMAE against HT-29 xenografts, following the Q1Dx1 schedule.

Anti-tumor effect of 3ee9/MMAE was also assessed in varying schedules, i.e., once a week dosing for total of two doses (Q7Dx2, FIG. 20) and a single dose at the time of staging (Q1Dx1, FIG. 21). In both schedules, 3ee9/MMAE was dosed at 0.625, 1.25, 2.5, 5 and 10 mg/kg. Regardless of schedule, 3ee9/MMAE was highly effective in inhibiting the growth in this CRC xenograft model.

Table 2, below, summarizes anti-tumor efficacy of 3ee9/MMAE. The anti-tumor efficacy was very similar to that which was observed for 3ee9/MMAE in the Q4Dx3 schedule, indicating that in the schedules examined, the anti-tumor efficacy of 3ee9/MMAE appears to be schedule-independent.

TABLE 2

Anti-tumor efficacy of 3ee9/MMAE

| Compound | Dose (mg/kg) | Treatment Schedule | % Inhibition (1 − T/D) * 100 (Day 18) | Percent Regressions |
|---|---|---|---|---|
| Control | N/A | N/A | N/A | 0 |
| PBS | 0 | Q4D x 3 | −17 | 0 |
| 3ee9 Ab | 10 | Q4D x 3 | −11 | 0 |
| 3EE9IC | 0.625 | Q4D x 3 | 54 | 0 |
| 3EE9IC | 1.25 | Q4D x 3 | 72 | 2 |
| 3EE9IC | 2.5 | Q4D x 3 | 97 | 9 |
| 3EE9IC | 5 | Q4D x 3 | 100 | 10 |
| 3EE9IC | 10 | Q4D x 3 | 100 | 10 |
| 3EE9IC | 0.625 | Q7D x 2 | 48 | 0 |
| 3EE9IC | 1.25 | Q7D x 2 | 71 | 0 |
| 3EE9IC | 2.5 | Q7D x 2 | 92 | 4 |
| 3EE9IC | 5 | Q7D x 2 | 96 | 7 |
| 3EE9IC | 10 | Q7D x 2 | 100 | 10 |
| 3EE9IC | 0.625 | Q1D x 1 | 42 | 0 |
| 3EE9IC | 1.25 | Q1D x 1 | 48 | 0 |
| 3EE9IC | 2.5 | Q1D x 1 | 93 | 5 |
| 3EE9IC | 5 | Q1D x 1 | 98 | 8 |
| 3EE9IC | 10 | Q1D x 1 | 100 | 10 |
| MMAE | 1 | Q4D x 3 | Toxic | N/A |
| MMAE | 0.1 | Q4D x 3 | 27 | 0 |
| MMAE | 0.2 | Q4D x 3 | 60 | 0 |

Example 15

Efficacy of 3ee9/MMAE in PC3mm2 and Colo-205 Xenograft Models

The anti-tumor activity of 3ee9/MMAE was next evaluated against human prostate (PC-3 mm2) and CRC (Colo-205) tumor xenografts. Female NCr nu/nu mice were implanted subcutaneously (s.c.) either with $5\times10^6$ PC3mm2 or Colo-205 cells. Treatment was initiated when tumors were of an average size of approximately 125-150 mg. The general health of mice was monitored and recorded daily. Tumor dimensions and body weights were recorded twice a week starting with the first day of treatment.

Figure 22:
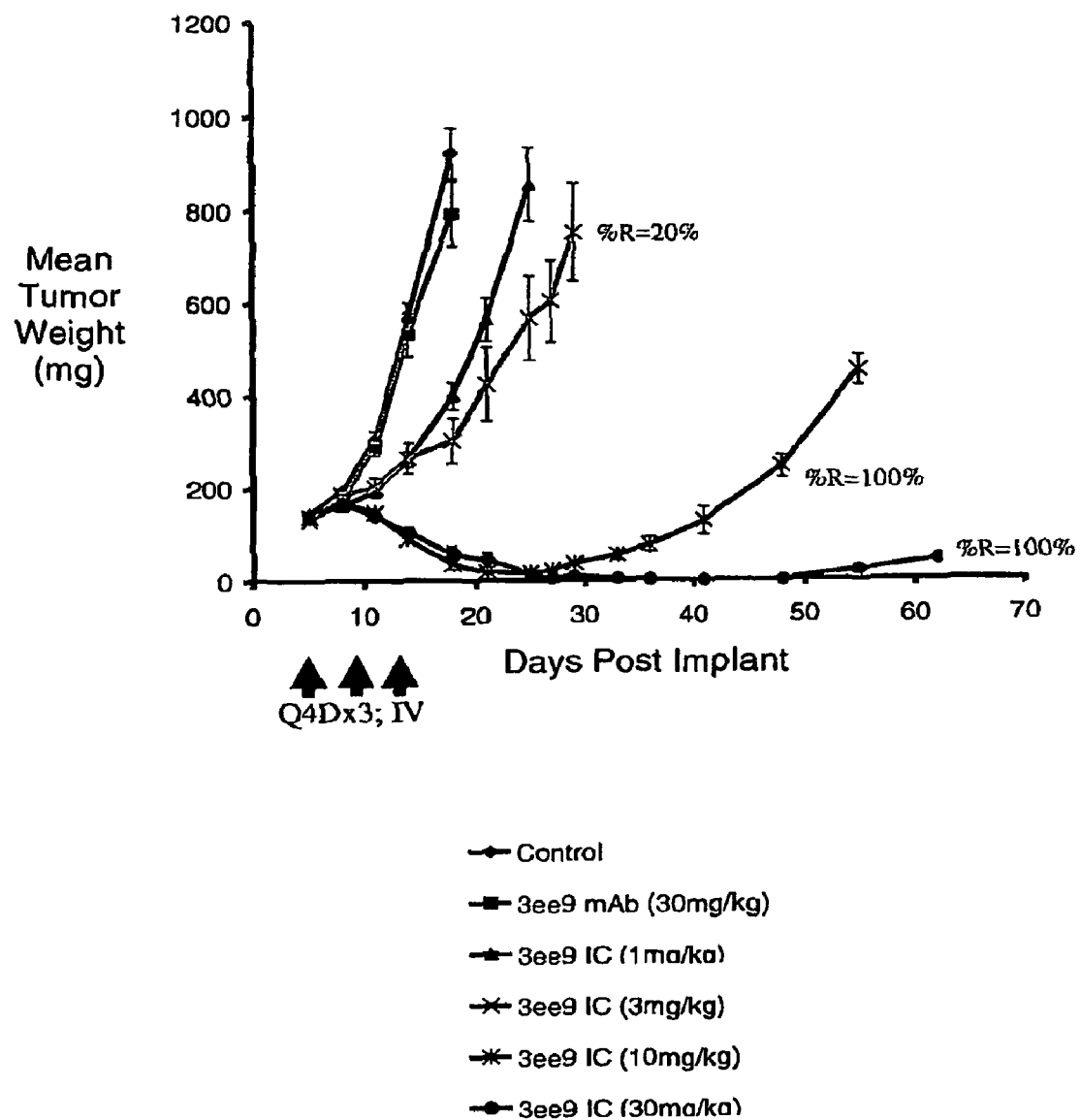
FIG. 22 graphically depicts the anti-tumor efficacy of 3ee9/MMAE against PC3mm2 xenografts.

In the PC3mm2 and Colo-205 studies, 3ee9/MMAE was administered intravenously (i.v.) once every 4th day for a total of 3 injections (Q4Dx3) at doses of 1, 3, 10 and 30 mg/kg and 1.25, 2.5, 5 and 10 mg/kg, respectively. As in other studies, 3ee9/MMAE was well tolerated at all doses evaluated. 3ee9/MMAE inhibited the growth of established PC3MM2 prostate tumors when administered at dose levels of 10 and 30 mg/kg, with 100% of the animals showing responses (FIG. 22). At the lower doses of 1 and 3 mg/kg, only moderate effects were seen, as 45 to 50% TGI was observed at the end of dosing. 20% of the animals did, however, show responses in the 3 mg/kg group.

Figure 23:
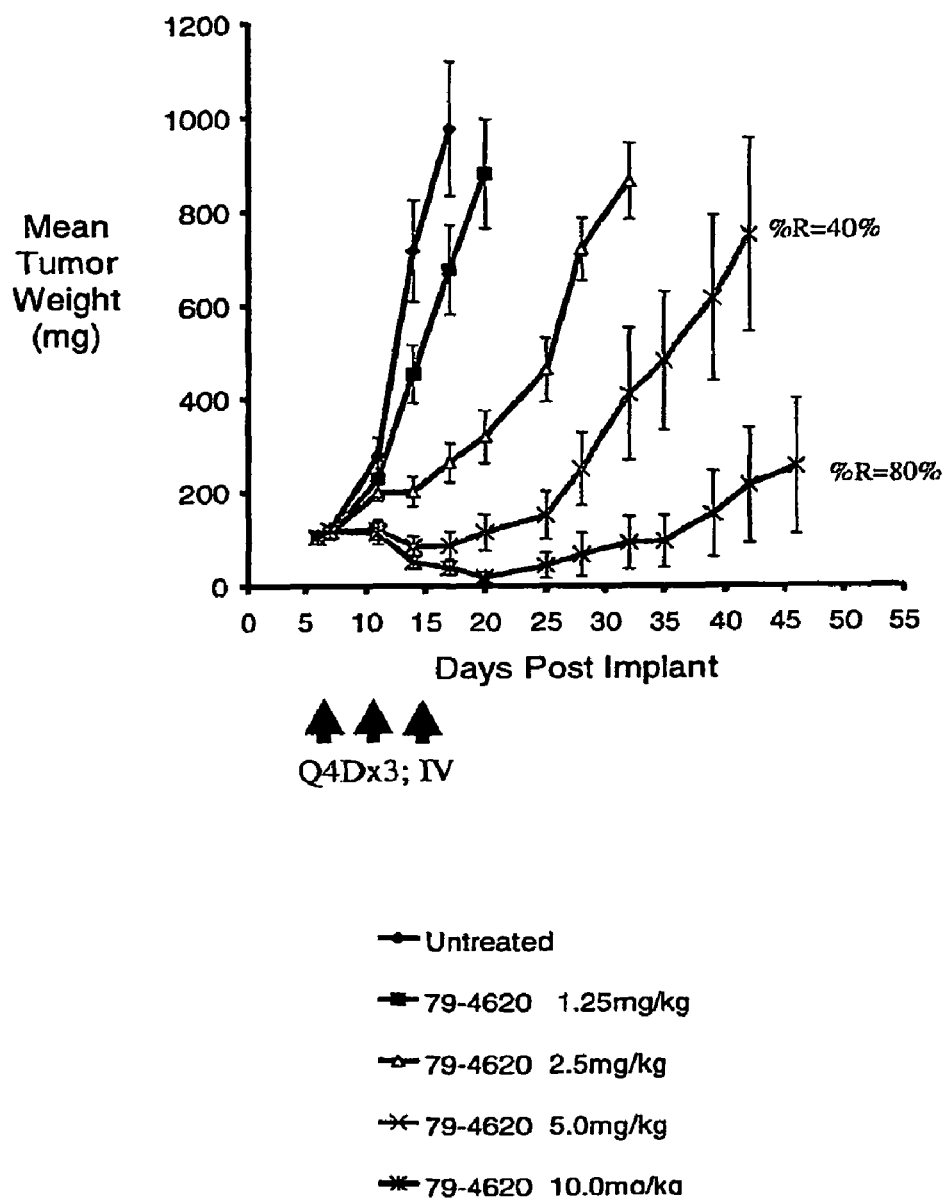
FIG. 23 graphically depicts the anti-tumor efficacy of 3ee9/MMAE against Colo-205 xenografts.

Similarly in the Colo-205 CRC xenograft model, 3ee9/MMAE was highly effective in inhibiting tumor growth (FIG. 23). At the end of dosing, >90% TGI was observed for 5 and 10 mg/kg doses and >70% TGI was seen in response to 2.5 mg/kg dose. The lowest dose, 1 mg/kg, of 3ee9/MMAE was relatively ineffective against this CRC model. In terms of regressions, 3ee9/MMAE dosed at 5 and 10 mg/kg resulted in, 40 and 80% responses, respectively.

Example 16

Efficacy of 3ee9/MMAE in HCT-15 Xenograft Model

Figure 24:
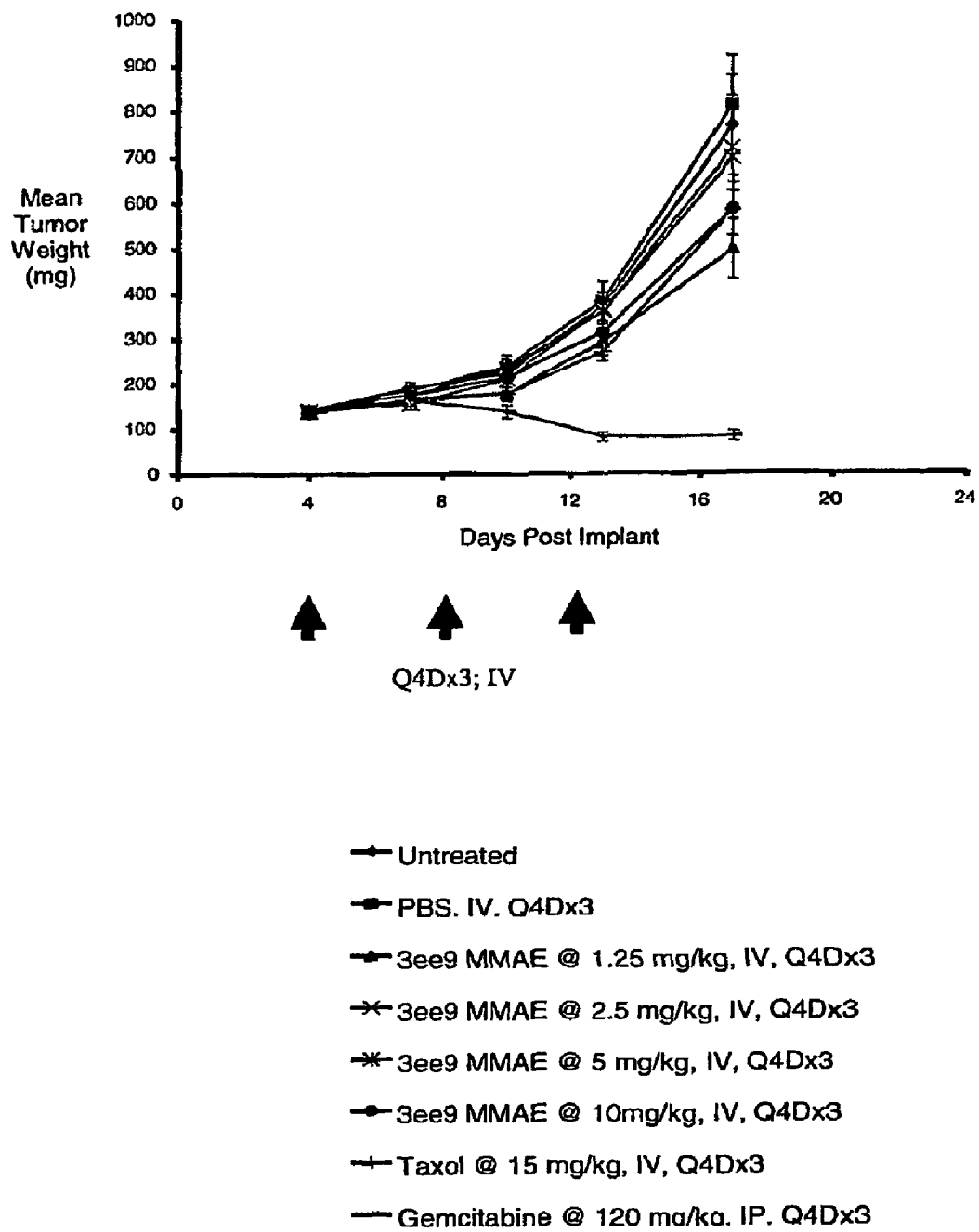
FIG. 24 graphically depicts the anti-tumor efficacy of 3ee9/MMAE against HCT-15 xenografts.

To examine the effect of 3ee9/MMAE in a multi-drug resistance model, female NCr nu/nu mice were implanted subcutaneously (s.c.) with $5\times10^6$ HCT-15 cells. HCT-15 is a multi-drug resistant (MDR) line that over-expresses P-glycoprotein (P-gp). As such, this cell line exhibits a multi-drug resistance phenotype and is resistant to Taxol®, doxorubicin and etoposide. 3ee9/MMAE, Taxol, and Gemcitabine were administered when mice had established tumors with mean weight of ~150 mg. Gemcitabine, a pyrimidine analog that is not a P-gp substrate was used as a positive control. As expected, Gemcitabine (120 mg/kg, i.p., QDx10) was highly active in this MDR model (FIG. 24). In contrast, 3ee9/MMAE (MMAE being a known substrate of P-gp) and Taxol® failed to produce any significant anti-tumor effect.

Example 17

Efficacy of 3ee9/MMAE in huMN-MIAPaca2 and MIAPaca2 Xenograft Models

Figure 25:
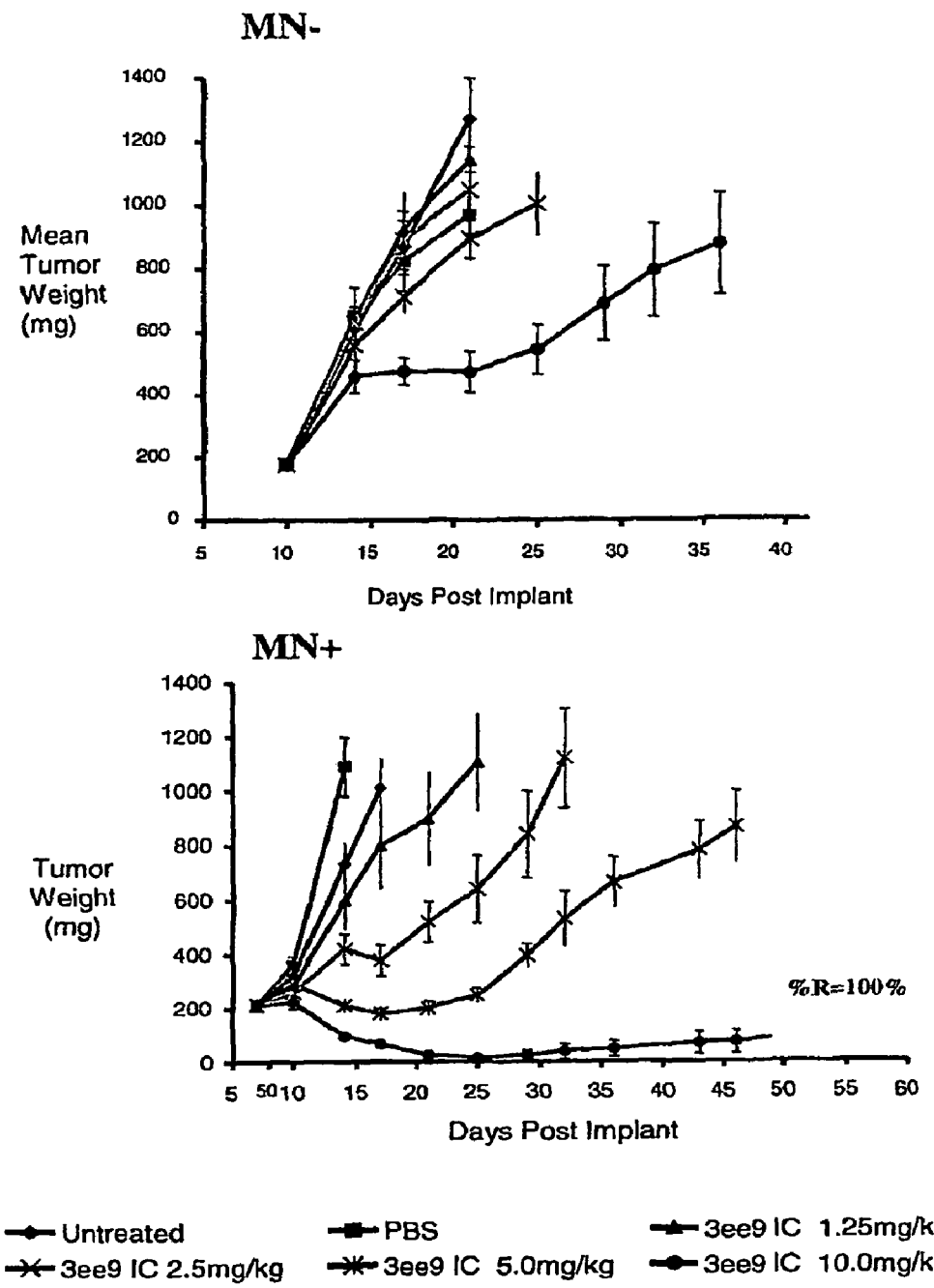
FIG. 25 graphically depicts the anti-tumor efficacy of 3ee9/MMAE against MN− (in left-hand graph) and MN+ (in right-hand graph) MIAPaca2 xenografts.

To better understand the relationship between MN expression and antitumor efficacy, xenograft efficacy studies were conducted using a low MN-expressing pancreatic model, MIAPaCa2 and high MN-expressing huMN-MIAPaCa2 model. This latter line was derived by engineering the MIAPaCa2 line to stably express MN. 3ee9/MMAE had minimal effect in inhibiting the growth of this low MN-expressing MIAPaCa2 line (FIG. 25). 3ee9/MMAE dosed at 10 mg/kg only produced 50% TGI. In contrast, significant anti-tumor activity was seen for 3ee9/MMAE against huMN-MIAPaCa2 model, where, at the end of dosing, doses of 2.5, 5 and 10 mg/kg yielded TGI of 63, 82 and 94%, respectively. Moreover, the 10 mg/kg dose induced 100% responses, indicating that there is a great shift in sensitivity by over-expressing MN levels in tumors.

Example 18

Combination with Xeloda® in Colo-205 Xenograft Model

Figure 26A:
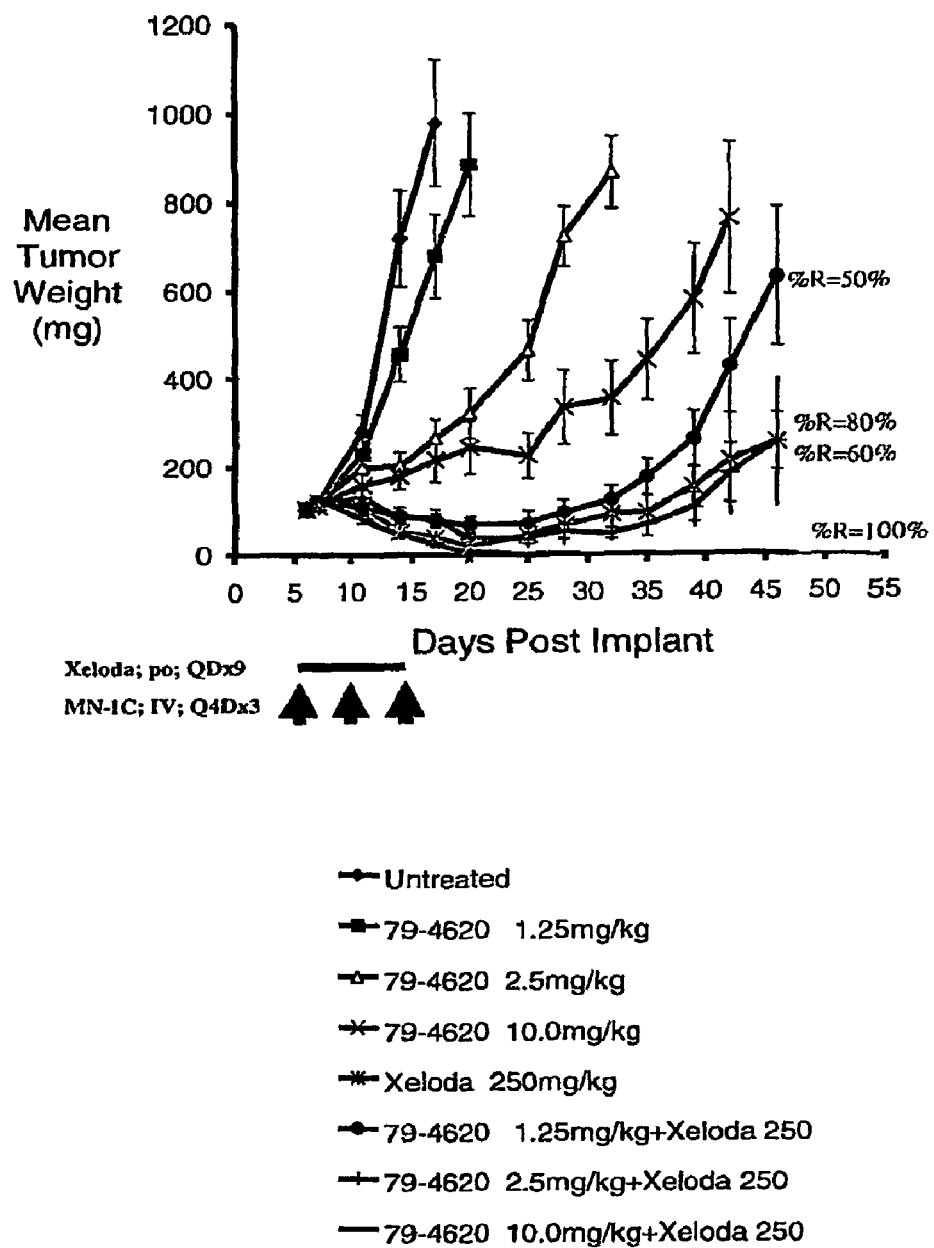
FIGS. 26a and 26b graphically depict the anti-tumor efficacy of 3ee9/MMAE in combination with Xeloda® against Colo-205 CRC xenografts at varying doses.

The feasibility of using 3ee9/MMAE in conjunction with other cancer chemotherapeutic agents was investigated. Xeloda® is used as first line treatment of patients with metastatic colorectal carcinoma. The activity and tolerability of combined therapy using 3ee9/MMAE and Xeloda® was evaluated. 3ee9/MMAE was administered i.v. on a Q4Dx3 schedule and at dose levels of 1.25, 2.5 and 10 mg/kg. Xeloda® was administered orally once daily for 9 days at dose levels of 250 and 500 mg/kg. 3ee9/MMAE administered alone at 2.5 and 10 mg/kg resulted in robust tumor growth inhibition (TGI of 73 and 96%, respectively) (FIG. 26a). The 1.25 mg/kg group of 3ee9/MMAE, however, was relatively ineffective, resulting in only 31% TGI. Xeloda® administered alone at dose levels of 250 and 500 mg/kg also produced robust TGI of 78 and 86%, respectively.

Figure 26B:
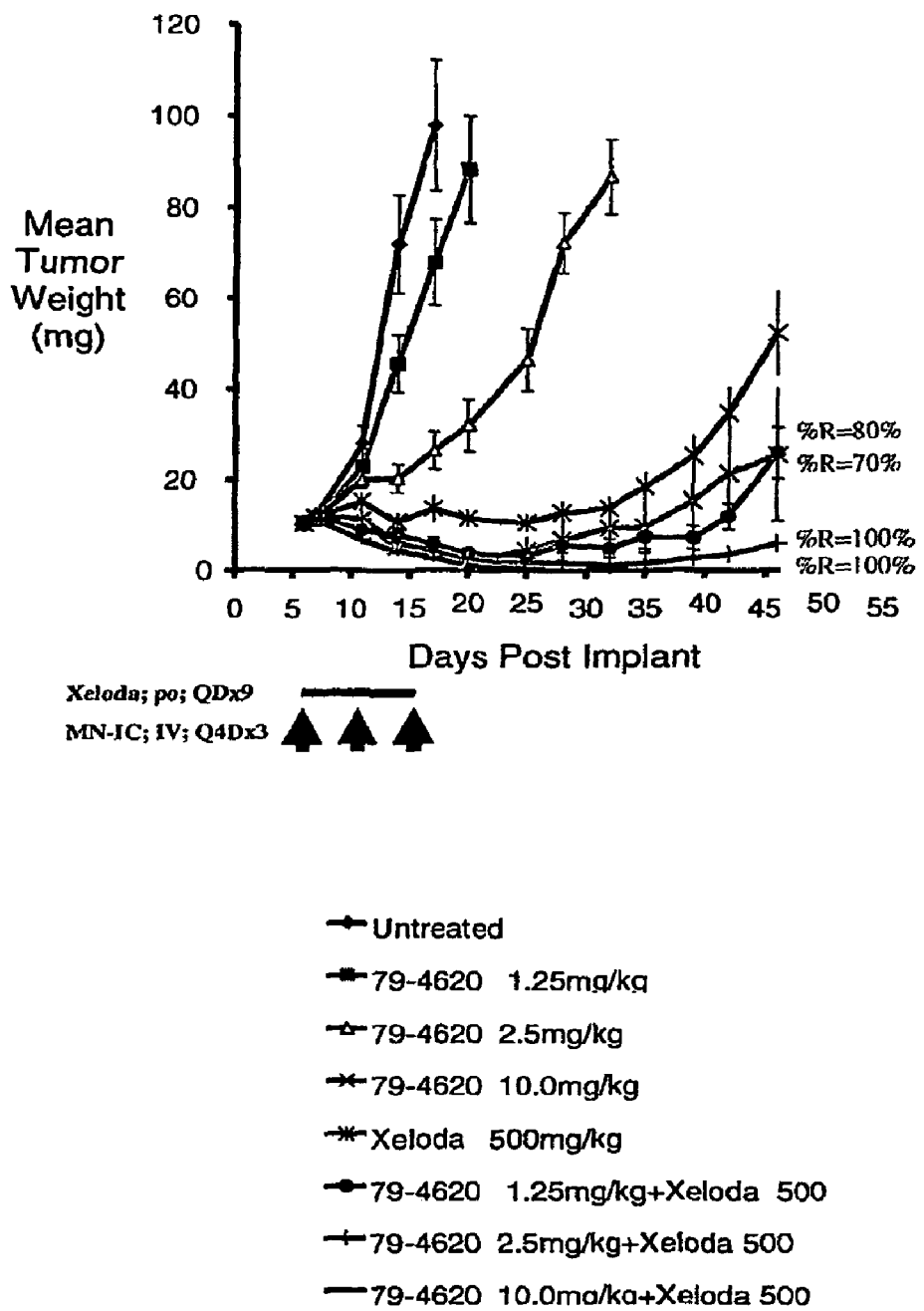

In terms of responses, 10 mg/kg group of 3ee9/MMAE induced 80% response rate, whereas zero percent of the animals in both dose groups of Xeloda showed any regressions. All combination treatment groups were well tolerated and resulted in significant inhibition of tumor growth as well response rates. Quantitative data detailing the TGI and tumor responses by combining these two agents are shown in FIGS. 26a and 26b, as well as Table 3, below. In the doses examined, the anti-tumor activity of 3ee9/MMAE in combination with Xeloda® was far superior to that of either 3ee9/MMAE or Xeloda® administered as single agents. Finally, in regards to tolerability, administration of these therapeutics was well tolerated with no adverse reactions.

mg/kg ketamine/10 mg/kg xylazine, i.p.), and placed inside the imaging system. Multi-spectral image cubes (series of images) were acquired with images spaced every 10 nm throughout the spectral range of 680 to 950 nm, which covered the Near Infrared (NIR) range.

Each image was exposed for 5 seconds. False-colored images were synthesized from the spectral cube using Maestro software and scaled to visible brightness using ImagePro Plus 6.0. Scaling was identical to all images, with the brightest image slightly below saturation level. Most fluorescently labeled antibodies tend to localize to the liver and the bladder.

TABLE 3

Anti-tumor activity of BAY 79-4620 (3ee9-IC) in combination with Xeloda ®

| Treatment | Schedule | Dose mg/kg/inj | % Inhibition (T/C) (d 17) | % Weight Loss (d 17) | % Regressions |
|---|---|---|---|---|---|
| Untreated | — | — | — | 0.3 | 0 |
| 79-4620 (3ee9 cj) | Q4DX3; IV | 1.25 | 30.6 | 0.5 | 0 |
| 79-4620 (3ee9 cj) | Q4DX3; IV | 2.5 | 73 | 0.1 | 0 |
| 79-4620 (3ee9 cj) | Q4DX3; IV | 10 | 96.2 | 0.9 | 80 |
| Xeloda | Q1DX9; PO | 250 | 78 | −0.5 | 0 |
| Xeloda | Q1DX9; PO | 500 | 86.1 | −5.6 | 0 |
| Xeloda (250 mg/kg) | | | | | |
| 79-4620 (3ee9cj) + Xeloda | Q4DX3; IV/Q1DX9; PO | 1.25 | 92.1 | −2 | 50 |
| 79-4620 (3ee9 cj) + Xeloda | Q4DX3; IV/Q1DX9; PO | 2.5 | 91.4 | −0.9 | 60 |
| 79-4620 (3ee9 cj) + Xeloda | Q4DX3; IV/Q1DX9; PO | 10 | 97.5 | −0.4 | 100 |
| Xeloda (500 mg/kg) | | | | | |
| 79-4620 (3ee9 cj) + Xeloda | Q4DX3; IV/Q1DX9; PO | 1.25 | 94.2 | −0.3 | 70 |
| 79-4620 (3ee9 cj) + Xeloda | Q4DX3; IV/Q1DX9; PO | 2.5 | 95.7 | −3.2 | 90 |
| 79-4620 (3ee9 cj) + Xeloda | Q4DX3; IV/Q1DX9; PO | 10 | 97.3 | −1.4 | 100 |

Example 19

In vivo Distribution/Tumor Localization of 3ee9 mAb Against Bilaterally Implanted Human Xenograft Cancer Model To determine the in vivo distribution and tumor localization of the mAb component of 3ee9/MMAE, non-invasive in vivo imaging studies were conducted using the CRI Maestro™ in mice which received bilateral implantation of tumors exhibiting both high and low MN expression. The Maestro™ in-vivo imaging system (CRI, Woburn, Mass.) with multi-spectral acquisition and analysis is designed to eliminate auto-fluorescence background. Mabs 3ee9 of BAY 79-4620, M75 (mouse monoclonal recognizing MN) and control human IgG, were conjugated with Alexa Fluor 750 (Invitrogen Cat# A20011) according to manufacturer's instructions. The ratio of Protein/AF750(mol/mol) was 1/5.9 for 3ee9, 8.9 for human IgG, and 6.0 for M75.

Figure 27:
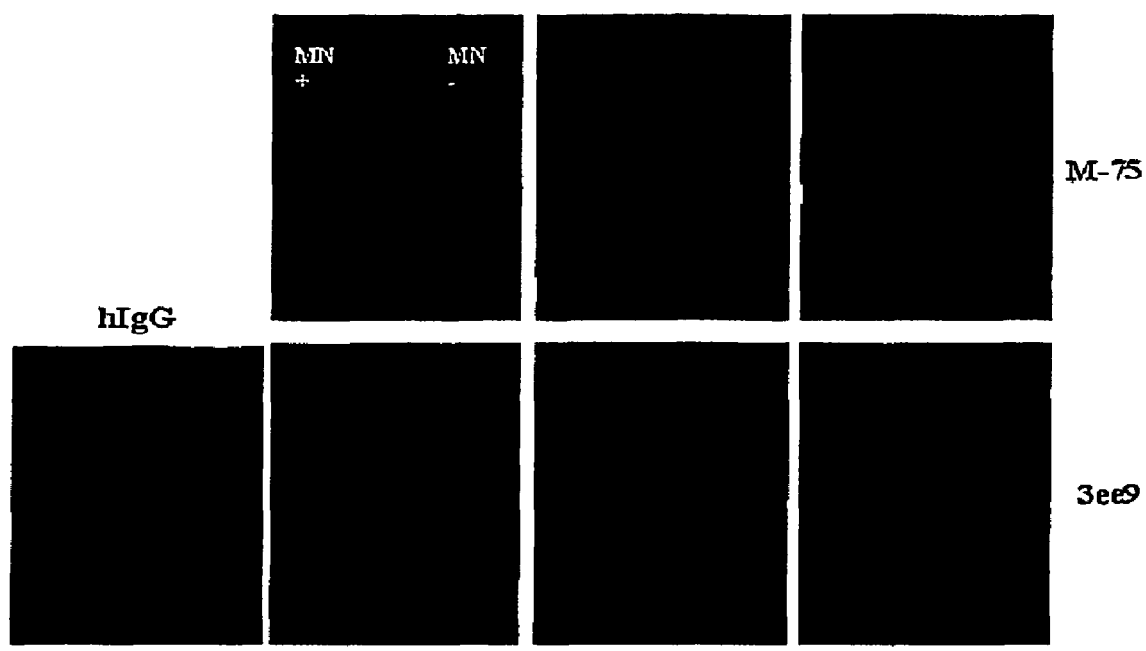
FIG. 27 shows immunofluorescence images depicting in vivo localization of 3ee9 in huMN−MIAPaca2 and MIA-Paca2 tumors.

Twelve days before the injection of each fluorescence-labeled antibody, Harlan Balb/C nudes were implanted with MIAPaCa-2 (low MN-expressing; 7.5×10$^6$ cells in 50% Matrigel) subcutaneously in the right flank, and huMN-MIA-PaCa2 (MN transfected stable cell line; 5×10$^6$ cells in 50% Matrigel) subcutaneously in the left flank. 4 μg of conjugated antibody was injected on Day 0 (12 days post implant) to each animal. Imaging was done on Day 4, Day 5 and Day 10. Data were collected using animals that were anaesthetized (100 After 4 to 5 days, most of signal then decreases from the liver and the bladder and stabilizes in the tumor. Images taken on Day 5 yielded the highest signal to background ratio (FIG. 27.) After five days, there was very little signal generated from the hIgG-injected animals, indicating that hIgG failed to localized into tumor tissue. In contrast, both M75 and 3ee9 localized specifically to high MN-expressing (huMN-MIA-PaCa2) tumors. No localization was seen in low MN-expressing MIAPaCa2 tumors in the same animals.

Example 20

In vivo Mechanism of Action

To explore the in vivo mechanism of action of 3ee9/MMAE, tumors were implanted subcutaneously at right flank of the mice with 5×10$^6$ HT-29 cells. Eight days later, athymic mice bearing HT-29 tumors were treated with vehicle or with 3ee9/MMAE at 1.25 and 5 mg/kg (Q1Dx1). Tumors were collected and fixed in formalin 4 hours and 1, 3 and 5 hours following administration of 3ee9/MMAE. Samples were then embedded in paraffin, sectioned at 5 μm, de-paraffinized, and stained using standard protocol for fluorescent immunohistochemistry of human tissues using mouse antibodies: Anti-α/β-tubulin, Anti-phospho-Histone H3, and DNA. The slides were then observed under a fluorescent microscope, and representative images were taken through three separate color channels.

Figure 28:
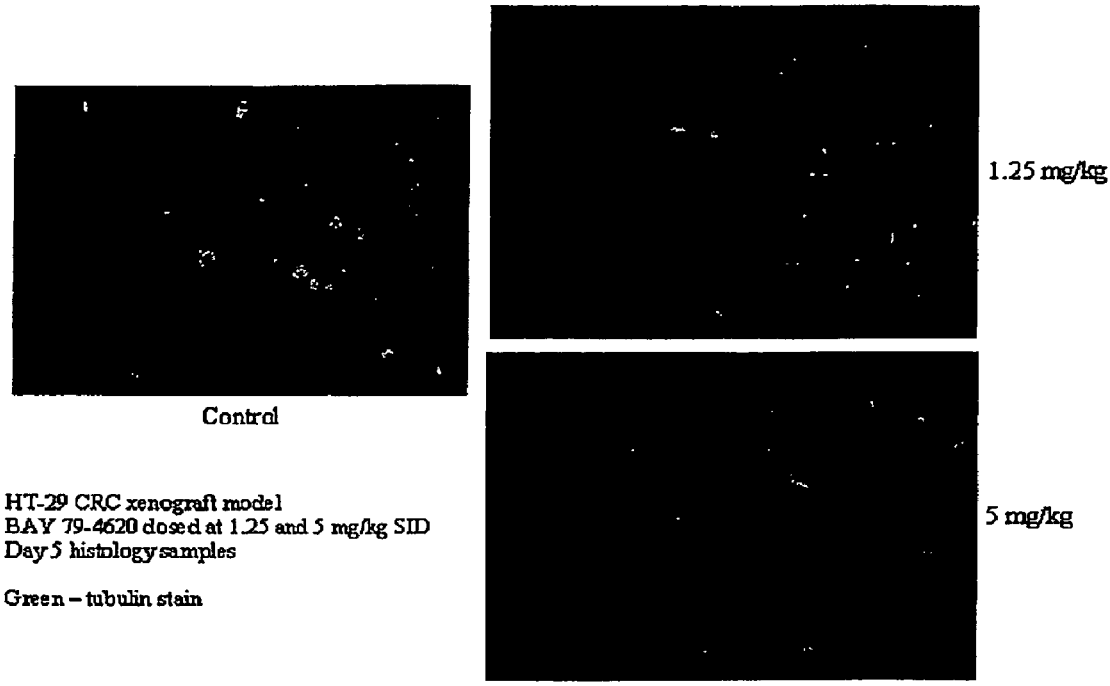
FIG. 28 show immunofluorescence images (of histological samples) depicting 3ee9/MMAE inhibition of tubulin polymerization in HT-29 CRC xenografts at two doses.

3ee9/MMAE had little effect in affecting cell mechanism in the 4 hr samples. However, by day 1, increased numbers of cells were in G2/M arrest, and multi-polar spindle was clearly seen. In addition, decreased level of tubulin staining could be observed. These effects were then highly amplified in the day 3 and day 5 samples. In fact, almost all cells in the 5 mg/kg dose group of 3ee9/MMAE on day 5 were severely affected by treatment (FIG. 28). These data clearly indicate that the 3ee9/MMAE affected the growth of cancer cells by tubulin inhibition, leading to G2/M arrest and apoptosis.

Table 4, below, summarizes the behavior profile of 3ee9/MMAE.

TABLE 4

3ee9/MMAE profile

| Assay | Result for 3ee9/MMAE |
| --- | --- |
| Affinity (Kd) | 3.6 nM |
| Cell binding (FACS): MN+/MN− | +++/− |
| Internalization: MN+/MN− | +++/− |
| Cytotoxicity: MN+/MN− (ec50) | 50 nM/>1 μM |
| Immunoprecipitation | specific |
| IHC | specific |
| In vivo distribution | normal |
| In vivo activity: MED | 1 mg/kg |
| In vivo activity: MTD | 60 mg/kg |

Example 21

Expression Vector Construction, Transfection, Expression and Purification of Anti-MN IgGs Based from 3ee9 Light and Heavy CDR Variable Regions using a Stable CHO Cell Expression System Construction of Expression Vector $3ee9_{H+L}pCMV_{UCOE}8$ The kappa and heavy CDR variable regions (SEQ ID NOS: 126 and 125, respectively) from vector 3ee9 pMORPHx9 (obtained in accordance with Examples 1-3) were inserted into vector H+LpattB (ML Laboratories) as follows. Approximately 350 base pair EcoRV-BsiWI restriction enzyme fragment from 3ee9 pMORPHx9 (prepared in accordance with the previous Examples, e.g. Examples 1-3) was inserted into the EcoRV-BsiWI restriction enzyme sites of H+LpattB to generate vector 3ee9kappapAttB. Next, the approximately 350 base pair MfeI-BllpI restriction enzyme fragment from 3ee9 pMORPHx9 was inserted into the EcoRI-BlpI restriction enzyme sites of 3ee9kappapAttB to generate 3ee9H+LpattB. The 3ee9 heavy and light coding sequences (SEQ ID NOS: 126 and 125, respectively) were then recombined with pDONR221 (Invitrogen Cat.#12536-017) using Gateway BP Clonase U enzyme mix (Invitrogen Cat.#11789-100) to generate vector 3ee9H+LpENTR. Vector $3ee9_{H+L}pCMV_{UCOE}8$ was generated by recombination between 3ee9H+LpENTR and pCMV_UCOE8_DEST using Gateway LR Clonase II enzyme mix (Invitrogen Cat.#11791-100).

The construction of pCMV_UCOE8_DEST was as follows. Gateway vector conversion cassette (Invitrogen; cat#11828-029) was inserted into the SmaI site of pCET906 to generate vector pCET906_gw. Vector pCET906 was obtained from ML Laboratories and described fully in Williams et. al., BMC Biotechnology, (2005), 5:17, which is incorporated herein by reference. The approximately 2900 base pair AgeI restriction enzyme fragment from pCET906_gw was then cloned into the AgeI site of pCET1015 to generate pCMV_UCOE8_DEST. Vector pCET1015 was also obtained from ML Laboratories and which is described in Williams et al., supra. The vector pCMV_UCOE8_DEST was propagated in an E. coli strain resistant to the ccdB toxin gene (e.g. such as those marketed as "One Shot ccdB Survival T1 cells" from Invitrogen (cat#: C7510-03)). The complete nucleotide sequence of the insert of $3ee9_{H+L}pCMV_{UCOE}8$ is shown in FIG. 29, i.e. the complete nucleotide sequence encoding an human IgG anti-MN antibody comprising the kappa and heavy CDR variable regions of SEQ ID NOS: 126 and 125, respectively, obtained from vector 3ee9 pMORPHx9.

Isolation of Cell Clone 3ee9.25

To transfect CHO-S cells with vector $3ee9_{H+L}pCMV_{UCOE}8$, 60 μg of DNA was diluted in 2 mls of CD CHO (invitrogen#10743-029) complete with 8 mM L-glutamine and HT (invitrogen) and lacking PenStrep. Next 2 mls of CD CHO complete media was added to a 250 mls erlenmeyer flask. Then, 150 μL of DMRIE-C (Invitrogen cat#10459-014) was added to the flask and incubated at RT for 10 min. The diluted DNA was then mixed with the diluted DMRIE-C, flushed with 5% $CO_2$ and incubated at RT for 30 min. During the incubation, 4 mls of CHO-S cells at $5 \times 10^6$ c/mL ($2 \times 10^7$ total cells) were prepared in CD CHO complete (no P/S). After the incubation, the cells were added to the flask with DNA-DMRIE-C complex, and then gently swirled to mix. The flask was then flushed with 5% $CO_2$ and shaken at 125 rpm at 37 C for 4 hrs. Next, 32 mls of CD CHO complete media with no Pen Strep was added to the flask, flushed with 5% $CO_2$, and then returned to shaker (37° C.) overnight. After 24 hrs, cells were counted, spun down, and resuspended in CD CHO complete plus 5.5 mL/L PenStrep with 20% conditioned media and antibiotic (12.5 μg/ml puromycin) at appropriate cell density for plating. Cells were plated at 100, 300, 900, and 2700 cells/well in 96 well plates. The plates were then incubated in a 5% $CO_2$ incubator for approximately 3 weeks. Care was taken not to disturb the plates.

Individual clones were expanded from plates having wells containing single colonies in less than 20% of the wells-on the plate. The cells were expanded to non-tissue treated 24 well plates with 1 ml selective media per well. Cells were incubated for about 1 week during which 500 μL of fresh media was added as needed. Antibody expression was tested at a single dilution to eliminate clones that do not express. Clones were tested by ELISA in duplicate using a 1:5 dilution (5 uL supernatant in 95 uL TBS/tween). Clones were eliminated that gave an OD (optical density) below 0.1. Positive clones were expanded into non-tissue treated 6 well plates. Next 5 mLs of cells seeded at $4 \times 10^4$ cells/mL. After 4 days of incubation protein expression was determined by ELISA. Clones were tested using 1:50, 1:100, 1:200, and 1:400 dilutions. Clone 3ee9.25 exhibited the highest secreted antibody concentration. The 3ee9.25 cells were transferred into a 125 mL erlenmeyer shaker flask seeding at $2 \times 10^5$ cells/mL to adapt cells to suspension growth.

Expression of the Anti-MN IgGs

Transfected CHO-S cells were seeded into a Wave 10 Liter Bioreactor (Wave Biotech, 300 Franklin Square Drive, Somerset, N.J., 08873, USA) at 500,000 cells/ml. Cells were cultured for seven days in 50% CD-CHO Media (Invitrogen 10743), 50% Sigma CHO media Number 5 (Sigma 0363), 1% FCS, 1×HT supplement (Invitrogen 11067-030), Penicillin/Streptomycin (Invitrogen 15140-122), 8 mM L-Glutamine (Invitrogen 25030-081), and 12.5 μg/ml Puromycin (BD 631305) with the bioreactor rocking at 25 rpm under a 5% $CO_2$ atmosphere at 37° C. At the end of the fermentation period, spent culture media was harvested by centrifugation and sterile filtered (0.2 μM) prior to IgG purification.

Purification of the Anti-MN IRGs.

Typically 10 to 20 L of IgG-containing cell culture media were concentrated 2 to 5 fold using Prep-Scale TFF-2 30 kD Cartridge (Millipore). 1M Tris-Cl buffer, pH 7.5 was added to the concentrated media to the final concentration of 50 mM. 5.0 M NaCl was then added to a final concentration of 150 mM. The concentrated media was typically loaded onto a 30 mL Protein Sepharose column equilibrated with PBS, pH 7.4. The column was washed with PBS pH 7.4 containing 0.1% Tween 20 and 1 mM EDTA. The column was then washed with PBS and eluted with 100 mM glycine buffer pH 3.0. Upon collection the fractions were neutralized to pH 7.5 with 1M Tris-Cl pH 7.8. The purified IgGs were transferred into PBS by dialysis and sterilized by filtration (0.2 µM). Final purified antibody preparations were adjusted to between 1 and 5 mg/mL, exhibited a purity of ≧95% as determined by SDS PAGE gels stained with coomassie blue, whereupon the protein migrated as two bands corresponding to the heavy chains of Mr=50 kDa and the light chains of Mr 25 kDa, had endotoxin levels of less then 1 EU/mg of protein, and less than 10% protein aggregate as determined by SEC HPLC. Preparations were also subjected to functional Q.C. for MN antigen binding by surface plasmon resonance, binding to MN-expressing cells by FACS, and internalization into the MN-expressing cells as determined by automated imaging (Cellomics). A 20 L combined fermentation typically yielded 1 gram of purified protein with an overall recovery of 50 to 75%. N-terminal sequencing of 255 µmol of the final preparation of purified full length 3ee9 antibody using an ABI Procise 494 HT sequencer yielded 368 µmol of the following expected sequence for the mature kappa light chain of: DIQMTQSPSSLSASVGDRVTI-TRASQDINNYLSWYQQKP-. This is the same as the N-terminal sequence of corresponding to the mature Vkappal light chain of mAb 3ee9 (SEQ ID NO: 146). The heavy chain was not detected by Edman sequencing showing that its sequence was blocked.

\*\*\*

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An antibody or antibody fragment having an antigenic binding site specifically directed against an MN protein, wherein the antigenic binding site of said antibody or antibody fragment comprises a heavy chain variable region comprising complementarity determining regions (CDRs) having the amino acid sequences of SEQ ID NOs: 57, 63, and 70 and a light chain variable region comprising CDRs having the amino acid sequences of SEQ ID NOs: 89, 93, and 97.

2. The antibody or antibody fragment according to claim 1, wherein the antibody or antibody fragment binds to the MN protein with a dissociation constant of about 0.15 nM to about 50 nM.

3. The antibody or antibody fragment according to claim 1, wherein the antibody is an IgG.

4. The antibody or antibody fragment according to claim 1, wherein the antibody is an IgG1, IgG2a, IgG2b, IgG3, IgM, IgD, IgE, IgA, IgM Fab fragment, F(ab')2 fragment, scFv fragment, Fv fragment, a diabody, linear antibody, single-chain antibody, bispecific antibody, chimeric antibody, or multispecific antibody.

5. The antibody or antibody fragment according to claim 1, wherein the antibody or antibody fragment is humanized.

6. A composition comprising an antibody or antibody fragment thereof according to claim 1 and one or more pharmaceutical auxiliary substances.

7. A composition reactive against MN protein comprising an antibody or antibody fragment having an antigenic binding site specifically directed against an MN protein conjugated to one or more cytotoxic agents, wherein the antigenic binding site of said antibody or antibody fragment comprises a heavy chain variable region comprising complementarity determining regions (CDRs) having the amino acid sequences of SEQ ID NOs: 57, 63, and 70 and a light chain variable region comprising CDRs having the amino acid sequences of SEQ ID NOs: 89, 93, and 97.

8. The composition according to claim 7, wherein the one or more cytotoxic agents is selected from the group consisting of: monomethylauristatin-E, monomethylauristatin-F, aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5'—O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, Pseudomonas exotoxin, and Pseudomonas endotoxin.

9. The composition according to claim 7, wherein one of the cytotoxic agents is monomethylauristatin-E.

10. The composition according to claim 7, wherein the antibody or antibody fragment binds to the MN protein with a dissociation constant of about 0.15 nM to about 50 nM.

11. The composition according to claim 7, wherein the antibody is an IgG.

12. The antibody or antibody fragment according to claim 7, wherein the antibody is an IgG1, IgG2a, IgG2b, IgG3, IgM, IgD, IgE, IgA, IgM Fab fragment, F(ab')2 fragment, scFv fragment, Fv fragment, a diabody, linear antibody, single-chain antibody, bispecific antibody, chimeric antibody, or multispecific antibody.

13. The antibody or antibody fragment according to claim 7, wherein the antibody or antibody fragment is humanized.

14. A composition for treating a subject having an MN-expressing cancer, said composition comprising an anti-cancer agent and an antibody or antibody fragment thereof having an antigenic binding site specifically directed against an MN protein coniugated to a cytotoxic agent, wherein the antigenic binding site of said antibody or antibody fragment comprises a heavy chain variable region comprising complementarity determining regions (CDRs) having the amino acid sequences of SEQ ID NOs: 57, 63, and 70 and a light chain variable region comprising CDRs having the amino acid sequences of SEQ ID NOs: 89, 93, and 97.

15. The composition according to claim 14, wherein the anti-cancer agent is selected from the group consisting of: capecitabine, bleomycin, docetaxel (Taxotere™), doxorubicin, edatrexate, erlotinib (Tarceva™), etoposide, finasteride (Proscar™), flutamide (Eulexin), gemcitabine (Gemzar™), genitinib (Irresa), goserelin acetate (Zoladex™), granisetron (Kytril™), imatinib (Gleevec™), irinotecan (Campto/Camptosar™), ondansetron (Zofran™), paclitaxel (Taxol™), pegaspargase (Oncaspar™), pilocarpine hydrochloride (Salagen™), porfimer sodium (Photofrin™), interleukin-2 (Proleukin™), rituximab (Rituxan™), topotecan (Hycamtin™), trastuzumab (Herceptin™), Triapine™, vincristine, vinorelbine tartrate (Navelbine™), and therapeutic antibodies or fragments thereof.

16. The composition according to claim 14, wherein the anti-cancer agent is an anti-angiogenic agent selected from the group consisting of angiostatin, bevacizumab (Avastin®), sorafenib (Nexavar®), baculostatin, canstatin, maspin, anti-VEGF antibodies or peptides, anti-placental growth factor antibodies or peptides, anti-Flk-1 antibodies, anti-Flt-1 antibodies or peptides, laminin peptides, fibronectin peptides, plasminogen activator inhibitors, tissue metalloproteinase inhibitors, interferons, interleukin 12, IP-10, Gro-13, thrombospondin, 2-methoxyoestradiol, proliferin-related protein, carboxiamidotriazole, CM101, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, accutin, cidofovir, vincristine, bleomycin, AGM-1470, platelet factor 4 and minocycline.

17. The composition according to claim 14, wherein the anti-cancer agent is an agent that blocks or inhibits a multi-drug resistance phenotype selected from the group consisting of tamoxifen, verapamil and cyclosporin A.

18. The composition according to claim 14, wherein the cytotoxic agent is monomethylauristatin-E.

19. The composition according to claim 14, wherein the antibody or antibody fragment binds to the MN protein with a dissociation constant of about 0.15 nM to about 50 nM.

20. The composition according to claim 14, wherein the antibody is an IgG.

21. The composition according to claim 14, wherein the antibody is an IgG1, IgG2a, IgG2b, IgG3, IgM, IgD, IgE, IgA, IgM Fab fragment, F(ab')2 fragment, scFv fragment, Fv fragment, a diabody, linear antibody, single-chain antibody, bispecific antibody, chimeric antibody, or multispecific antibody.

22. The composition according to claim 14, wherein the antibody or antibody fragment is humanized.

23. The composition according to claim 14, wherein the cancer is in the form of a solid tumor.

24. The composition according to claim 23, wherein the solid tumor is in or originating from the breast, respiratory tract, lung, brain, reproductive organ, digestive tract, colon, urinary tract, kidney, esophagus, cervix, eye, liver, skin, head, neck, thyroid, or parathyroid.

25. A kit comprising the antibody or antibody fragment according to claim 1 and a set of instructions for using the kit.

26. A kit comprising the composition according to claim 7 and a set of instructions for using the kit.

27. A kit comprising the composition according to claim 14 and a set of instructions for using the kit.

28. An antibody or antibody fragment having an antigenic binding site specifically directed against an MN protein, wherein the antigenic binding site of said antibody or antibody fragment comprises a heavy chain variable region comprising SEQ ID NO:145 and a light chain variable region comprising SEQ ID NO:146.

29. An anti-MN IgG antibody encoded by the nucleotide sequence of SEQ ID NO: 153, wherein said antibody comprises a heavy chain variable region comprising SEQ ID NO: 145 and a light chain variable region comprising SEQ ID NO: 146.

* * * * *

SEQUENCE LISTING

```
<160> NUMBER OF SEQ ID NOS: 153

<210> SEQ ID NO 1
<211> LENGTH: 30
<212> TYPE: DNA
<213> ORGANISM: Homo sapiens

<400> SEQUENCE: 1
ggatttacct tttcttctta tggtatgtct                                       30

<210> SEQ ID NO 2
<211> LENGTH: 30
<212> TYPE: DNA
<213> ORGANISM: Homo sapiens

<400> SEQUENCE: 2
ggatttacct tttcttctta tggtatgcat                                       30

<210> SEQ ID NO 3
<211> LENGTH: 30
<212> TYPE: DNA
<213> ORGANISM: Homo sapiens

<400> SEQUENCE: 3
ggatttacct tttctaataa tgctatgaat                                       30

<210> SEQ ID NO 4
<211> LENGTH: 30
<212> TYPE: DNA
<213> ORGANISM: Homo sapiens

<400> SEQUENCE: 4
ggatttacct tttctgatta ttctattaat                                       30

<210> SEQ ID NO 5
<211> LENGTH: 30
<212> TYPE: DNA
<213> ORGANISM: Homo sapiens
```

<400> SEQUENCE: 5
ggatttacct tttcttctta tggtatttct                                     30

<210> SEQ ID NO 6
<211> LENGTH: 30
<212> TYPE: DNA
<213> ORGANISM: Homo sapiens

<400> SEQUENCE: 6
ggatttacct tttctaatta tggtatttct                                     30

<210> SEQ ID NO 7
<211> LENGTH: 51
<212> TYPE: DNA
<213> ORGANISM: Homo sapiens

<400> SEQUENCE: 7
ggtatctctt ctcttggtag cactacctat tatgcggata gcgtgaaagg c             51

<210> SEQ ID NO 8
<211> LENGTH: 51
<212> TYPE: DNA
<213> ORGANISM: Homo sapiens

<400> SEQUENCE: 8
gctatctctt attcttctag ctctacctct tatgcggata gcgtgaaagg c             51

<210> SEQ ID NO 9
<211> LENGTH: 51
<212> TYPE: DNA
<213> ORGANISM: Homo sapiens

<400> SEQUENCE: 9
ggtatctctt atgattctag caagacctat tatgcggata gcgtgaaagg c             51

<210> SEQ ID NO 10
<211> LENGTH: 51
<212> TYPE: DNA
<213> ORGANISM: Homo sapiens

<400> SEQUENCE: 10
aatatctctt attctggtag ctctacctat tatgcggata gcgtgaaagg c             51

<210> SEQ ID NO 11
<211> LENGTH: 51
<212> TYPE: DNA
<213> ORGANISM: Homo sapiens

<400> SEQUENCE: 11
ggtatctctt attctggtag ctctacctat tatgcggata gcgtgaaagg c             51

<210> SEQ ID NO 12
<211> LENGTH: 51
<212> TYPE: DNA
<213> ORGANISM: Homo sapiens

<400> SEQUENCE: 12
tctatctctt attctggtag caatacctat tatgcggata gcgtgaaagg c             51

<210> SEQ ID NO 13
<211> LENGTH: 51
<212> TYPE: DNA
<213> ORGANISM: Homo sapiens

```
<400> SEQUENCE: 13
gctatctctt attatggtag caataccctat tatgcggata gcgtgaaagg c        51

<210> SEQ ID NO 14
<211> LENGTH: 36
<212> TYPE: DNA
<213> ORGANISM: Homo sapiens

<400> SEQUENCE: 14
actggttctc ctggtacttt tatgcatggt gatcat                          36

<210> SEQ ID NO 15
<211> LENGTH: 24
<212> TYPE: DNA
<213> ORGANISM: Homo sapiens

<400> SEQUENCE: 15
ctttcttata ctggttttgc tgtt                                       24

<210> SEQ ID NO 16
<211> LENGTH: 24
<212> TYPE: DNA
<213> ORGANISM: Homo sapiens

<400> SEQUENCE: 16
cttacttata ctggtgctta tcgt                                       24

<210> SEQ ID NO 17
<211> LENGTH: 27
<212> TYPE: DNA
<213> ORGANISM: Homo sapiens

<400> SEQUENCE: 17
tttaagtatt ctggtggttc tgattct                                    27

<210> SEQ ID NO 18
<211> LENGTH: 39
<212> TYPE: DNA
<213> ORGANISM: Homo sapiens

<400> SEQUENCE: 18 cttaagccctt atcgtcataa gaatggttgg tttgattat                      39

<210> SEQ ID NO 19
<211> LENGTH: 33
<212> TYPE: DNA
<213> ORGANISM: Homo sapiens

<400> SEQUENCE: 19
atgaagccta tgcgtggtta ttctggtgct gtt                             33

<210> SEQ ID NO 20
<211> LENGTH: 24
<212> TYPE: DNA
<213> ORGANISM: Homo sapiens

<400> SEQUENCE: 20
cttaagggtg gttctggttt tgtt                                       24

<210> SEQ ID NO 21
<211> LENGTH: 30
<212> TYPE: DNA
<213> ORGANISM: Homo sapiens
```

```
<400> SEQUENCE: 21
ggatatacct ttactactaa ttatatgcat                              30

<210> SEQ ID NO 22
<211> LENGTH: 51
<212> TYPE: DNA
<213> ORGANISM: Homo sapiens

<400> SEQUENCE: 22
attatcaatc cgcataatgg ctctacgtct tacgcgcaga agtttcaggg c       51

<210> SEQ ID NO 23
<211> LENGTH: 24
<212> TYPE: DNA
<213> ORGANISM: Homo sapiens

<400> SEQUENCE: 23
ggtcgttatt ttcttatgga tgtt                                    24

<210> SEQ ID NO 24
<211> LENGTH: 30
<212> TYPE: DNA
<213> ORGANISM: Homo sapiens

<400> SEQUENCE: 24
ggatattcct tttctaagta ttggattggt                              30

<210> SEQ ID NO 25
<211> LENGTH: 27
<212> TYPE: DNA
<213> ORGANISM: Homo sapiens

<400> SEQUENCE: 25
ggatattcct ttactggtta tatttct                                 27

<210> SEQ ID NO 26
<211> LENGTH: 51
<212> TYPE: DNA
<213> ORGANISM: Homo sapiens

<400> SEQUENCE: 26
attatctatc cgactgatag ctatacccgt tattctccga gctttcaggg c       51

<210> SEQ ID NO 27
<211> LENGTH: 51
<212> TYPE: DNA
<213> ORGANISM: Homo sapiens

<400> SEQUENCE: 27
attatctatc cgggtgatag ctataccaat tattctccga gctttcaggg c       51

<210> SEQ ID NO 28
<211> LENGTH: 36
<212> TYPE: DNA
<213> ORGANISM: Homo sapiens

<400> SEQUENCE: 28
actcatggtt attataagaa tggtcgtatg gatgtt                       36

<210> SEQ ID NO 29
<211> LENGTH: 33
<212> TYPE: DNA
<213> ORGANISM: Homo sapiens
```

```
<400> SEQUENCE: 29
tattctggtc ctaattggga tgttatggat tct                                     33

<210> SEQ ID NO 30
<211> LENGTH: 33
<212> TYPE: DNA
<213> ORGANISM: Homo sapiens

<400> SEQUENCE: 30
agagcgagcc agaatattct ttcttatctg aat                                     33

<210> SEQ ID NO 31
<211> LENGTH: 33
<212> TYPE: DNA
<213> ORGANISM: Homo sapiens

<400> SEQUENCE: 31
agagcgagcc agaatatttc taattatctg aat                                     33

<210> SEQ ID NO 32
<211> LENGTH: 33
<212> TYPE: DNA
<213> ORGANISM: Homo sapiens

<400> SEQUENCE: 32
agagcgagcc aggatatttc taatcgtctg gct                                     33

<210> SEQ ID NO 33
<211> LENGTH: 33
<212> TYPE: DNA
<213> ORGANISM: Homo sapiens

<400> SEQUENCE: 33
agagcgagcc aggatattaa taattatctg tct                                     33

<210> SEQ ID NO 34
<211> LENGTH: 24
<212> TYPE: DNA
<213> ORGANISM: Homo sapiens

<400> SEQUENCE: 34
tatgctgctt cttctttgca aagc                                               24

<210> SEQ ID NO 35
<211> LENGTH: 24
<212> TYPE: DNA
<213> ORGANISM: Homo sapiens

<400> SEQUENCE: 35
cataaggttt ctaatttgca aagc                                               24

<210> SEQ ID NO 36
<211> LENGTH: 24
<212> TYPE: DNA
<213> ORGANISM: Homo sapiens

<400> SEQUENCE: 36
tatgatgcta attctttgca aagc                                               24

<210> SEQ ID NO 37
<211> LENGTH: 24
<212> TYPE: DNA
<213> ORGANISM: Homo sapiens
```

```
<400> SEQUENCE: 37
tatggtgctt ctaatttgca aagc                                          24

<210> SEQ ID NO 38
<211> LENGTH: 21
<212> TYPE: DNA
<213> ORGANISM: Homo sapiens

<400> SEQUENCE: 38
cagcagtatg gttctgttcc t                                             21

<210> SEQ ID NO 39
<211> LENGTH: 24
<212> TYPE: DNA
<213> ORGANISM: Homo sapiens

<400> SEQUENCE: 39
cttcagtatg atgattttcc tcgt                                          24

<210> SEQ ID NO 40
<211> LENGTH: 18
<212> TYPE: DNA
<213> ORGANISM: Homo sapiens

<400> SEQUENCE: 40
tttcagtatt ctggtcct                                                 18

<210> SEQ ID NO 41
<211> LENGTH: 24
<212> TYPE: DNA
<213> ORGANISM: Homo sapiens

<400> SEQUENCE: 41
cagcagtatt atggtcgtcc tact                                          24

<210> SEQ ID NO 42
<211> LENGTH: 48
<212> TYPE: DNA
<213> ORGANISM: Homo sapiens

<400> SEQUENCE: 42
agaagcagcc aaagcctggt ttattctaat ggcaatacta ctctgtct                48

<210> SEQ ID NO 43
<211> LENGTH: 48
<212> TYPE: DNA
<213> ORGANISM: Homo sapiens

<400> SEQUENCE: 43
agaagcagcc aaagcctggt tcattctaat ggctataatt atctgtct                48

<210> SEQ ID NO 44
<211> LENGTH: 24
<212> TYPE: DNA
<213> ORGANISM: Homo sapiens

<400> SEQUENCE: 44
tatggtgttt ctaatcgtgc cagt                                          24

<210> SEQ ID NO 45
<211> LENGTH: 24
<212> TYPE: DNA
<213> ORGANISM: Homo sapiens
```

```
<400> SEQUENCE: 45
tatcttggtt ctaatcgtgc cagt                                           24

<210> SEQ ID NO 46
<211> LENGTH: 24
<212> TYPE: DNA
<213> ORGANISM: Homo sapiens

<400> SEQUENCE: 46
cagcagtata attctttttcc tcgt                                          24

<210> SEQ ID NO 47
<211> LENGTH: 24
<212> TYPE: DNA
<213> ORGANISM: Homo sapiens

<400> SEQUENCE: 47
catcagtatg gtgattttc tgat                                            24

<210> SEQ ID NO 48
<211> LENGTH: 39
<212> TYPE: DNA
<213> ORGANISM: Homo sapiens

<400> SEQUENCE: 48
agcggcagca gcagcaacat tggttcttat tatgtgaat                           39

<210> SEQ ID NO 49
<211> LENGTH: 33
<212> TYPE: DNA
<213> ORGANISM: Homo sapiens

<400> SEQUENCE: 49
cttctgattt atgctgatga taagcgtccc tca                                 33

<210> SEQ ID NO 50
<211> LENGTH: 30
<212> TYPE: DNA
<213> ORGANISM: Homo sapiens

<400> SEQUENCE: 50
cagtcttatg attctactaa ggatgattct                                     30

<210> SEQ ID NO 51
<211> LENGTH: 33
<212> TYPE: DNA
<213> ORGANISM: Homo sapiens

<400> SEQUENCE: 51
agcggcgata atcttggttc ttattatgtt cat                                 33

<210> SEQ ID NO 52
<211> LENGTH: 33
<212> TYPE: DNA
<213> ORGANISM: Homo sapiens

<400> SEQUENCE: 52
agcggcgata atcttcctga tttttatgtt cat                                 33

<210> SEQ ID NO 53
<211> LENGTH: 33
<212> TYPE: DNA
<213> ORGANISM: Homo sapiens
```

```
<400> SEQUENCE: 53
cttgtgattt atgatgataa taatcgtccc tca                              33

<210> SEQ ID NO 54
<211> LENGTH: 33
<212> TYPE: DNA
<213> ORGANISM: Homo sapiens

<400> SEQUENCE: 54
cttgtgattt ctgaggataa taagcgtccc tca                              33

<210> SEQ ID NO 55
<211> LENGTH: 24
<212> TYPE: DNA
<213> ORGANISM: Homo sapiens

<400> SEQUENCE: 55
cagtcttatg attttggtaa ggtt                                        24

<210> SEQ ID NO 56
<211> LENGTH: 30
<212> TYPE: DNA
<213> ORGANISM: Homo sapiens

<400> SEQUENCE: 56
tctacttatg gttatactta ttcttattct                                  30

<210> SEQ ID NO 57
<211> LENGTH: 10
<212> TYPE: PRT
<213> ORGANISM: Homo sapiens

<400> SEQUENCE: 57

Gly Phe Thr Phe Ser Ser Tyr Gly Met Ser
1               5                   10

<210> SEQ ID NO 58
<211> LENGTH: 10
<212> TYPE: PRT
<213> ORGANISM: Homo sapiens

<400> SEQUENCE: 58

Gly Phe Thr Phe Ser Ser Tyr Gly Met His
1               5                   10

<210> SEQ ID NO 59
<211> LENGTH: 10
<212> TYPE: PRT
<213> ORGANISM: Homo sapiens

<400> SEQUENCE: 59

Gly Phe Thr Phe Ser Asn Asn Ala Met Asn
1               5                   10

<210> SEQ ID NO 60
<211> LENGTH: 10
<212> TYPE: PRT
<213> ORGANISM: Homo sapiens

<400> SEQUENCE: 60

Gly Phe Thr Phe Ser Asp Tyr Ser Ile Asn
1               5                   10

<210> SEQ ID NO 61
```

```
<211> LENGTH: 10
<212> TYPE: PRT
<213> ORGANISM: Homo sapiens

<400> SEQUENCE: 61

Gly Phe Thr Phe Ser Ser Tyr Gly Ile Ser
1               5                   10

<210> SEQ ID NO 62
<211> LENGTH: 10
<212> TYPE: PRT
<213> ORGANISM: Homo sapiens

<400> SEQUENCE: 62

Gly Phe Thr Phe Ser Asn Tyr Gly Ile Ser
1               5                   10

<210> SEQ ID NO 63
<211> LENGTH: 17
<212> TYPE: PRT
<213> ORGANISM: Homo sapiens

<400> SEQUENCE: 63

Gly Ile Ser Ser Leu Gly Ser Thr Thr Tyr Tyr Ala Asp Ser Val Lys
1               5                   10                  15

Gly

<210> SEQ ID NO 64
<211> LENGTH: 17
<212> TYPE: PRT
<213> ORGANISM: Homo sapiens

<400> SEQUENCE: 64

Ala Ile Ser Tyr Ser Ser Ser Thr Ser Tyr Ala Asp Ser Val Lys
1               5                   10                  15

Gly

<210> SEQ ID NO 65
<211> LENGTH: 17
<212> TYPE: PRT
<213> ORGANISM: Homo sapiens

<400> SEQUENCE: 65

Gly Ile Ser Tyr Asp Ser Ser Lys Thr Tyr Tyr Ala Asp Ser Val Lys
1               5                   10                  15

Gly

<210> SEQ ID NO 66
<211> LENGTH: 17
<212> TYPE: PRT
<213> ORGANISM: Homo sapiens

<400> SEQUENCE: 66

Asn Ile Ser Tyr Ser Gly Ser Ser Thr Tyr Tyr Ala Asp Ser Val Lys
1               5                   10                  15

Gly

<210> SEQ ID NO 67
<211> LENGTH: 17
<212> TYPE: PRT
<213> ORGANISM: Homo sapiens

<400> SEQUENCE: 67
```

```
Gly Ile Ser Tyr Ser Gly Ser Ser Thr Tyr Tyr Ala Asp Ser Val Lys
1               5                   10                  15

Gly

<210> SEQ ID NO 68
<211> LENGTH: 17
<212> TYPE: PRT
<213> ORGANISM: Homo sapiens

<400> SEQUENCE: 68

Ser Ile Ser Tyr Ser Gly Ser Asn Thr Tyr Tyr Ala Asp Ser Val Lys
1               5                   10                  15

Gly

<210> SEQ ID NO 69
<211> LENGTH: 17
<212> TYPE: PRT
<213> ORGANISM: Homo sapiens

<400> SEQUENCE: 69

Ala Ile Ser Tyr Tyr Gly Ser Asn Thr Tyr Tyr Ala Asp Ser Val Lys
1               5                   10                  15

Gly

<210> SEQ ID NO 70
<211> LENGTH: 12
<212> TYPE: PRT
<213> ORGANISM: Homo sapiens

<400> SEQUENCE: 70

Thr Gly Ser Pro Gly Thr Phe Met His Gly Asp His
1               5                   10

<210> SEQ ID NO 71
<211> LENGTH: 8
<212> TYPE: PRT
<213> ORGANISM: Homo sapiens

<400> SEQUENCE: 71

Leu Ser Tyr Thr Gly Phe Ala Val
1               5

<210> SEQ ID NO 72
<211> LENGTH: 8
<212> TYPE: PRT
<213> ORGANISM: Homo sapiens

<400> SEQUENCE: 72

Leu Thr Tyr Thr Gly Ala Tyr Arg
1               5

<210> SEQ ID NO 73
<211> LENGTH: 9
<212> TYPE: PRT
<213> ORGANISM: Homo sapiens

<400> SEQUENCE: 73

Phe Lys Tyr Ser Gly Gly Ser Asp Ser
1               5

<210> SEQ ID NO 74
<211> LENGTH: 13
<212> TYPE: PRT
<213> ORGANISM: Homo sapiens
```

<400> SEQUENCE: 74

Leu Lys Pro Tyr Arg His Lys Asn Gly Trp Phe Asp Tyr
1               5                   10

<210> SEQ ID NO 75
<211> LENGTH: 11
<212> TYPE: PRT
<213> ORGANISM: Homo sapiens

<400> SEQUENCE: 75

Met Lys Pro Met Arg Gly Tyr Ser Gly Ala Val
1               5                   10

<210> SEQ ID NO 76
<211> LENGTH: 8
<212> TYPE: PRT
<213> ORGANISM: Homo sapiens

<400> SEQUENCE: 76

Leu Lys Gly Gly Ser Gly Phe Val
1               5

<210> SEQ ID NO 77
<211> LENGTH: 10
<212> TYPE: PRT
<213> ORGANISM: Homo sapiens

<400> SEQUENCE: 77

Gly Tyr Thr Phe Thr Thr Asn Tyr Met His
1               5                   10

<210> SEQ ID NO 78
<211> LENGTH: 17
<212> TYPE: PRT
<213> ORGANISM: Homo sapiens

<400> SEQUENCE: 78

Ile Ile Asn Pro His Asn Gly Ser Thr Ser Tyr Ala Gln Lys Phe Gln
1               5                   10                  15
Gly

<210> SEQ ID NO 79
<211> LENGTH: 8
<212> TYPE: PRT
<213> ORGANISM: Homo sapiens

<400> SEQUENCE: 79

Gly Arg Tyr Phe Leu Met Asp Val
1               5

<210> SEQ ID NO 80
<211> LENGTH: 10
<212> TYPE: PRT
<213> ORGANISM: Homo sapiens

<400> SEQUENCE: 80

Gly Tyr Ser Phe Ser Lys Tyr Trp Ile Gly
1               5                   10

<210> SEQ ID NO 81
<211> LENGTH: 9
<212> TYPE: PRT
<213> ORGANISM: Homo sapiens

```
<400> SEQUENCE: 81

Gly Tyr Ser Phe Thr Gly Tyr Ile Ser
1               5

<210> SEQ ID NO 82
<211> LENGTH: 17
<212> TYPE: PRT
<213> ORGANISM: Homo sapiens

<400> SEQUENCE: 82

Ile Ile Tyr Pro Thr Asp Ser Tyr Thr Arg Tyr Ser Pro Ser Phe Gln
1               5                   10                  15

Gly

<210> SEQ ID NO 83
<211> LENGTH: 17
<212> TYPE: PRT
<213> ORGANISM: Homo sapiens

<400> SEQUENCE: 83

Ile Ile Tyr Pro Gly Asp Ser Tyr Thr Asn Tyr Ser Pro Ser Phe Gln
1               5                   10                  15

Gly

<210> SEQ ID NO 84
<211> LENGTH: 12
<212> TYPE: PRT
<213> ORGANISM: Homo sapiens

<400> SEQUENCE: 84

Thr His Gly Tyr Tyr Lys Asn Gly Arg Met Asp Val
1               5                   10

<210> SEQ ID NO 85
<211> LENGTH: 11
<212> TYPE: PRT
<213> ORGANISM: Homo sapiens

<400> SEQUENCE: 85

Tyr Ser Gly Pro Asn Trp Asp Val Met Asp Ser
1               5                   10

<210> SEQ ID NO 86
<211> LENGTH: 11
<212> TYPE: PRT
<213> ORGANISM: Homo sapiens

<400> SEQUENCE: 86

Arg Ala Ser Gln Asn Ile Leu Ser Tyr Leu Asn
1               5                   10

<210> SEQ ID NO 87
<211> LENGTH: 11
<212> TYPE: PRT
<213> ORGANISM: Homo sapiens

<400> SEQUENCE: 87

Arg Ala Ser Gln Asn Ile Ser Asn Tyr Leu Asn
1               5                   10

<210> SEQ ID NO 88
<211> LENGTH: 11
<212> TYPE: PRT
```

<400> SEQUENCE: 88

Arg Ala Ser Gln Asp Ile Ser Asn Arg Leu Ala
1               5                   10

<210> SEQ ID NO 89
<211> LENGTH: 11
<212> TYPE: PRT
<213> ORGANISM: Homo sapiens

<400> SEQUENCE: 89

Arg Ala Ser Gln Asp Ile Asn Asn Tyr Leu Ser
1               5                   10

<210> SEQ ID NO 90
<211> LENGTH: 8
<212> TYPE: PRT
<213> ORGANISM: Homo sapiens

<400> SEQUENCE: 90

Tyr Ala Ala Ser Ser Leu Gln Ser
1               5

<210> SEQ ID NO 91
<211> LENGTH: 8
<212> TYPE: PRT
<213> ORGANISM: Homo sapiens

<400> SEQUENCE: 91

His Lys Val Ser Asn Leu Gln Ser
1               5

<210> SEQ ID NO 92
<211> LENGTH: 8
<212> TYPE: PRT
<213> ORGANISM: Homo sapiens

<400> SEQUENCE: 92

Tyr Asp Ala Asn Ser Leu Gln Ser
1               5

<210> SEQ ID NO 93
<211> LENGTH: 8
<212> TYPE: PRT
<213> ORGANISM: Homo sapiens

<400> SEQUENCE: 93

Tyr Gly Ala Ser Asn Leu Gln Ser
1               5

<210> SEQ ID NO 94
<211> LENGTH: 7
<212> TYPE: PRT
<213> ORGANISM: Homo sapiens

<400> SEQUENCE: 94

Gln Gln Tyr Gly Ser Val Pro
1               5

<210> SEQ ID NO 95
<211> LENGTH: 8
<212> TYPE: PRT
<213> ORGANISM: Homo sapiens

<400> SEQUENCE: 95

```
Leu Gln Tyr Asp Asp Phe Pro Arg
1               5
```

<210> SEQ ID NO 96
<211> LENGTH: 6
<212> TYPE: PRT
<213> ORGANISM: Homo sapiens

<400> SEQUENCE: 96

```
Phe Gln Tyr Ser Gly Pro
1               5
```

<210> SEQ ID NO 97
<211> LENGTH: 8
<212> TYPE: PRT
<213> ORGANISM: Homo sapiens

<400> SEQUENCE: 97

```
Gln Gln Tyr Tyr Gly Arg Pro Thr
1               5
```

<210> SEQ ID NO 98
<211> LENGTH: 16
<212> TYPE: PRT
<213> ORGANISM: Homo sapiens

<400> SEQUENCE: 98

```
Arg Ser Ser Gln Ser Leu Val Tyr Ser Asn Gly Asn Thr Thr Leu Ser
1               5                   10                  15
```

<210> SEQ ID NO 99
<211> LENGTH: 16
<212> TYPE: PRT
<213> ORGANISM: Homo sapiens

<400> SEQUENCE: 99

```
Arg Ser Ser Gln Ser Leu Val His Ser Asn Gly Tyr Asn Tyr Leu Ser
1               5                   10                  15
```

<210> SEQ ID NO 100
<211> LENGTH: 8
<212> TYPE: PRT
<213> ORGANISM: Homo sapiens

<400> SEQUENCE: 100

```
Tyr Gly Val Ser Asn Arg Ala Ser
1               5
```

<210> SEQ ID NO 101
<211> LENGTH: 8
<212> TYPE: PRT
<213> ORGANISM: Homo sapiens

<400> SEQUENCE: 101

```
Tyr Leu Gly Ser Asn Arg Ala Ser
1               5
```

<210> SEQ ID NO 102
<211> LENGTH: 8
<212> TYPE: PRT
<213> ORGANISM: Homo sapiens

<400> SEQUENCE: 102

```
Gln Gln Tyr Asn Ser Phe Pro Arg
1               5
```

<210> SEQ ID NO 103
<211> LENGTH: 8
<212> TYPE: PRT
<213> ORGANISM: Homo sapiens

<400> SEQUENCE: 103

His Gln Tyr Gly Asp Phe Ser Asp
1               5

<210> SEQ ID NO 104
<211> LENGTH: 13
<212> TYPE: PRT
<213> ORGANISM: Homo sapiens

<400> SEQUENCE: 104

Ser Gly Ser Ser Ser Asn Ile Gly Ser Tyr Tyr Val Asn
1               5                   10

<210> SEQ ID NO 105
<211> LENGTH: 11
<212> TYPE: PRT
<213> ORGANISM: Homo sapiens

<400> SEQUENCE: 105

Leu Leu Ile Tyr Ala Asp Asp Lys Arg Pro Ser
1               5                   10

<210> SEQ ID NO 106
<211> LENGTH: 10
<212> TYPE: PRT
<213> ORGANISM: Homo sapiens

<400> SEQUENCE: 106

Gln Ser Tyr Asp Ser Thr Lys Asp Asp Ser
1               5                   10

<210> SEQ ID NO 107
<211> LENGTH: 11
<212> TYPE: PRT
<213> ORGANISM: Homo sapiens

<400> SEQUENCE: 107

Ser Gly Asp Asn Leu Gly Ser Tyr Tyr Val His
1               5                   10

<210> SEQ ID NO 108
<211> LENGTH: 11
<212> TYPE: PRT
<213> ORGANISM: Homo sapiens

<400> SEQUENCE: 108

Ser Gly Asp Asn Leu Pro Asp Phe Tyr Val His
1               5                   10

<210> SEQ ID NO 109
<211> LENGTH: 11
<212> TYPE: PRT
<213> ORGANISM: Homo sapiens

<400> SEQUENCE: 109

Leu Val Ile Tyr Asp Asp Asn Asn Arg Pro Ser
1               5                   10

<210> SEQ ID NO 110
<211> LENGTH: 11

```
<212> TYPE: PRT
<213> ORGANISM: Homo sapiens

<400> SEQUENCE: 110

Leu Val Ile Ser Glu Asp Asn Lys Arg Pro Ser
1               5                   10

<210> SEQ ID NO 111
<211> LENGTH: 8
<212> TYPE: PRT
<213> ORGANISM: Homo sapiens

<400> SEQUENCE: 111

Gln Ser Tyr Asp Phe Gly Lys Val
1               5

<210> SEQ ID NO 112
<211> LENGTH: 10
<212> TYPE: PRT
<213> ORGANISM: Homo sapiens

<400> SEQUENCE: 112

Ser Thr Tyr Gly Tyr Thr Tyr Ser Tyr Ser
1               5                   10

<210> SEQ ID NO 113
<211> LENGTH: 347
<212> TYPE: DNA
<213> ORGANISM: Homo sapiens

<400> SEQUENCE: 113
gaattggttc agagcggcgc ggaagtgaaa aaaccgggcg cgagcgtgaa agtgagctgc      60
aaagcctccg gatatacctt tactactaat tatatgcatt gggtccgcca agcccctggg     120
cagggtctcg agtggatggg cattatcaat ccgcataatg ctctacgtc ttacgcgcag      180 aagtttcagg gccgggtgac catgacccgt gataccagca ttagcaccgc gtatatggaa     240
ctgagcagcc tgcgtagcga agatacggcc gtgtattatt gcgcgcgtgg tcgttatttt     300
cttatggatg tttggggcca aggcaccctg gtgacggtta gctcagc                   347

<210> SEQ ID NO 114
<211> LENGTH: 324
<212> TYPE: DNA
<213> ORGANISM: Homo sapiens

<400> SEQUENCE: 114
gatatccaga tgacccagag cccgtctagc ctgagcgcga gcgtgggtga tcgtgtgacc      60
attacctgca gcgcagcca gaatattctt tcttatctga attggtacca gcagaaacca     120
ggtaaagcac cgaaactatt aatttatgct gcttcttctt tgcaaagcgg ggtcccgtcc     180
cgttttagcg gctctggatc cggcactgat tttaccctga ccattagcag cctgcaacct     240
gaagactttg cggттттатта ttgccagcag tatggttctg ttcctacctt tggccagggt     300
acgaaagttg aaattaaacg tacg                                            324

<210> SEQ ID NO 115
<211> LENGTH: 347
<212> TYPE: DNA
<213> ORGANISM: Homo sapiens

<400> SEQUENCE: 115
gaattggtgg aaagcggcgg cggcctggtg caaccgggcg gcagcctgcg tctgagctgc      60
```

```
gcggcctccg gatttacctt ttctaataat gctatgaatt gggtgcgcca agcccctggg      120
aagggtctcg agtgggtgag cggtatctct tatgattcta gcaagaccta ttatgcggat      180
agcgtgaaag gccgttttac catttcacgt gataattcga aaaacaccct gtatctgcaa      240
atgaacagcc tgcgtgcgga agatacggcc gtgtattatt gcgcgcgtct tacttatact      300
ggtgcttatc gttggggcca aggcaccctg gtgacggtta gctcagc                   347

<210> SEQ ID NO 116
<211> LENGTH: 311
<212> TYPE: DNA
<213> ORGANISM: Homo sapiens

<400> SEQUENCE: 116
gatatcgaac tgacccagcc gccttcagtg agcgttgcac caggtcagac cgcgcgtatc       60
tcgtgtagcg gcgataatct tggttcttat tatgttcatt ggtaccagca gaaacccggg      120
caggcgccag ttcttgtgat ttatgatgat aataatcgtc cctcaggcat cccggaacgc      180
tttagcggat ccaacagcgg caacaccgcg accctgacca ttagcggcac tcaggcggaa      240
gacgaagcgg attattattg ccagtcttat gattttggta aggttgtgtt tggcggcggc      300
acgaagttaa c                                                           311

<210> SEQ ID NO 117
<211> LENGTH: 350
<212> TYPE: DNA
<213> ORGANISM: Homo sapiens

<400> SEQUENCE: 117
gaattggtgg aaagcggcgg cggcctggtg caaccgggcg gcagcctgcg tctgagctgc       60
gcggcctccg gatttacctt ttctgattat tctattaatt gggtgcgcca agcccctggg      120
aagggtctcg agtatgtgag caatatctct tattctggta gctctaccta ttatgcggat      180
agcgtgaaag gccgttttac catttcacgt gataattcga aaaacaccct gtatctgcaa      240
atgaacagcc tgcgtgcgga agatacggcc gtgtattatt gcgcgcgttt taagtattct      300
ggtggttctg attcttgggg ccaaggcacc ctggtgacgg ttagctcagc                 350

<210> SEQ ID NO 118
<211> LENGTH: 317
<212> TYPE: DNA
<213> ORGANISM: Homo sapiens

<400> SEQUENCE: 118
gatatcgaac tgacccagcc gccttcagtg agcgttgcac caggtcagac cgcgcgtatc       60
tcgtgtagcg gcgataatct tcctgatttt tatgttcatt ggtaccagca gaaacccggg      120
caggcgccag ttcttgtgat ttctgaggat aataagcgtc cctcaggcat cccggaacgc      180
tttagcggat ccaacagcgg caacaccgcg accctgacca ttagcggcac tcaggcggaa      240
gacgaagcgg attattattg ctctactttat ggttatactt attcttattc tgtgtttggc     300
ggcggcacga agttaac                                                     317

<210> SEQ ID NO 119
<211> LENGTH: 362
<212> TYPE: DNA
<213> ORGANISM: Homo sapiens

<400> SEQUENCE: 119
gaattggtgg aaagcggcgg cggcctggtg caaccgggcg gcagcctgcg tctgagctgc       60
```

```
gcggcctccg gatttacctt ttcttcttat ggtatttctt gggtgcgcca agcccctggg    120
aagggtctcg agtgggtgag cggtatctct tattctggta gctctaccta ttatgcggat    180
agcgtgaaag gccgttttac catttcacgt gataattcga aaacaccct gtatctgcaa     240 atgaacagcc tgcgtgcgga agatacggcc gtgtattatt gcgcgcgtct taagccttat    300
cgtcataaga atggttggtt tgattattgg ggccaaggca ccctggtgac ggttagctca    360
gc                                                                   362

<210> SEQ ID NO 120
<211> LENGTH: 327
<212> TYPE: DNA
<213> ORGANISM: Homo sapiens

<400> SEQUENCE: 120
gatatccaga tgacccagag cccgtctagc ctgagcgcga gcgtgggtga tcgtgtgacc    60
attacctgca gcgcgagcca gaatatttct aattatctga attggtacca gcagaaacca    120
ggtaaagcac cgaaactatt aattcataag gtttctaatt tgcaaagcgg ggtcccgtcc    180
cgttttagcg gctctggatc cggcactgat tttaccctga ccattagcag cctgcaacct    240
gaagactttg cggtttatta ttgccttcag tatgatgatt ttcctcgtac ctttggccag    300
ggtacgaaag ttgaaattaa acgtacg                                        327

<210> SEQ ID NO 121
<211> LENGTH: 356
<212> TYPE: DNA
<213> ORGANISM: Homo sapiens

<400> SEQUENCE: 121
gaattggtgg aaagcggcgg cggcctggtg caaccgggcg gcagcctgcg tctgagctgc    60
gcggcctccg gatttacctt ttcttcttat ggtatttctt gggtgcgcca agcccctggg    120
aagggtctcg agtgggtgag ctctatctct tattctggta gcaataccta ttatgcggat    180
agcgtgaaag gccgttttac catttcacgt gataattcga aaacaccct gtatctgcaa     240 atgaacagcc tgcgtgcgga agatacggcc gtgtattatt gcgcgcgtat gaagcctatg    300
cgtggttatt ctggtgctgt ttggggccaa ggcaccctgg tgacggttag ctcagc        356

<210> SEQ ID NO 122
<211> LENGTH: 321
<212> TYPE: DNA
<213> ORGANISM: Homo sapiens

<400> SEQUENCE: 122
gatatccaga tgacccagag cccgtctagc ctgagcgcga gcgtgggtga tcgtgtgacc    60
attacctgca gcgcgagcca ggatatttct aatcgtctgg cttggtacca gcagaaacca    120
ggtaaagcac cgaaactatt aatttatgat gctaattctt tgcaaagcgg ggtcccgtcc    180
cgttttagcg gctctggatc cggcactgat tttaccctga ccattagcag cctgcaacct    240
gaagactttg cgacttatta ttgctttcag tattctggtc ctacctttgg ccagggtacg    300
aaagttgaaa ttaaacgtac g                                              321

<210> SEQ ID NO 123
<211> LENGTH: 347
<212> TYPE: DNA
<213> ORGANISM: Homo sapiens

<400> SEQUENCE: 123
```

```
gaattggtgg aaagcggcgg cggcctggtg caaccgggcg gcagcctgcg tctgagctgc    60
gcggcctccg gatttacctt ttctaattat ggtatttctt gggtgcgcca agcccctggg   120
aagggtctcg agtgggtgag cgctatctct tattatggta gcaataccta ttatgcggat   180
agcgtgaaag gccgttttac catttcacgt gataattcga aaacacccct gtatctgcaa   240
atgaacagcc tgcgtgcgga agatacggcc gtgtattatt gcgcgcgtct aagggtggt    300 tctggttttg tttggggcca aggcaccctg gtgacggtta gctcagc                347

<210> SEQ ID NO 124
<211> LENGTH: 342
<212> TYPE: DNA
<213> ORGANISM: Homo sapiens

<400> SEQUENCE: 124
gatatcgtga tgacccagag cccactgagc ctgccagtga ctccgggcga gcctgcgagc    60
attagctgca gaagcagcca aagcctggtt tattctaatg gcaatactac tctgtcttgg   120
taccttcaaa aaccaggtca aagcccgcag ctattaattt atggtgtttc taatcgtgcc   180
agtggggtcc cggatcgttt tagcggctct ggatccggca ccgatttac cctgaaaatt   240 agccgtgtgg aagctgaaga cgtgggcgtg tattattgcc agcagtataa ttcttttcct   300
cgtacctttg gccagggtac gaaagttgaa attaaacgta cg                     342

<210> SEQ ID NO 125
<211> LENGTH: 359
<212> TYPE: DNA
<213> ORGANISM: Homo sapiens

<400> SEQUENCE: 125
gaattggtgg aaagcggcgg cggcctggtg caaccgggcg gcagcctgcg tctgagctgc    60
gcggcctccg gatttacctt ttcttcttat ggtatgtctt gggtgcgcca agcccctggg   120
aagggtctcg agtgggtgag cggtatctct tctcttggta gcactaccta ttatgcggat   180
agcgtgaaag gccgttttac catttcacgt gataattcga aaacacccct gtatctgcaa   240
atgaacagcc tgcgtgcgga agatacggcc gtgtattatt gcgcgcgtac tggttctcct   300 ggtacttttta tgcatggtga tcattggggc caaggcaccc tggtgacggt tagctcagc   359

<210> SEQ ID NO 126
<211> LENGTH: 327
<212> TYPE: DNA
<213> ORGANISM: Homo sapiens

<400> SEQUENCE: 126
gatatccaga tgacccagag cccgtctagc ctgagcgcga gcgtgggtga tcgtgtgacc    60
attacctgca gagcgagcca ggatattaat aattatctgt cttggtacca gcagaaacca   120
ggtaaagcac cgaaactatt aatttatggt gcttctaatt tgcaaagcgg ggtcccgtcc   180
cgttttagcg gctctggatc cggcactgat tttaccctga ccattagcag cctgcaacct   240
gaagactttg cggtttatta ttgccagcag tattatggtc gtcctactac ctttggccag   300
ggtacgaaag ttgaaattaa acgtacg                                       327

<210> SEQ ID NO 127
<211> LENGTH: 359
<212> TYPE: DNA
<213> ORGANISM: Homo sapiens

<400> SEQUENCE: 127
```

```
gaattggttc agagcggcgc ggaagtgaaa aaaccgggcg aaagcctgaa aattagctgc      60
aaaggttccg atattcctt ttctaagtat tggattggtt gggtgcgcca gatgcctggg     120
aagggtctcg agtggatggg cattatctat ccgactgata gctataccccg ttattctccg    180 agctttcagg gccaggtgac cattagcgcg gataaaagca ttagcaccgc gtatcttcaa     240
tggagcagcc tgaaagcgag cgatacggcc atgtattatt gcgcgcgtac tcatggttat     300
tataagaatg gtcgtatgga tgtttggggc caaggcaccc tggtgacggt tagctcagc     359
```

<210> SEQ ID NO 128
<211> LENGTH: 342
<212> TYPE: DNA
<213> ORGANISM: Homo sapiens

<400> SEQUENCE: 128

```
gatatcgtga tgacccagag cccactgagc ctgccagtga ctccgggcga gcctgcgagc     60
attagctgca gaagcagcca aagcctggtt cattctaatg gctataatta tctgtcttgg    120
taccttcaaa aaccaggtca aagcccgcag ctattaattt atcttggttc taatcgtgcc    180 agtgggtcc cggatcgttt tagcggctct ggatccggca ccgattttac cctgaaaatt     240
agccgtgtgg aagctgaaga cgtgggcgtg tattattgcc atcagtatgg tgattttttct   300 gatacctttg gccagggtac gaaagttgaa attaaacgta cg                        342
```

<210> SEQ ID NO 129
<211> LENGTH: 353
<212> TYPE: DNA
<213> ORGANISM: Homo sapiens

<400> SEQUENCE: 129

```
gaattggttc agagcggcgc ggaagtgaaa aaaccgggcg aaagcctgaa aattagctgc     60
aaaggttccg atattcctt tactggttat atttcttggg tgcgccaagc ccctgggaag    120
ggtctcgagt ggatgggcat tatctatccg ggtgatagct ataccaatta ttctccgagc    180
tttcagggcc aggtgaccat tagcgcggat aaaagcatta gcaccgcgta tcttcaatgg    240
agcagcctga aagcgagcga tacggccatg tattattgcg cgcgttattc tggtcctaat    300
tgggatgtta tggattcttg gggccaaggc accctggtga cggttagctc agc          353
```

<210> SEQ ID NO 130
<211> LENGTH: 323
<212> TYPE: DNA
<213> ORGANISM: Homo sapiens

<400> SEQUENCE: 130

```
gatatcgtgc tgacccagcc gccttcagtg agtggcgcac aggtcagcg tgtgaccatc      60 tcgtgtagcg gcagcagcag caacattggt tcttattatg tgaattggta ccagcagttg    120
cccgggacgg cgccgaaact tctgatttat gctgatgata gcgtccctc aggcgtgccg     180 gatcgtttta gcggatccaa aagcggcacc agcgcgagcc ttgcgattac gggcctgcaa    240
agcgaagacg aagcggatta ttattgccag tcttatgatt ctactaagga tgattctgtg    300
tttggcggcg gcacgaagtt aac                                             323
```

<210> SEQ ID NO 131
<211> LENGTH: 347
<212> TYPE: DNA
<213> ORGANISM: Homo sapiens

<400> SEQUENCE: 131

```
gaattggtgg aaagcggcgg cggcctggtg caaccgggcg gcagcctgcg tctgagctgc    60
gcggcctccg gatttacctt ttcttcttat ggtatgcatt gggtgcgcca agcccctggg   120
aagggtctcg agtatgtgag cgctatctct tattcttcta gctctacctc ttatgcggat   180
agcgtgaaag gccgttttac catttcacgt gataattcga aaacaccct gtatctgcaa    240 atgaacagcc tgcgtgcgga agatacggcc gtgtattatt gcgcgcgtct ttcttatact   300
ggttttgctg tttggggcca aggcaccctg gtgacggtta gctcagc                 347

<210> SEQ ID NO 132
<211> LENGTH: 311
<212> TYPE: DNA
<213> ORGANISM: Homo sapiens

<400> SEQUENCE: 132
gatatcgaac tgacccagcc gccttcagtg agcgttgcac aggtcagac cgcgcgtatc     60 tcgtgtagcg gcgataatct tggttcttat tatgttcatt ggtaccagca gaaacccggg   120
caggcgccag ttcttgtgat ttatgatgat aataatcgtc cctcaggcat cccggaacgc   180
tttagcggat ccaacagcgg caacaccgcg accctgacca ttagcggcac tcaggcggaa   240
gacgaagcgg attattattg ccagtcttat gattttggta aggttgtgtt tggcggcggc   300
acgaagttaa c                                                        311

<210> SEQ ID NO 133
<211> LENGTH: 115
<212> TYPE: PRT
<213> ORGANISM: Homo sapiens

<400> SEQUENCE: 133

Glu Leu Val Gln Ser Gly Ala Glu Val Lys Lys Pro Gly Ala Ser Val
1               5                   10                  15

Lys Val Ser Cys Lys Ala Ser Gly Tyr Thr Phe Thr Thr Asn Tyr Met
            20                  25                  30

His Trp Val Arg Gln Ala Pro Gly Gln Gly Leu Glu Trp Met Gly Ile
        35                  40                  45

Ile Asn Pro His Asn Gly Ser Thr Ser Tyr Ala Gln Lys Phe Gln Gly
    50                  55                  60

Arg Val Thr Met Thr Arg Asp Thr Ser Ile Ser Thr Ala Tyr Met Glu
65                  70                  75                  80

Leu Ser Ser Leu Arg Ser Glu Asp Thr Ala Val Tyr Tyr Cys Ala Arg
                85                  90                  95

Gly Arg Tyr Phe Leu Met Asp Val Trp Gly Gln Gly Thr Leu Val Thr
            100                 105                 110

Val Ser Ser
        115

<210> SEQ ID NO 134
<211> LENGTH: 108
<212> TYPE: PRT
<213> ORGANISM: Homo sapiens

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Leu Ser Tyr
            20                  25                  30

Leu Asn Trp Tyr Gln Gln Lys Pro Gly Lys Ala Pro Lys Leu Leu Ile
        35                  40                  45
```

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Gly Ser Val Pro Thr
                85                  90                  95

Phe Gly Gln Gly Thr Lys Val Glu Ile Lys Arg Thr
            100                 105

<210> SEQ ID NO 135
<211> LENGTH: 115
<212> TYPE: PRT
<213> ORGANISM: Homo sapiens

<400> SEQUENCE: 135

Glu Leu Val Glu Ser Gly Gly Leu Val Gln Pro Gly Gly Ser Leu
1               5                   10                  15

Arg Leu Ser Cys Ala Ala Ser Gly Phe Thr Phe Ser Asn Asn Ala Met
                20                  25                  30

Asn Trp Val Arg Gln Ala Pro Gly Lys Gly Leu Glu Trp Val Ser Gly
            35                  40                  45

Ile Ser Tyr Asp Ser Ser Lys Thr Tyr Tyr Ala Asp Ser Val Lys Gly
50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Leu Thr Tyr Thr Gly Ala Tyr Arg Trp Gly Gln Gly Thr Leu Val Thr
            100                 105                 110

Val Ser Ser
        115

<210> SEQ ID NO 136
<211> LENGTH: 106
<212> TYPE: PRT
<213> ORGANISM: Homo sapiens

<400> SEQUENCE: 136

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Tyr Tyr Val
                20                  25                  30

His Trp Tyr Gln Gln Lys Pro Gly Gln Ala Pro Val Leu Val Ile Tyr
            35                  40                  45

Asp Asp Asn Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Phe Gly Lys Val Val
                85                  90                  95

Phe Gly Gly Gly Thr Lys Leu Thr Val Leu
            100                 105

<210> SEQ ID NO 137
<211> LENGTH: 116
<212> TYPE: PRT
<213> ORGANISM: Homo sapiens

<400> SEQUENCE: 137

```
Glu Leu Val Glu Ser Gly Gly Gly Leu Val Gln Pro Gly Gly Ser Leu
  1               5                  10                  15

Arg Leu Ser Cys Ala Ala Ser Gly Phe Thr Phe Ser Asp Tyr Ser Ile
             20                  25                  30

Asn Trp Val Arg Gln Ala Pro Gly Lys Gly Leu Glu Tyr Val Ser Asn
         35                  40                  45

Ile Ser Tyr Ser Gly Ser Ser Thr Tyr Tyr Ala Asp Ser Val Lys Gly
     50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Phe Lys Tyr Ser Gly Gly Ser Asp Ser Trp Gly Gln Gly Thr Leu Val
            100                 105                 110

Thr Val Ser Ser
            115
```

<210> SEQ ID NO 138
<211> LENGTH: 105
<212> TYPE: PRT
<213> ORGANISM: Homo sapiens

<400> SEQUENCE: 138

```
Asp Ile Glu Leu Thr Gln Pro Pro Ser Val Ser Val Ala Pro Gly Gln
  1               5                  10                  15

Thr Ala Arg Ile Ser Cys Ser Gly Asp Asn Leu Pro Asp Phe Tyr Val
             20                  25                  30

His Trp Tyr Gln Gln Lys Pro Gly Gln Ala Pro Val Leu Val Ile Ser
         35                  40                  45

Glu Asp Asn Lys Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ser Thr Tyr Gly Tyr Thr Tyr Ser Tyr
                 85                  90                  95

Ser Val Phe Gly Gly Gly Thr Lys Leu
            100                 105
```

<210> SEQ ID NO 139
<211> LENGTH: 120
<212> TYPE: PRT
<213> ORGANISM: Homo sapiens

<400> SEQUENCE: 139

```
Glu Leu Val Glu Ser Gly Gly Gly Leu Val Gln Pro Gly Gly Ser Leu
  1               5                  10                  15

Arg Leu Ser Cys Ala Ala Ser Gly Phe Thr Phe Ser Ser Tyr Gly Ile
             20                  25                  30

Ser Trp Val Arg Gln Ala Pro Gly Lys Gly Leu Glu Trp Val Ser Gly
         35                  40                  45

Ile Ser Tyr Ser Gly Ser Ser Thr Tyr Tyr Ala Asp Ser Val Lys Gly
     50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95
```

Leu Lys Pro Tyr Arg His Lys Asn Gly Trp Phe Asp Tyr Trp Gly Gln
            100                 105                 110

Gly Thr Leu Val Thr Val Ser Ser
            115                 120

<210> SEQ ID NO 140
<211> LENGTH: 109
<212> TYPE: PRT
<213> ORGANISM: Homo sapiens

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ser Asn Tyr
            20                  25                  30

Leu Asn Trp Tyr Gln Gln Lys Pro Gly Lys Ala Pro Lys Leu Leu Ile
        35                  40                  45

His Lys Val Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Leu Gln Tyr Asp Asp Phe Pro Arg
                85                  90                  95

Thr Phe Gly Gln Gly Thr Lys Val Glu Ile Lys Arg Thr
            100                 105

<210> SEQ ID NO 141
<211> LENGTH: 118
<212> TYPE: PRT
<213> ORGANISM: Homo sapiens

<400> SEQUENCE: 141

Glu Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Gly Ile
            20                  25                  30

Ser Trp Val Arg Gln Ala Pro Gly Lys Gly Leu Glu Trp Val Ser Ser
        35                  40                  45

Ile Ser Tyr Ser Gly Ser Asn Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Met Lys Pro Met Arg Gly Tyr Ser Gly Ala Val Trp Gly Gln Gly Thr
            100                 105                 110

Leu Val Thr Val Ser Ser
        115

<210> SEQ ID NO 142
<211> LENGTH: 107
<212> TYPE: PRT
<213> ORGANISM: Homo sapiens

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Arg

-continued

```
                20                  25                  30
Leu Ala Trp Tyr Gln Gln Lys Pro Gly Lys Ala Pro Lys Leu Leu Ile
            35                  40                  45

Tyr Asp Ala Asn Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Phe Gln Tyr Ser Gly Pro Thr Phe
                 85                  90                  95

Gly Gln Gly Thr Lys Val Glu Ile Lys Arg Thr
            100                 105

<210> SEQ ID NO 143
<211> LENGTH: 115
<212> TYPE: PRT
<213> ORGANISM: Homo sapiens

<400> SEQUENCE: 143

Glu Leu Val Glu Ser Gly Gly Gly Leu Val Gln Pro Gly Gly Ser Leu
 1               5                  10                  15

Arg Leu Ser Cys Ala Ala Ser Gly Phe Thr Phe Ser Asn Tyr Gly Ile
             20                  25                  30

Ser Trp Val Arg Gln Ala Pro Gly Lys Gly Leu Glu Trp Val Ser Ala
         35                  40                  45

Ile Ser Tyr Tyr Gly Ser Asn Thr Tyr Tyr Ala Asp Ser Val Lys Gly
     50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Leu Lys Gly Gly Ser Gly Phe Val Trp Gly Gln Gly Thr Leu Val Thr
            100                 105                 110

Val Ser Ser
        115

<210> SEQ ID NO 144
<211> LENGTH: 114
<212> TYPE: PRT
<213> ORGANISM: Homo sapiens

<400> SEQUENCE: 144

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val Tyr Ser
             20                  25                  30

Asn Gly Asn Thr Thr Leu Ser Trp Tyr Leu Gln Lys Pro Gly Gln Ser
         35                  40                  45

Pro Gln Leu Leu Ile Tyr Gly Val Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Tyr
                 85                  90                  95

Asn Ser Phe Pro Arg Thr Phe Gly Gln Gly Thr Lys Val Glu Ile Lys
            100                 105                 110

Arg Thr
```

<210> SEQ ID NO 145
<211> LENGTH: 119
<212> TYPE: PRT
<213> ORGANISM: Homo sapiens

<400> SEQUENCE: 145

Glu Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Gly Met
            20                  25                  30

Ser Trp Val Arg Gln Ala Pro Gly Lys Gly Leu Glu Trp Val Ser Gly
        35                  40                  45

Ile Ser Ser Leu Gly Ser Thr Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Thr Gly Ser Pro Gly Thr Phe Met His Gly Asp His Trp Gly Gln Gly
            100                 105                 110

Thr Leu Val Thr Val Ser Ser
        115

<210> SEQ ID NO 146
<211> LENGTH: 109
<212> TYPE: PRT
<213> ORGANISM: Homo sapiens

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ser Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Tyr Gly Arg Pro Thr
                85                  90                  95

Thr Phe Gly Gln Gly Thr Lys Val Glu Ile Lys Arg Thr
            100                 105

<210> SEQ ID NO 147
<211> LENGTH: 119
<212> TYPE: PRT
<213> ORGANISM: Homo sapiens

<400> SEQUENCE: 147

Glu Leu Val Gln Ser Gly Ala Glu Val Lys Lys Pro Gly Glu Ser Leu
1               5                   10                  15

Lys Ile Ser Cys Lys Gly Ser Gly Tyr Ser Phe Ser Lys Tyr Trp Ile
            20                  25                  30

Gly Trp Val Arg Gln Met Pro Gly Lys Gly Leu Glu Trp Met Gly Ile
        35                  40                  45

Ile Tyr Pro Thr Asp Ser Tyr Thr Arg Tyr Ser Pro Ser Phe Gln Gly
    50                  55                  60

```
Gln Val Thr Ile Ser Ala Asp Lys Ser Ile Ser Thr Ala Tyr Leu Gln
 65                  70                  75                  80

Trp Ser Ser Leu Lys Ala Ser Asp Thr Ala Met Tyr Tyr Cys Ala Arg
                 85                  90                  95

Thr His Gly Tyr Tyr Lys Asn Gly Arg Met Asp Val Trp Gly Gln Gly
            100                 105                 110

Thr Leu Val Thr Val Ser Ser
        115

<210> SEQ ID NO 148
<211> LENGTH: 114
<212> TYPE: PRT
<213> ORGANISM: Homo sapiens

<400> SEQUENCE: 148

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Val His Ser
                 20                  25                  30

Asn Gly Tyr Asn Tyr Leu Ser Trp Tyr Leu Gln Lys Pro Gly Gln Ser
             35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys His Gln Tyr
                 85                  90                  95

Gly Asp Phe Ser Asp Thr Phe Gly Gln Gly Thr Lys Val Glu Ile Lys
            100                 105                 110

Arg Thr

<210> SEQ ID NO 149
<211> LENGTH: 117
<212> TYPE: PRT
<213> ORGANISM: Homo sapiens

<400> SEQUENCE: 149

Glu Leu Val Gln Ser Gly Ala Glu Val Lys Lys Pro Gly Glu Ser Leu
  1               5                  10                  15

Lys Ile Ser Cys Lys Gly Ser Gly Tyr Ser Phe Thr Gly Tyr Ile Ser
                 20                  25                  30

Trp Val Arg Gln Ala Pro Gly Lys Gly Leu Glu Trp Met Gly Ile Ile
             35                  40                  45

Tyr Pro Gly Asp Ser Tyr Thr Asn Tyr Ser Pro Ser Phe Gln Gly Gln
     50                  55                  60

Val Thr Ile Ser Ala Asp Lys Ser Ile Ser Thr Ala Tyr Leu Gln Trp
 65                  70                  75                  80

Ser Ser Leu Lys Ala Ser Asp Thr Ala Met Tyr Tyr Cys Ala Arg Tyr
                 85                  90                  95

Ser Gly Pro Asn Trp Asp Val Met Asp Ser Trp Gly Gln Gly Thr Leu
            100                 105                 110

Val Thr Val Ser Ser
        115

<210> SEQ ID NO 150
<211> LENGTH: 107
<212> TYPE: PRT
```

<213> ORGANISM: Homo sapiens

<400> SEQUENCE: 150

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Tyr
            20                  25                  30

Tyr Val Asn Trp Tyr Gln Gln Leu Pro Gly Thr Ala Pro Lys Leu Leu
            35                  40                  45

Ile Tyr Ala Asp Asp Lys Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Tyr Asp Ser Thr Lys
                85                  90                  95

Asp Asp Ser Val Phe Gly Gly Gly Thr Lys Leu
            100                 105

<210> SEQ ID NO 151
<211> LENGTH: 115
<212> TYPE: PRT
<213> ORGANISM: Homo sapiens

<400> SEQUENCE: 151

Glu Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Gly Met
            20                  25                  30

His Trp Val Arg Gln Ala Pro Gly Lys Gly Leu Glu Tyr Val Ser Ala
            35                  40                  45

Ile Ser Tyr Ser Ser Ser Thr Ser Tyr Ala Asp Ser Val Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Leu Ser Tyr Thr Gly Phe Ala Val Trp Gly Gln Gly Thr Leu Val Thr
            100                 105                 110

Val Ser Ser
        115

<210> SEQ ID NO 152
<211> LENGTH: 103
<212> TYPE: PRT
<213> ORGANISM: Homo sapiens

<400> SEQUENCE: 152

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Tyr Tyr Val
            20                  25                  30

His Trp Tyr Gln Gln Lys Pro Gly Gln Ala Pro Val Leu Val Ile Tyr
            35                  40                  45

Asp Asp Asn Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Phe Gly Lys Val Val
             85                  90                  95

Phe Gly Gly Gly Thr Lys Leu
        100

<210> SEQ ID NO 153
<211> LENGTH: 6675
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 153

| | | | | | |
|---|---|---|---|---|---|
| aattggaggc | tacagtcagt | ggagaggact | ttcactgact | gactgactgc | gtctcaacct | 60 |
| ggggacaagt | ttgtacaaaa | aagcaggctc | tgtctagagg | gcaccatggt | gttgcagacc | 120 |
| caggtcttca | tttctctgtt | gctctggatc | tctggtgcct | acgggatat | ccagatgacc | 180 |
| cagagcccgt | ctagcctgag | cgcgagcgtg | ggtgatcgtg | tgaccattac | ctgcagagcg | 240 |
| agccaggata | ttaataatta | tctgtcttgg | taccagcaga | aaccaggtaa | agcaccgaaa | 300 |
| ctattaattt | atggtgcttc | taatttgcaa | agcggggtcc | cgtcccgttt | tagcggctct | 360 |
| ggatccggca | ctgattttac | cctgaccatt | agcagcctgc | aacctgaaga | cttttgcggtt | 420 |
| tattattgcc | agcagtatta | tggtcgtcct | actacctttg | gccagggtac | gaaagttgaa | 480 |
| attaaacgta | cggtggctgc | accatctgtc | ttcatcttcc | cgccatctga | tgagcagttg | 540 |
| aaatctggaa | ctgcctctgt | tgtgtgcctg | ctgaataact | tctatcccag | agaggccaaa | 600 |
| gtacagtgga | aggtggataa | cgccctccaa | tcgggtaact | cccaggagag | tgtcacagag | 660 |
| caggacagca | aggacagcac | ctacagcctc | agcagcaccc | tgacgctgtc | taaagcagac | 720 |
| tacgagaaac | acaaagtcta | cgcctgcgaa | gtcacccatc | agggcctgag | ctcgcccgtc | 780 |
| acaaagagct | tcaacagggg | agagtgttag | cggccgcgc | ctcgactgtg | ccttctagtt | 840 |
| gccagccatc | tgttgtttgc | ccctcccccg | tgccttcctt | gaccctggaa | ggtgccactc | 900 |
| ccactgtcct | ttcctaataa | aatgaggaaa | ttgcatcgca | ttgtctgagt | aggtgtcatt | 960 |
| ctattctggg | gggtggggtg | gggcaggaca | gcaaggggga | ggattgggaa | gacaatagca | 1020 |
| ggcatgctgg | ggatgcggtg | ggctctatgg | gatgcttatc | gccacgttcg | gcgcgccgtc | 1080 |
| gacgatgtac | gggccagata | tacgcgttga | cattgattat | tgactagtta | ttaatagtaa | 1140 |
| tcaattacgg | ggtcattagt | tcatagccca | tatatggagt | tccgcgttac | ataacttacg | 1200 |
| gtaaatggcc | cgcctggctg | accgcccaac | gacccccgcc | cattgacgtc | aataatgacg | 1260 |
| tatgttccca | tagtaacgcc | aatagggact | ttccattgac | gtcaatgggt | ggactattta | 1320 |
| cggtaaactg | cccacttggc | agtacatcaa | gtgtatcata | tgccaagtac | gccccctatt | 1380 |
| gacgtcaatg | acggtaaatg | gcccgcctgg | cattatgccc | agtacatgac | cttatgggac | 1440 |
| tttcctactt | ggcagtacat | ctacgtatta | gtcatcgcta | ttaccatggt | gatgcggttt | 1500 |
| tggcagtaca | tcaatgggcg | tggatagcgg | tttgactcac | ggggatttcc | aagtctccac | 1560 |
| cccattgacg | tcaatgggag | tttgttttgg | caccaaaatc | aacgggactt | tccaaaatgt | 1620 |
| cgtaacaact | ccgccccatt | gacgcaaatg | ggcggtaggc | gtgtacggtg | gaggtctat | 1680 |
| ataagcagag | ctctctggct | aactagagaa | cccactgctt | actggcttat | cgaaattaat | 1740 |
| acgactcact | atagggagac | ccaagctggc | tagcgccacc | atgaaacacc | tgtggttctt | 1800 |
| cctcctgctg | gtggcagctc | ccagatgggt | cctgtcccag | gtggaattgg | tggaaagcgg | 1860 |
| cggcggcctg | gtgcaaccgg | gcggcagcct | gcgtctgagc | tgcgcggcct | ccggatttac | 1920 |

```
cttttcttct tatggtatgt cttgggtgcg ccaagcccct gggaagggtc tcgagtgggt    1980
gagcggtatc tcttctcttg gtagcactac ctattatgcg gatagcgtga aaggccgttt    2040
taccatttca cgtgataatt cgaaaaacac cctgtatctg caaatgaaca gcctgcgtgc    2100
ggaagatacg gccgtgtatt attgcgcgcg tactggttct cctggtactt ttatgcatgg    2160
tgatcattgg ggccaaggca ccctggtgac ggttagctca gcctccacca agggtccatc    2220
ggtcttcccc ctggcaccct cctccaagag cacctctggg ggcacagcgg ccctgggctg    2280
cctggtcaag gactacttcc ccgaaccggt gacggtgtcg tggaactcag gcgccctgac    2340
cagcggcgtg cacaccttcc cggctgtcct acagtcctca ggactctact ccctcagcag    2400
cgtggtgacc gtgccctcca gcagcttggg cacccagacc tacatctgca acgtgaatca    2460
caagcccagc aacaccaagg tggacaagaa agttgagccc aaatcttgtg acaaaactca    2520
cacatgccca ccgtgcccag cacctgaact cctggggggga ccgtcagtct tcctcttccc    2580
cccaaaaccc aaggacaccc tcatgatctc ccggacccct gaggtcacat gcgtggtggt    2640
ggacgtgagc cacgaagacc ctgaggtcaa gttcaactgg tacgtggacg gcgtggaggt    2700
gcataatgcc aagacaaagc cgcgggagga gcagtacaac agcacgtacc gggtggtcag    2760
cgtcctcacc gtcctgcacc aggactggct gaatggcaag gagtacaagt gcaaggtctc    2820
caacaaagcc ctcccagccc ccatcgagaa aaccatctcc aaagccaaag gcagccccg    2880 agaaccacag gtgtacaccc tgcccccatc ccgggatgag ctgaccaaga accaggtcag    2940
cctgacctgc ctggtcaaag gcttctatcc cagcgacatc gccgtggagt gggagagcaa    3000
tgggcagccg gagaacaact acaagaccac gcctcccgtg ctggactccg acggctcctt    3060
cttcctctac agcaagctca ccgtggacaa gagcaggtgg cagcagggga acgtcttctc    3120
atgctccgtg atgcatgagg ctctgcacaa ccactacacg cagaagagcc tctccctgtc    3180
tccgggtaaa tgagggcccg tttaaaccg ctgatcagcc tcgactgtgc cttctagttg    3240
ccagccatct gttgtttgcc cctcccccgt gccttccttg accctggaag gtgccactcc    3300
cactgtcctt tcctaataaa atgaggaaat tgcatcgcat tgtctgagta ggtgtcattc    3360
tattctgggg ggtggggtgg ggcaggacag caagggggag gattgggaag acaatagcag    3420
gcatgctggg gatgcggtgg gctctatggc ttctgaggcg gaaagaacca gcctcacgtg    3480
gacccagctt tcttgtacaa agtggtcccc ctacagagac gactgactga ctgactggaa    3540
agaggaaggg ctggaagagg aaggagcttg gcgtaatcat ggtcatagct gtttcctgtg    3600
tgaaattgtt atccgctcac aattccacac aacatacgag ccggaagcat aaagtgtaaa    3660
gcctggggtg cctaatgagt gagctaactc acattaattg cgttgcgctc actgcccgct    3720
ttccagtcgg gaaacctgtc gtgccagctg cattaatgaa tcggccaacg cgcggggaga    3780
ggcggtttgc gtattgggcg ctcttccgct tcctcgctca ctgactcgct gcgctcggtc    3840
gttcggctgc ggcgagcggt atcagctcac tcaaaggcgg taatacggtt atccacagaa    3900
tcaggggata acgcaggaaa gaacatgtga gcaaaaggcc agcaaaaggc caggaaccgt    3960
aaaaaggccg cgttgctggc gtttttccat aggctccgcc cccctgacga gcatcacaaa    4020
aatcgacgct caagtcagag gtggcgaaac ccgacaggac tataaagata ccaggcgttt    4080
ccccctggaa gctccctcgt gcgctctcct gttccgaccc tgccgcttac cggatacctg    4140
tccgcctttc tcccttcggg aagcgtggcg ctttctcata gctcacgctg taggtatctc    4200
agttcggtgt aggtcgttcg ctccaagctg ggctgtgtgc acgaaccccc cgttcagccc    4260
gaccgctgcg ccttatccgg taactatcgt cttgagtcca acccggtaag acacgactta    4320
```

```
tcgccactgg cagcagccac tggtaacagg attagcagag cgaggtatgt aggcggtgct    4380
acagagttct tgaagtggtg gcctaactac ggctacacta aaggacagt atttggtatc     4440 tgcgctctgc tgaagccagt taccttcgga aaaagagttg gtagctcttg atccggcaaa    4500
caaaccaccg ctggtagcgg tggtttttt gtttgcaagc agcagattac gcgcagaaaa     4560
aaaggatctc aagaagatcc tttgatcttt tctacggggt ctgacgctca gtggaacgaa    4620
aactcacgtt aagggatttt ggtcatgaga ttatcaaaaa ggatcttcac ctagatcctt    4680
ttaaattaaa aatgaagttt taaatcaatc taaagtatat atgagtaaac ttggtctgac    4740
agttaccaat gcttaatcag tgaggcacct atctcagcga tctgtctatt tcgttcatcc    4800
atagttgcct gactccccgt cgtgtagata actacgatac gggagggctt accatctggc    4860
cccagtgctg caatgatacc gcgagaccca cgctcaccgg ctccagattt atcagcaata    4920
aaccagccag ccggaagggc cgagcgcaga agtggtcctg caactttatc cgcctccatc    4980
cagtctatta attgttgccg ggaagctaga gtaagtagtt cgccagttaa tagtttgcgc    5040
aacgttgttg ccattgctac aggcatcgtg gtgtcacgct cgtcgtttgg tatggcttca    5100
ttcagctccg gttcccaacg atcaaggcga gttacatgat cccccatgtt gtgcaaaaaa    5160
gcggttagct ccttcggtcc tccgatcgtt gtcagaagta agttggccgc agtgttatca    5220
ctcatggtta tggcagcact gcataattct cttactgtca tgccatccgt aagatgcttt    5280
tctgtgactg gtgagtactc aaccaagtca ttctgagaat agtgtatgcg gcgaccgagt    5340
tgctcttgcc cggcgtcaat acgggataat accgcgccac atagcagaac tttaaaagtg    5400
ctcatcattg gaaaacgttc ttcggggcga aaactctcaa ggatcttacc gctgttgaga    5460
tccagttcga tgtaacccac tcgtgcaccc aactgatctt cagcatcttt tactttcacc    5520
agcgtttctg ggtgagcaaa aacaggaagg caaaatgccg caaaaaaggg aataagggcg    5580
acacggaaat gttgaatact catactcttc ctttttcaat attattgaag catttatcag    5640
ggttattgtc tcatgagcgg atacatattt gaatgtattt agaaaaataa acaaataggg    5700
gttccgcgca catttccccg aaaagtgcca cctgacgtct aagaaaccat tattatcatg    5760
acattaacct ataaaaatag gcgtatcacg aggccctttc gtctcgcgcg tttcggtgat    5820
gacggtgaaa acctctgaca catgcagctc ccggagacgg tcacagcttg tctgtaagcg    5880
gatgccggga gcagacaagc ccgtcagggc gcgtcagcgg gtgttggcgg gtgtcggggc    5940
tggcttaact atgcggcatc agagcagatt gtactgagag tgcaccataa aattgtaaac    6000
gttaatattt tgttaaaatt cgcgttaaat ttttgttaaa tcagctcatt ttttaaccaa    6060
taggccgaaa tcggcaaaat cccttataaa tcaaaagaat agcccgagat agggttgagt    6120
gttgttccag tttggaacaa gagtccacta ttaaagaacg tggactccaa cgtcaaaggg    6180
cgaaaaaccg tctatcaggg cgatggccca ctacgtgaac catcacccaa atcaagtttt    6240
ttggggtcga ggtgccgtaa agcactaaat cggaaccta agggagcccc cgatttaga     6300 gcttgacggg gaaagccggc gaacgtggcg agaaaggaag ggaagaaagc gaaaggagcg    6360
ggcgctaggg cgctggcaag tgtagcggtc acgctgcgcg taaccaccac acccgccgcg    6420
cttaatgcgc cgctacaggg cgcgtactat ggttgctttg acgtatgcgg tgtgaaatac    6480
cgcacagatg cgtaaggaga aaataccgca tcaggcgcca ttcgccattc aggctgcgca    6540
actgttggga agggcgatcg gtgcgggcct cttcgctatt acgccagctg gcgaaagggg    6600
```

```
gatgtgctgc aaggcgatta agttgggtaa cgccagggtt ttcccagtca cgacgttgta    6660
aaacgacggc cagtg                                                     6675
```